United States Patent [19]
Whittaker et al.

[11] Patent Number: 5,516,783
[45] Date of Patent: May 14, 1996

[54] 4-(1 H-2-METHYLIMIDAZO[4,5-C] PYRIDINYLMETHYL) PHENYLSULPHONAMIDE DERIVATIVES AS ANTAGONIST OF PAF

[75] Inventors: Mark Whittaker; Stephen A. Bowles; Andrew Miller, all of Oxford, United Kingdom

[73] Assignee: British Biotech Pharmaceuticals Limited, Cowley, United Kingdom

[21] Appl. No.: 284,570

[22] PCT Filed: Feb. 10, 1993

[86] PCT No.: PCT/GB93/00273

§ 371 Date: Oct. 27, 1994

§ 102(e) Date: Oct. 27, 1994

[87] PCT Pub. No.: WO93/16075

PCT Pub. Date: Aug. 19, 1993

[30] Foreign Application Priority Data

Feb. 11, 1992 [GB] United Kingdom ................. 9202791

[51] Int. Cl.$^6$ ..................... A61K 31/435; C07D 471/04

[52] U.S. Cl. .............................. 514/303; 546/118
[58] Field of Search ................. 546/118; 514/303

[56] References Cited

FOREIGN PATENT DOCUMENTS 0260613  3/1988  European Pat. Off. .
WO9203423  3/1992  WIPO .

*Primary Examiner*—Bernard Dentz
*Attorney, Agent, or Firm*—Hale and Dorr

[57] ABSTRACT

The present invention is directed to compounds of general formula I as well their pharmaceutically and veterinarily acceptable acid addition salts or hydrates thereof. The present invention is further directed to pharmaceutical and veterinary compositions containing the compounds of general formula I. The present compounds of general formula I are antagonist of platelet activating factor (PAF). Accordingly, the present invention is also directed to methods for preventing, treating or ameliorating in human or mammalian animals, various diseases or physiological conditions mediated by PAF.

14 Claims, No Drawings

4-(1 H-2-METHYLIMIDAZO[ 4,5-C] PYRIDINYLMETHYL)PHENYLSULPHONAMIDE DERIVATIVES AS ANTAGONIST OF PAF

This application is a 371 of PCT/GB93/00273 filed Feb. 10, 1993.

This invention relates primarily to novel compounds which are antagonists of platelet activating factor.

Platelet activating factor (PAF) is a bioactive phospholipid which has been identified as 1-O-hexadecyl/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds that have been disclosed as possessing activity as PAF antagonists include compounds which are structurally related to the PAF molecule such as glycerol derivatives (EP-A-0238202); and heterocyclic compounds such as 5-oxy derivatives of tetrahydrofuran (U.S. Pat. No. 4,888, 337) and 2,5-diaryl tetrahydrofurans (EP-A-0144804). Recently a more potent 2,5-diaryl tetrahydrofuran derivative, (trans)-2-(3-methoxy-5-methylsulphonyl-4-propoxyphenyl)-5-( 3,4,5-trimethoxyphenyl)tetrahydrofuran (L-659,989) has been disclosed (EP-A-0199324). In our International patent application No. WO 91/17157 we disclose a series of γ-butyrolactol derivatives as PAF antagonists. The compounds of WO 91/17157 differ from the 5-oxy derivatives of tetrahydofuran described in U.S. Pat. No. 4,888,337 and from the 2,5-diaryl tetrahydrofurans such as L-659,989, in that they feature an appended heterocycle with an unsubstituted $sp^2$ nitrogen atom. There are a number of other PAF antagonists, in addition to those of WO 91/17157, for which the presence of a heterocyclic $sp^2$ nitrogen atom appears to be an important requirement for activity (Whittaker, M., Curr. Opin. Thera. Patents 2(5), 583–623 (1992)).

For the compounds of the present invention the presence of a heterocyclic group possessing an unsubstituted $sp^2$ nitrogen atom is also a requirement for PAF antagonist activity. However, the compounds of the present invention differ from the other PAF antagonists referred to above in that they are amino acid derivatives.

The present invention provides novel and useful substituted amino acid derivatives and their pharmaceutically acceptable acid addition salts, and pharmaceutical uses thereof as PAF antagonists.

According to a first aspect of the invention there is provided a compound of general formula I;

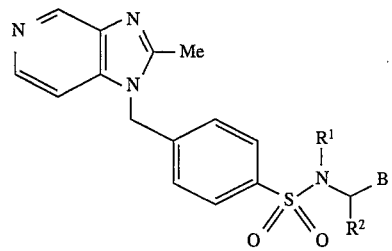

wherein:

$R^1$ represents hydrogen, —$C_1$–$C_6$ alkyl, —$C_2$–$C_6$ alkenyl, —$C_2$–$C_6$ alkynyl, —$COC_1$–$C_6$ alkyl, —$CO_2C_1$–$C_6$ alkyl, —($COC_1$–$C_6$ alkyl)phenyl, —($CO_2C_1$–$C_6$ alkyl)phenyl, —($C_1$–$C_6$ alkyl)$OC_1$–$C_6$ alkyl, —($C_1$–$C_6$ alkyl)$SC_1$–$C_6$ alkyl, —($C_1$–$C_6$ alkyl)$CO_2C_1$–$C_6$ alkyl, —$C_3$–$C_8$ cycloalkyl, —$C_4$–$C_8$ cycloalkenyl or a group —D wherein D represents a group:

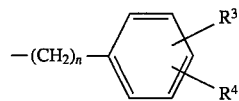

wherein n is an integer from 0 to 3, and each of $R^3$ and $R^4$ is independently hydrogen, —$C_1$–$C_6$ alkyl, —$C_2$–$C_6$ alkenyl, —$C_2$–$C_6$ alkynyl, halogen, —CN, —$CO_2H$, —$CO_2C_1$–$C_6$ alkyl, —$CONH_2$, —$CONHC_1$–$C_6$ alkyl, —$CONH(C_1$–$C_6$ alkyl)$_2$, —CHO, —$CH_2OH$, —$CF_3$, —$OC_1$–$C_6$ alkyl, —$SC_1$–$C_6$ alkyl, —$SOC_1$–$C_6$ alkyl, —$SO_2C_1$–$C_6$ alkyl, —$NH_2$ or —NHCOMe;

$R^2$ represents hydrogen, halogen, —$C_1$–$C_6$ alkyl optionally substituted by one or more halogen atoms, —$C_2$–$C_6$ alkenyl, —$C_2$–$C_6$ alkynyl, —($C_1$–$C_6$ alkyl)$CO_2C_1$–$C_6$ alkyl, —($C_1$–$C_6$ alkyl)$SC_1$–$C_6$ alkyl, —($C_1$–$C_6$ alkyl)$OC_1$–$C_6$ alkyl, —($C_1$–$C_6$ alkyl)$N(C_1$–$C_6$ alkyl)$_2$, —$C_3$–$C_8$ cycloalkyl, —$C_4$–$C_8$ cycloalkenyl, —($C_1$–$C_6$ alkyl)$C_3$–$C_8$ cycloalkyl, —($C_1$–$C_6$ alkyl)$C_4$–$C_8$ cycloalkenyl, —($C_1$–$C_6$ alkyl)$OC_3$–$C_8$ cycloalkyl, —($C_1$–$C_6$ alkyl)$OC_4$–$C_8$ cycloalkenyl, —($C_1$–$C_6$ alkyl)$SC_3$–$C_8$ cycloalkyl, —($C_1$–$C_6$ alkyl)$SC_4$–$C_8$ cycloalkenyl, a side chain of a naturally occurring amino acid, a group —D as defined above or a —($C_1$–$C_6$ alkyl)OD group wherein D is as defined above;

B represents
a) a —$(CH_2)_mX$ group wherein m is an integer from 0 to 2 and the group X represents a 5- or 6-membered heterocyclic ring, which heterocyclic ring may be optionally fused to a benzene ring or to a further 5-, 6- or 7-membered heterocyclic ring containing one or more nitrogen atoms, wherein at least one of the said heterocyclic rings may also contain an oxygen or sulphur atom, and wherein any of the rings may be optionally substituted with one or more substituents selected from hydrogen, halogen, —$C_1$–$C_4$ perfluoroalkyl, hydroxyl, carbonyl, thiocarbonyl, carboxyl, —$CONH_2$, a group —D wherein D is as defined above, —$R^5$, —$OR^5$, —$SR^5$, —$SOR^5$, —$SO_2R^5$, —$NHR^5$, —$NR^5R^5$, —$CO_2R^5$ or —$CONHR_5$ wherein $R^5$ is —$C_1$–$C_{18}$ alkyl, —$C_2$–$C_6$ alkenyl, —$C_2$–$C_6$ alkynyl, —$C_3$–$C_8$ cycloalkyl or —$C_4$–$C_8$ cycloalkenyl each of which is optionally substituted with one or more substituents selected from halogen, hydroxyl, amino, carboxyl, —$C_1$–$C_4$ perfluoroalkyl, —$C_1$–$C_6$ alkyl, —$C_2$–$C_6$ alkenyl, —$C_2$–$C_6$ alkynyl, —$C_3$–$C_8$ cycloalkyl, —$C_4$–$C_8$ cycloalkenyl, —$OC_1$–$C_6$ alkyl, —$SC_1$–$C_6$ alkyl, tetrazol-5-yl, a group —D wherein D is as defined above or a heteroaryl or heteroarylmethyl group;

b) a group Y, wherein Y is —$CH_2OH$, —$CH_2OC(=O)R^6$, —$CH_2OC(=O)C(=O)OR^6$, —$CH_2OSO_2R^6$, —$CH_2OP(=O)OR^6OR^6$, —$NHC(=O)OR^6$, —$CH_2OC(=O)NHR^6$, —$CH_2CO_2R^6$ or —$CH_2OC(=O)CH_2SR^6$ group wherein $R^6$ is, —$C_1$–$C_{18}$ alkyl, —$C_2$–$C_{20}$ alkenyl, —$C_2$–$C_{18}$ alkynyl, —($C_1$–$C_6$ alkyl)$OC_1$–$C_6$ alkyl, —($C_1$–$C_6$ alkyl)$SC_1$–$C_6$ alkyl, —($C_1$–$C_6$ alkyl)$O$($C_1$–$C_6$ alkyl)$OC_1$–$C_6$ alkyl, —$C_3$–$C_8$ cycloalkyl, —$C_4$–$C_8$ cycloalkenyl, a group D as defined above or a group —$(CH_2)_mX$ as defined above;

c) a —$CH_2OC(=O)CHR^2Y$ group wherein $R^2$ and Y are as defined above;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "$C_1$–$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tertbutyl, pentyl, neopentyl and hexyl.

As used herein the term "$C_1$–$C_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to six carbon atoms may be preferred.

As used herein the term "$C_2$–$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_2$–$C_{20}$ alkenyl" refers to straight chain, branched chain or cycloalkenylalkenyl hydrocarbon groups having from two to twenty carbon atoms and having in addition one or more double bonds, of either E or Z stereochemistry where applicable. This term would include for example, vinyl, 1-propenyl, 1- and 2-butenyl, 2-methyl-2-propenyl, geranyl, retinyl and farnesyl. From two to six carbon atoms may be preferred.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "$C_2$–$C_{18}$ alkynyl" refers to straight chain or branched chain hydrocarbon groups having from two to eighteen carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

As used herein, the term "$C_1$–$C_4$ perfluoroalkyl" refers to straight chain or branched chain groups having from one to four carbon atoms and substituted by more than one fluorine atom. This term would include for example, trifluoromethyl, 2,2,2-trifluoroethyl, pentafluoroethyl, 3,3,3-trifluoro-n-propyl, sexafluoro-i-propyl, septafluoro-n-propyl, septafluoro-i-propyl, 4,4,4-trifluoro-n-butyl, nonafluoro-n-butyl, nonafluoro-sec-butyl and nonafluoro-i-butyl. As used herein the term "$OC_1$–$C_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$SC_1$–$C_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "$C_3$–$C_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "$C_4$–$C_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. The amino acid side chains may be protected; for example the carboxyl groups of aspartic acid, glutamic acid and α-aminoadipic acid may be esterified (for example as a $C_1$–$C_6$ alkyl ester), the amino groups of lysine, ornithine, 5-hydroxylysine, 4-hydroxyproline may be converted to amides (for example as a $COC_1$–$C_6$ alkyl amide) or carbamates (for example as a $C(=O)OC_1$–$C_6$ alkyl or $C(=O)OCH_2Ph$ carbamate), the hydroxyl groups of 5-hydroxylysine, 4-hydroxyproline, serine, threonine, tyrosine, 3,4-dihydroxyphenylalanine, homoserine, α-methylserine and thyroxine may be converted to ethers (for example a $C_1$–$C_6$ alkyl or a ($C_1$–$C_6$ alkyl)phenyl ether) or esters (for example a $C(=O)C_1$–$C_6$ alkyl ester) and the thiol group of cysteine may be converted to thioethers (for example a $C_1$–$C_6$ alkyl thioether) or thioesters (for example a $C(=O)C_1$–$C_6$ alkyl thioester). The stereochemistry at the carbon atom to which the amino acid side chain is attached may be either D or L.

As used herein, the term "5- or 6-membered heterocyclic ring" refers to such rings having from 5 to 6 atoms in the ring wherein the heteroatom(s) may be one or more nitrogen, oxygen or sulphur atoms. For example heterocycles containing nitrogen, oxygen, or sulphur alone or containing two nitrogen atoms, a nitrogen and an oxygen atom, a nitrogen and a sulphur atom, two nitrogen atoms and an oxygen atom, two nitrogen atoms and a sulphur atom, three nitrogen atoms or four nitrogen atoms.

As used herein, the term "heteroaryl" refers to a 5- or 6-membered substituted or unsubstituted aromatic heterocycle containing one or more heteroatoms. Illustrative of such rings are thienyl, furyl, imidazolyl, oxadiazolyl, pyridinyl, pyrazinyl each of which may be optionally substituted by methyl or methoxy.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

It is considered that the main structural feature of compounds of general formula I that is particularly significant in providing their PAF antagonist activity, is the subunit (i)

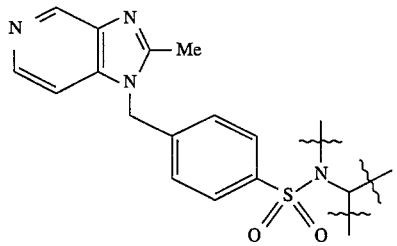

(i)

There may be considerable variation of the substituent groups $R^1$, $R^2$ and B without loss of such activity. Any of the wide range of substituents $R^1$, $R^2$ and B defined above may be used with retention of PAF antagonist activity. Though a preferred substituent for the group $R^2$ is the side chain of the amino acid L-leucine (i.e. sec-butyl).

The 1H-2-methylimidazo[4,5-c]pyridinyl group of the subunit is an important requirement for PAF antagonist activity. However, it is expected that PAF antagonist activity may be found in compounds analogous to those of general formula I above, wherein the 1H-2-methylimidazo[4,5-c]pyridinyl group is replaced by a different $sp^2$ nitrogen heterocycle. The variety of $sp^2$ nitrogen heterocycles that could provide PAF antagonist activity include those disclosed in our patent application WO 91/17157 and those recently described by Whittaker (Whittaker, M., Curr. Opin. Thera. Patents 2(5), 583–623 (1992)) and Cooper (Cooper, K., et al., J. Med. Chem. 35(17), 3115–3129 (1992)). The exact nature of the interaction of the $sp^2$ nitrogen heterocycle and the receptor has not been determined, but it would appear that it is important for the heterocycle to possess at least one unsubstituted $sp^2$ nitrogen atom within the heterocyclic ring.

Although in this application the only substituents claimed for the subunit (i) are $R^1$, $R^2$ and B it is understood that the introduction of further substituents on the 2-methylimidazo[4,5-c]pyridinyl group, the benzylic carbon atom and/or the 1,4-disubstituted phenyl ring of subunit (i) will lead to compounds that retain PAF antagonist activity.

Preferred compounds include those in which, independently or in any compatible combination:

$R^1$ represents a hydrogen atom, a —$C_1$–$C_6$ alkyl (for example methyl, ethyl or propyl) group, a —$C_2$–$C_6$ alkenyl (for example allyl) group or a group —D;

$R^2$ represents a hydrogen atom, a —$C_1$–$C_6$ alkyl (for example ethyl, n-butyl or t-butyl) group, a —$C_2$–$C_6$ alkenyl (for example allyl) group, a —($C_1$–$C_6$ alkyl)$C_3$–$C_8$ cycloalkyl (for example cyclopropylmethyl, cyclopentylmethyl or cyclohexylmethyl) group, a side chain of a naturally occurring amino acid (for example the side chain of leucine, isoleucine, phenylalanine, valine, tryptophan, methionine or tyrosine) or a group D;

in the group D, $R^3$ represents a hydrogen atom, a —$C_1$–$C_6$ alkyl (for example methyl) group, a halogen (for example fluorine, chlorine or bromine) atom, a —$CF_3$ group or a —$OC_1$–$C_6$ alkyl (for example methoxy) group;

in the group D, $R^4$ represents a hydrogen atom or a —$OC_1$–$C_6$ alkyl (for example methoxy) group;

in the group —$(CH_2)_m X$, X represents a furanyl (for example furan-2-yl) group, a thienyl (for example thien-2-yl) group, a pyrrolinyl (for example pyrrol-2-yl) group, a tetrahydrofuranyl (for example tetrahydrofuran-2-yl) group, an oxadiazolyl (for example 1,2,4-ozadiazol-5-yl, 1,2,4-ozadiazol-3-yl or 1,3,4-oxadiazol-2-yl) group, a thiadiazolyl (for example 1,2,4-thiadiazol-5-yl or 1,3,4-thiadiazol-2-yl) group, a pyridinyl (for example pyridin-2-yl, pyridin-3-yl or pyridin-4-yl) group, a piperazinyl (for example piperazin-1-yl) group, a benzotriazolyl (for example benzotriazol-2-yl) group, a pyrazinyl (for example pyrazin-2-yl) group, a pyridazinyl (for example 1,2-pyridazin-3-yl) group, a pyrimidinyl (for example 1,3-pyrimidin-5-yl) group, a dithianyl (for example 1,3-dithian-2-yl) group, a benzo[b]thienyl (for example benzo[b]thien-2-yl) group, a isoxazolyl (for example isoxazol-5-yl) group or a quinolinyl (for example quinolin-3-yl);

the group X may be optionally substituted with one or more substituents selected from hydrogen, a group —D, —$R^5$ or —$CO_2R^5$.

$R^5$ represents a —$C_1$–$C_{18}$ alkyl (for example methyl, ethyl, n-propyl, n-butyl or octadecyl) group or a —$OC_1$–$C_6$ alkyl (for example methoxy) group;

$R_6$ represents a —$C_1$–$C_{18}$ alkyl (for example methyl, ethyl, n-propyl, i-propyl, n-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl or n-octadecyl) group, a —$C_2$–$C_{20}$ alkenyl (for example retinyl) group, a group —D or a group —$(CH_2)_m X$;

Exemplary compounds include:
1. N-Methyl-N-4-(1H-2-methylimidazo[4,5-c]pyridinylmethyl)phenyl sulphonyl-L-leucinol,
2. N-4-(1H-2-Methylimidazo[4,5-c]pyridinylmethyl)phenylsulphonyl-L-leucinol,
3. N-Methyl-N-4-(1H-2-methylimidazo[4,5-c]pyridinylmethyl)phenylsulphonyl-D-leucinol,
4. N-Ethyl-N-4-(1H-2-methylimidazo[4,5-c]pyridinylmethyl)phenylsulphonyl-L-leucinol,
5. N-Allyl-N-4-(1H-2-methylimidazo[4,5-c]pyridinylmethyl)phenylsulphonyl-L-leucinol,
6. N-Propyl-N-4-(1H-2-methylimidazo[4,5-c]pyridinylmethyl)phenylsulphonyl-L-leucinol,
7. N-Benzyl-N-4-(1H-2-methylimidazo[4,5-c]pyridinylmethyl)phenylsulphonyl-L-leucinol,
8. N-4-Methoxybenzyl-N-4-(1H-2-methylimidazo[4,5-c]pyridinylmethyl)-phenylsulphonyl-L-leucinol, 9. N-Methyl-N-4-(1H-2-methylimidazo[4,5-c]pyridinylmethyl)phenylsulphonyl-L-isoleucinol,
10. N-Methyl-N-4-(1H-2-methylimidazo[4,5-c]pyridinylmethyl)phenylsulphonyl-L-phenylalaninol,
11. N-Methyl-N-4-(1H-2-methylimidazo[4,5-c]pyridinylmethyl)phenylsulphonyl-L-valinol,
12. N-Methyl-N-4-(1H-2-methylimidazo[4,5-c]pyridinylmethyl)phenylsulphonyl-L-tryptophanol,
13. N-Methyl-N-4-(1H-2-methylimidazo[4,5-c]pyridinylmethyl)phenylsulphonyl-L-methioninol,
14. N-Methyl-N-4-(1H-2-methylimidazo[4,5-c]pyridinylmethyl)phenylsulphonyl-0-methyl-L-tyrosinol,
15. N-Methyl-N-4-(1H-2-methylimidazo[4,5-c]pyridinylmethyl)phenylsulphonyl-L-norleucinol,
16. N-Methyl-N-4-(1H-2-methylimidazo[4,5-c]pyridinylmethyl)phenylsulphonyl-L-phenylglycinol,
17. N-Methyl-N-4-(1H-2-methylimidazo[4,5-c]pyridinylmethyl)phenylsulphonyl-L-t-butylglycinol,
18. N-Methyl-N-4-(1H-2-methylimidazo[4,5-c]pyridinylmethyl)phenylsulphonyl-D,L-ethylglycinol,
19. N-Methyl-N-4-(1H-2-methylimidazo[4,5-c]pyridinylmethyl)phenylsulphonyl-D,L-allylglycinol,
20. N-Methyl-N-4-(1H-2-methylimidazo[4,5-c]pyridinylmethyl)phenylsulphonyl-L-cyclopropylalaninol,
21. N-Methyl-N-4-(1H-2-methylimidazo[4,5-c]pyridinylmethyl)phenylsulphonyl-L-cyclopentylalaninol,
22. N-Methyl-N-4-(1H-2-methylimidazo[4,5-c]pyridinylmethyl)phenylsulphonyl-L-cyclohexylalaninol,
23. O-Ethanoyl-N-methyl-N-4-(1H-2-methylimidazo[4,5-c]pyridinylmethyl)phenylsulphonyl-L-leucinol,
24. O-Ethanoyl-N-methyl-N-4-(1H-2-methylimidazo[4,5-c]pyridinylmethyl)phenylsulphonyl-D-leucinol,
25. O-Ethanoyl-N-ethyl-N-4-(1H-2-methylimidazo[4,5-c]pyridinylmethyl)phenylsulphonyl-L-leucinol,
26. O-Ethanoyl-N-allyl-N-4-(1H-2-methylimidazo[4,5-c]pyridinylmethyl)phenylsulphonyl-L-leucinol,
27. O-Ethanoyl-N-propyl-N-4-(1H-2-methylimidazo[4,5-c]pyridinylmethyl)phenylsulphonyl-L-leucinol,
28. O-Ethanoyl-N-benzyl-N-4-(1H-2-methylimidazo[4,5-c]pyridinylmethyl)phenylsulphonyl-L-leucinol,
29. O-Ethanoyl-N-4-methoxybenzyl-N-4-(1H-2-methylimidazo[4,5-c]pyridinylmethyl)phenylsulphonyl-L-leucinol,
30. O-Ethanoyl-N-methyl-N-4-(1H-2-methylimidazo[4,5-c]pyridinylmethyl)-phenylsulphonyl-L-isoleucinol,
31. O-Ethanoyl-N-methyl-N-4-(1H-2-methylimidazo[4,5-c]pyridinylmethyl)phenylsulphonyl-L-phenylalininol,
32. O-Ethanoyl-N-methyl-N-4-(1H-2-methylimidazo[4,5-c]pyridinylmethyl)phenylsulphonyl-L-valinol,
33. O-Ethanoyl-N-methyl-N-4-(1H-2-methylimidazo[4,5-c]pyridinylmethyl)phenylsulphonyl-L-tryptophanol,
34. O-Ethanoyl-N-methyl-N-4-(1H-2-methylimidazo[4,5-c]pyridinylmethyl)phenylsulphonyl-L-methioninol,
35. O-Ethanoyl-N-methyl-N-4-(1H-2-methylimidazo[4,5-c]pyridinylmethyl)phenylsulphonyl-O'-methyl-L-tyrosinol,
36. O-Ethanoyl-N-methyl-N-4-(1H-2-methylimidazo[4,5-c]pyridinylmethyl)phenylsulphonyl-L-norleucinol,
37. O-Ethanoyl-N-methyl-N-4-(1H-2-methylimidazo[4,5-c]pyridinylmethyl)phenylsulphonyl-L-phenylglycinol,
38. O-Ethanoyl-N-methyl-N-4-(1H-2-methylimidazo[4,5-c]pyridinylmethyl)phenylsulphonyl-L-t-butylglycinol,
39. O-Ethanoyl-N-methyl-N-4-(1H-2-methylimidazo[4,5-c]pyridinylmethyl)phenylsulphonyl-D,L-ethylglycinol,
40. O-Ethanoyl-N-methyl-N-4-(1H-2-methylimidazo[4,5-c]pyridinylmethyl)phenylsulphonyl-D,L-allylglycinol,
41. O-Ethanoyl-N-methyl-N-4-(1H-2-methylimidazo[4,5-c]pyridinylmethyl)phenylsulphonyl-L-cyclopropylalininol,
42. O-Ethanoyl-N-methyl-N-4-(1H-2-methylimidazo[4,5-c]pyridinylmethyl)phenylsulphonyl-L-cyclopentylalininol
43. O-Ethanoyl-N-methyl-N-4-(1H-2-methylimidazo[4,5-c]pyridinylmethyl)phenylsulphonyl-cyclohexylalininol
44. O-Octadecanoyl-N-methyl-N-4-(1H-2-methylimidazo[4,5-c]pyridinylmethyl)phenylsulphonyl-L-leucinol,
45. O-Propanoyl-N-methyl-N-4-(1H-2-methylimidazo[4,5-c]pyridinyl-methyl)phenylsulphonyl-L-leucinol,
46. O-2-Furoyl-N-methyl-N-4-(1H-2-methylimidazo[4,5-c]pyridinylmethyl)phenylsulphonyl-L-leucinol,
47. O-Ethyloxaloyl-N-methyl-N-4-(1H-2-methylimidazo[4,5-c]pyridinylmethyl)phenylsulphonyl-L-leucinol,
48. O-Benzoyl-N-methyl-N-4-(1H-2-methylimidazo[4,5-c]pyridinylmethyl)phenylsulphonyl-L-leucinol,
49. O-2-Acetoxybenzoyl-N-methyl-N-4-(1H-2-methylimidazo[4,5-c]pyridinylmethyl)phenylsulphonyl-L-leucinol,
50. O-Propanoyl-N-4-(1H-2-methylimidazo[4,5-c]pyridinylmethyl)phenylsulphonyl-L-leucinol,
51. O-Propanoyl-N-ethyl-N-4-(1H-2-methylimidazo[4,5-c]pyridinylmethyl)phenylsulphonyl-L-leucinol,
52. O-Propanoyl-N-allyl-N-4-(1H-2-methylimidazo[4,5-c]pyridinylmethyl)phenylsulphonyl-L-leucinol,
53. O-Propanoyl-N-methoxybenzyl-N-4-(1H-2-methylimidazo[4,5-c]pyridinylmethyl)phenylsulphonyl-L-leucinol,
54. O-Propanoyl-N-methyl-N-4-(1H-2-methylimidazo[4,5-c]pyridinylmethyl)phenylsulphonyl-L-isoleucinol,
55. O-Propanoyl-N-methyl-N-4-(1H-2-methylimidazo[4,5-c]pyridinylmethyl)phenylsulphonyl-L-cyclopentylalininol,
56. O-Butanoyl-N-methyl-N-4-(1H-2-methylimidazo[4,5-c]pyridinylmethyl)phenylsulphonyl-L-leucinol,
57. O-Pentanoyl-N-methyl-N-4-(1H-2-methylimidazo[4,5-c]pyridinylmethyl)phenylsulphonyl-L-leucinol,
58. O-Hexanoyl-N-methyl-N-4-(1H-2-methylimidazo[4,5-c]pyridinylmethyl)phenylsulphonyl-L-leucinol,
59. O-Octanoyl-N-methyl-N-4-(1H-2-methylimidazo[4,5-c]pyridinylmethyl)phenylsulphonyl-L-leucinol,
60. O-Decanoyl-N-methyl-N-4-(1H-2-methylimidazo[4,5-c]pyridinylmethyl)phenylsulphonyl-L-leucinol,
61. O-Dodecanoyl-N-methyl-N4-(1H-2-methylimidazo[4,5-c]pyridinylmethyl)phenylsulphonyl-L-leucinol,
62. O-Tetradecanoyl-N-methyl-N-4-(1H-2-methylimidazo[4,5-c]pyridinylmethyl)phenylsulphonyl-L-leucinol,
63. O-Hexadecanoyl-N-methyl-N-4-(1H-2-methylimidazo[4,5-c]pyridinylmethyl)phenylsulphonyl-L-leucinol,
64. O-2-Thiophenecarbonyl-N-methyl-N-4-(1H-2-methylimidazo[4,5c]pyridinylmethyl)phenylsulphonyl-L-leucinol,
65. O-2-Tetrahydrofuroyl-N-methyl-N-4-(1H-2-methylimidazo[4,5-c]pyridinylmethyl)phenylsulphonyl-L-leucinol,
66. O-2-Pyridinecarbonyl-N-Methyl-N-4-(1H-2-methylimidazo[4,5-c]pyridinylmethyl)phenylsulphonyl-L-leucinol,
67. O-3-Pyridinecarbonyl-N-methyl-N-4-(1H-2-methylimidazo[4,5-c]pyridinylmethyl)phenylsulphonyl-L-leucinol,
68. O-4-Pyridinecarbonyl-N-methyl-N-4-(1H-2-methylimidazo[4,5-c]pyridinylmethyl)phenylsulphonyl-L-leucinol,
69. O-3-Quinolinecarbonyl-N-methyl-N-4-(1H-2-methylimidazo[4,5-c]pyridinylmethyl)phenylsulphonyl-L-leucinol,
70. O-2-Trifluoromethylbenzoyl-N-methyl-N-4-(1H-2-methylimidazo[4,5-c]pyridinylmethyl)phenylsulphonyl-L-leucinol,
71. O-2-Bromobenzoyl-N-methyl-N-4-(1H-2-methylimidazo[4,5-c]pyridinylmethyl)phenylsulphonyl-L-leucinol,
72. O-3-Chlorobenzoyl-N-methyl-N-4-(1H-2-methylimidazo[4,5-c]pyridinylmethyl)phenylsulphonyl-L-leucinol, 73. O-4-Methoxybenzoyl-N-methyl-N-4-(1H-2-methylimidazo[ 4,5-c]pyridinylmethyl)phenylsulphonyl-L-leucinol,
74. O-4-Fluorobenzoyl-N-methyl-N-4-(1H-2-methylimidazo[ 4,5-c]pyridinylmethyl)phenylsulphonyl-L-leucinol,
75. O-3,4-Dimethoxybenzoyl-N-methyl-N-4-(1H-2-methylimidazo[ 4,5-c]pyridinylmethyl)phenylsulphonyl-L-leucinol,
76. O-3-Chloro-4-methoxybenzoyl-N-methyl-N-4-(1H-2-methylimidazo[4,5-c]pyridinylmethyl)phenylsulphonyl-L-leucinol,
77. O-2,2-Dimethylpropanoyl-N-methyl-N-4-(1H-2-methylimidazo[ 4,5-c]pyridinylmethyl)phenylsulphonyl-L-leucinol,
78. O-2-(3,4-Dimethoxyphenylmercapto)ethanoyl-N-methyl-N-4-(1H-2-methylimidazo[4,5-c]pyridinylmethyl)phenylsulphonyl-L-leucinol,
79. O-Retinoyl-N-methyl-N-4-(1H-2-methylimidazo[ 4,5-c]pyridinylmethyl)phenylsulphonyl-L-leucinol,
80. O-2-(4-Methoxyphenyl)ethanoyl-N-methyl-N-4-(1H-2-methylimidazo[ 4,5c]pyridinylmethyl)phenylsulphonyl-L-leucinol,
81. O-2-(3,4-Dimethoxyphenyl)ethanoyl-N-methyl-N-4-(1H-2-methylimidazo[4,5-c]pyridinylmethyl)phenylsulphonyl-L-leucinol,
82. O-3-(4-Methoxyphenyl)propanoyl-N-methyl-N-4-(1H-2-methylimidazo[4,5-c]pyridinylmethyl)phenylsulphonyl-L-leucinol,
83. O-3-(3,4-Dimethoxyphenyl)propanoyl-N-methyl-N-4-(1H-2-methylimidazo[4,5-c]pyridinylmethyl)phenylsulphonyl-L-leucinol,
84. O-3-(3-Chloro-4-methoxyphenyl)propanoyl-N-methyl-N-4-(1H-2-methylimidazo[4,5-c]pyridinylmethyl)phenylsulphonyl-L-leucinol,
85. O-3-(Pyridin-3-yl)propanoyl-N-methyl-N-4-(1H-2-methylimidazo[ 4,5-c]pyridinylmethyl)phenylsulphonyl-L-leucinol,
86. O-(N'-Benzyloxycarbonyl)-L-leucinoyl-N-methyl-N-4-(1H-2-methylimidazo[4,5-c]pyridinylmethyl)phenylsulphonyl-L-leucinol,
87. O-(N',N'-Dibenzyl)-L-leucinoyl-N-methyl-N-4-(1H-2-methylimidazo[ 4,5c]pyridinylmethyl)phenylsulphonyl-L-leucinol,
88. O-(N'-Benzyloxycarbonyl)glycinoyl-N-methyl-N-4-(1H-2-methylimidazo[4,5-c]pyridinylmethyl)phenylsulphonyl-L-leucinol,
89. O-(N'-Benzyloxycarbonyl)-D-leucinoyl-N-methyl-N-4-(1H-2-methylimidazo[4,5-c]pyridinylmethyl)phenylsulphonyl-L-leucinol,
90. O-(N'-Benzyloxycarbonyl)-L-phenylalininoyl-N-methyl-N-4-(1H-2-methylimidazo[4,5-c]pyridinylmethyl)phenylsulphonyl-L-leucinol,
91. O-(N',N'-dibenzyl)glycinoyl-N-methyl-N-4-(1H-2-methylimidazo[ 4,5-c]pyridinylmethyl)phenylsulphonyl-L-leucinol,
92. O-(N'-Benzyloxycarbonyl)-L-norleucinoyl-N-methyl-N-4-(1H-2-methylimidazo[4,5-c]pyridinylmethyl)phenylsulphonyl-L-leucinol,
93. O-(N'-Butoxycarbonyl)-L-leucinoyl-N-methyl-N-4-(1H-2-methylimidazo[4,5-c]pyridinylmethyl)phenylsulphonyl-L-leucinol,
94. O-(N'-Benzyloxycarbonyl)-L-valinoyl-N-methyl-N-4-(1H-2-methylimidazo[4,5-c]pyridinylmethyl)phenylsulphonyl-L-leucinol,
95. O-(N'-Benzyloxycarbonyl)-L-phenylglycinoyl-N-methyl-N-4-(1H-2methylimidazo[4,5-c]pyridinylmethyl)phenylsulphonyl-L-leucinol,
96. O-Diethoxyphosphoryl-N-methyl-N-4-(1H-2-methylimidazo[ 4,5-c]pyridinylmethyl)phenylsulphonyl-L-leucinol,
97. O-Dimethoxyphosphoryl-N-methyl-N-4-(1H-2-methylimidazo[ 4,5-c]pyridinylmethyl)phenylsulphonyl-L-leucinol,
98. O-Diphenoxyphosphoryl-N-methyl-N-4-(1H-2-methylimidazo[ 4,5-c]pyridinylmethyl)phenylsulphonyl-L-leucinol,
99. O-Diisopropoxyphosphoryl-N-methyl-N-4-(1H-2-methylimidazo[ 4,5-c]pyridinylmethyl)phenylsulphonyl-L-leucinol,
100. O-Methylsulphonyl-N-methyl-N-4-(1H-2-methylimidazo[ 4,5-c]pyridinylmethyl)phenylsulphonyl-L-leucinol,
101. O-Ethylsulphonyl-N-methyl-N-4-(1H-2-methylimidazo[ 4,5-c]pyridinylmethyl)phenylsulphonyl-L-leucinol,
102. O-Propylsulphonyl-N-methyl-N-4-(1H-2-methylimidazo[ 4,5-c]pyridinylmethyl)phenylsulphonyl-L-leucinol,
103. O-Phenylsulphonyl-N-methyl-N-4-(1H-2-methylimidazo[ 4,5-c]pyridinylmethyl)phenylsulphonyl-L-leucinol,
104. O-4-Methylphenylsulphonyl-N-methyl-N-4-(1H-2-methylimidazo[ 4,5-c]pyridinylmethyl)phenylsulphonyl-L-leucinol,
105. O-Benzylaminocarbonyl-N-methyl-N-4-(1H-2-methylimidazo[ 4,5-c]pyridinylmethyl)phenylsulphonyl-L-leucinol,
106. O-4-Ethoxycarbonylpiperazinecarbonyl-N-methyl-N-4-(1H-2-methylimidazo[4,5-c]pyridinylmethyl)phenylsulphonyl-L-leucinol,
107. O-5-Ethyl-1,3,4-thiadiazol-2-ylaminocarbonyl-N-methyl-N-4-(1H-2methylimidazo[4,5-c ]pyridinylmethyl)phenylsulphonyl-L-leucinol,
108. O-Pyridin-2-ylmethylaminocarbonyl-N-methyl-N-4-(1H-2-methylimidazo[4,5-c]pyridinylmethyl)phenylsulphonyl-L-leucinol,
109. O-Octadecylaminocarbonyl-N-methyl-N-4-(1H-2-methylimidazo[ 4,5-c]pyridinylmethyl)phenylsulphonyl-L-leucinol,
110. O-Methylaminocarbonyl-N-methyl-N-4-(1H-2-methylimidazo[ 4,5-c]pyridinylmethyl)phenylsulphonyl-L-leucinol,
111. O-Ethylaminocarbonyl-N-methyl-N-4-(1H-2-methylimidazo[ 4,5-c]pyridinylmethyl)phenylsulphonyl-L-leucinol,
112. O-n-Propylaminocarbonyl-N-methyl-N-4-(1H-2-methylimidazo[ 4,5-c]pyridinylmethyl)phenylsulphonyl-L-leucinol,
113. O-i-Propylaminocarbonyl-N-methyl-N-4-(1H-2-methylimidazo[ 4,5-c]pyridinylmethyl)phenylsulphonyl-L-leucinol,
114. O-n-Pentylaminocarbonyl-N-methyl-N-4-(1H-2-methylimidazo[ 4,5-c]pyridinylmethyl)phenylsulphonyl-L-leucinol,
115. O-n-Hexylaminocarbonyl-N-methyl-N-4-(1H-2-methylimidazo[ 4,5-c]pyridinylmethyl)phenylsulphonyl-L-leucinol,
116. O-n-Octylaminocarbonyl-N-methyl-N-4-(1H-2-methylimidazo[ 4,5-c]pyridinylmethyl)phenylsulphonyl-L-leucinol,
117. O-n-Decylaminocarbonyl-N-methyl-N-4-(1H-2-methylimidazo[ 4,5-c]pyridinylmethyl)phenylsulphonyl-L-leucinol,
118. O-n-Dodecylamino carbonyl-N-methyl-N-4-(1H-2-methylimidazo[ 4,5-c]pyridinylmethyl)phenylsulphonyl-L-leucinol,
119. O-n-Tetradecylaminocarbonyl-N-methyl-N-4-(1H-2-methylimidazo[ 4,5-c ]pyridinylmethyl)phenylsulphonyl-L-leucinol,
120. O-n-Hexadecylaminocarbonyl-N-methyl-N-4-(1H-2-methylimidazo[ 4,5-c]pyridinylmethyl)phenylsulphonyl-L-leucinol, 121. O-t-Butylaminocarbonyl-N-methyl-N-4-(1H-2-methylimidazo[ 4,5-c]pyridinylmethyl)phenylsulphonyl-L-leucinol,
122. O-Pyridin-2-ylaminocarbonyl-N-methyl-N-4-(1H-2-methylimidazo[ 4,5-c]pyridinylmethyl)phenylsulphonyl-L-leucinol,
123. O-Pyridin-4-ylmethylaminocarbonyl-N-methyl-N-4-(1H-2-methylimidazo[4,5-c]pyridinylmethyl)phenylsulphonyl-L-leucinol,
124. O-Pyridin-3-ylmethylaminocarbonyl-N-methyl-N-4-(1H-2-methylimidazo[4,5-c]pyridinylmethyl)phenylsulphonyl-L-leucinol,
125. O-4-Methoxyphenylaminocarbonyl-N-methyl-N-4-(1H-2-methylimidazo[4,5-c]pyridinylmethyl)phenylsulphonyl-L-leucinol,
126. O-3,4-Dimethoxybenzylaminocarbonyl-N-methyl-N-4-(1H-2-methylimidazo[4,5-c]pyridinylmethyl)phenylsulphonyl-L-leucinol,
127. O-2-(4-Methoxyphenyl)ethylaminocarbonyl-N-methyl-N-4-(1H-2-methylimidazo[4,5-c]pyridinylmethyl)phenylsulphonyl-L-leucinol,
128. O-2-(3,4-Dimethoxyphenyl)ethylaminocarbonyl-N-methyl-N-4-(1H-2methylimidazo[4,5-c]pyridinylmethyl)phenylsulphonyl-L-leucinol,
129. O-3-(3,4-Dimethoxyphenyl)propylaminocarbonyl-N-methyl-N-4-(1H-2methylimidazo[4,5-c]pyridinylmethyl)phenylsulphonyl-L-leucinol,
130. O-3-(Pyridin-3-yl)propylaminocarbonyl-N-methyl-N-4-(1H-2-methylimidazo[4,5-c]pyridinylmethyl)phenylsulphonyl-L-leucinol,
131. N-Methy1-N-4-(1H-2-methylimidazo[ 4,5-c]pyridinylmethyl)phenylsulphonyl-2-thienylmethylamine,
132. N-Methyl-N-4-(1H-2-methylimidazo[4,5-c]pyridinylmethyl)phenylsulphonyltetrahydrofurfurylamine,
133. N-4-(1H-2- Methylimidazo[4,5-c]pyridinylmethyl)phenylsulphonyl-2-(N'-methylpyrrol-2-yl)ethylamine,
134. N-Methyl-N-4-(1H-2-methylimidazo[4,5-c]pyridinylmethyl)phenylsulphonyl-1-( 4-fluorophenyl)-1-(2-thienyl)methylamine,
135. N-4-(1H-2-Methylimidazo[4,5-c]pyridinylmethyl)phenylsulphonyl-1-(2thienyl)propylamine,
136. N-Methyl-N-4-(1H-2-methylimidazo[4,5-c]pyridinylmethyl)phenylsulphonyl-1-(2-furyl)- 3-methylbutylamine,
137. N-4-(1H-2-Methylbenzimidazolylmethyl)phenylsulphonyl-1-(2-benzothiazolyl)- 3-methylbutylamine,
138. N-Methyl-N-4-(1H-2-methylimidazo[4,5-c]pyridinylmethyl)phenylsulphonyl-1-( 2-thienyl)-3-methylbutylamine,
139. N-Methyl-N-4-(1H-2-methylimidazo[4,5-c]pyridinylmethyl)phenylsulphonyl-1-(pyridin- 3-yl)-3-methylbutylamine,
140. N-Methyl-N-4-(1H-2-methylimidazo[4,5-c]pyridinylmethyl)phenylsulphonyl-1-(N'-methyl- 2-pyrrolyl)-3-methylbutylamine,
141. N-Methyl-N-4-(1H-2-methylimidazo[4,5-c]pyridinylmethyl)phenylsulphonyl-1-(pyrazin- 2-yl)-3-methylbutylamine,
142. N-Methyl-N-4-(1H-2-methylimidazo[4,5-c]pyridinylmethyl)phenylsulphonyl-1-( 6-methylpyrazin-2-yl)-3-methylbutylamine,
143. N-Methyl-N-4-(1H-2-methylimidazo[4,5-c]pyridinylmethyl)phenylsulphonyl-1-( 6-ethylpyrazin-2-yl )-3-methylbutylamine,
144. N-Methyl-N-4-(1H-2-methylimidazo[4,5-c]pyridinylmethyl)phenylsulphonyl-1-(6-ethyl- 1,2-pyridazin-3-yl)-3-methylbutylamine,
145. N-Methyl-N-4-(1H-2-methylimidazo[4,5-c]pyridinylmethyl)phenylsulphonyl-1-(2-ethyl- 1,3-pyrimidin-5-yl)-3-methylbutylamine
146. N-Methyl-N-4-(1H-2-methylimidazo[4,5-c]pyridinylmethyl)phenylsulphonyl-1-( 1,3-dithian-2-yl)-3-methylbutylamine,
147. N-Methyl-N-4-(1H-2-methylimidazo[4,5-c]pyridinylmethyl)phenylsulphonyl-1-( 2-thienyl)pentylamine,
148. N-Methyl-N-4-(1H-2-methylimidazo[4,5-c]pyridinylmethyl)phenylsulphonyl-1-( 4-fluorophenyl)-1-(2-furyl)methylamine,
149. N-Methyl-N-4-(1H-2-methylimidazo[4,5-c]pyridinylmethyl)phenylsulphonyl-2-( 4-methoxyphenyl)-1-(2-furyl)ethylamine,
150. N-Methyl-N-4-(1H-2-methylimidazo[4,5-c]pyridinylmethyl)phenylsulphonyl-1-(pyridin- 2-yl)-3-methylbutylamine,
151. N-Methyl-N-4-(1H-2-methylimidazo[4,5-c]pyridinylmethyl)phenylsulphonyl-1-( 2-methoxypyridin-3-yl)-3-methylbutylamine,
152. N-Methyl-N-4-(1H-2-methylimidazo[4,5-c]pyridinylmethyl)phenylsulphonyl-1-(pyridin-3-ylmethyl)-3-methylbutylamine,
153. N-Methyl-N-4-(1H-2-methylimidazo[4,5-c]pyridinylmethyl)phenylsulphonyl-1-( 2-benzo[b ]thienyl)-3-methylbutylamine,
154. N-Methyl-N-4-(1H-2-methylimidazo[4,5-c]pyridinylmethyl)phenylsulphonyl-1-( 3-methylisoxazol-5-ylmethyl)-3-methylbutylamine,
155. N-Methyl-N-4-(1H-2-methylbenzimidazolylmethyl)phenylsulphonyl-1-(3-methyl-1,2,4-oxadiazol-5-yl)-3-methylbutylamine,
156. N-Methyl-N-4-(1H-2-methylimidazo[4,5-c]pyridinylmethyl)phenylsulphonyl-1-( 3-ethyl-1,2,4-oxadiazol-5-yl)-3-methylbutylamine,
157. N-Methyl-N-4-(1H-2-methylimidazo[4,5-c]pyridinylmethyl)phenylsulphonyl-1-( 3-hexadecyl-1,2,4-oxadiazol-5-yl)-3-methylbutylamine,
158. N-Methyl-N-4-(1H-2-methylimidazo[4,5-c]pyridinylmethyl)phenylsulphonyl-1-( 3-propyl-1,2,4-oxadiazol-5-yl)-3-methylbutylamine,
159. N-Methyl-N-4-(1H-2-methylimidazo[4,5-c]pyridinylmethyl)phenylsulphonyl-1-( 3-n-butyl-1,2,4-oxadiazol-5-yl)-3-methylbutylamine,
160. N-Methyl-N-4-(1H-2-methylimidazo[4,5-c]pyridinylmethyl)phenylsulphonyl-1-( 3-phenyl-1,2,4-oxadiazol-5-yl)-3-methylbutylamine,
161. N-Methyl-N-4-(1H-2-methylimidazo[4,5-c]pyridinylmethyl)phenylsulphonyl-1-( 3-benzyl-1,2,4-oxadiazol-5-yl)-3-methylbutylamine,
162. N-Methyl-N-4-(1H-2-methylimidazo[4,5-c ]pyridinylmethyl)phenylsulphonyl-1-( 5-methyl-1,3,4-oxadiazol-2-yl)-3-methylbutylamine,
163. N-Methyl-N-4-(1H-2-methylimidazo[4,5-c]pyridinylmethyl)phenylsulphonyl-1-( 5-ethyl-1,3,4-oxadiazol-2-yl)-3-methylbutylamine,
164. N-Methyl-N-4-(1H-2-methylimidazo[4,5-c]pyridinylmethyl)phenylsulphonyl-1-( 5-propyl-1,3,4-oxadiazol-2-yl)-3-methylbutylamine,
165. N-Methyl-N-4-(1H-2-methylimidazo[4,5-c]pyridinylmethyl)phenylsulphonyl-1-( 5-phenyl-1,3,4-oxadiazol-2-yl)-3-methylbutylamine,
166. N-Methyl-N-4-(1H-2-methylimidazo[4,5-c]pyridinylmethyl)phenylsulphonyl-13-alanine ethyl ester,
167. N-Methyl-N-4-(1H-2-methylimidazo[4,5-c]pyridinylmethyl)phenylsulphonyl-3-amino- 5-methylhexanoic acid ethyl ester, 168. N-Methyl-N-4-(1H-2-methylimidazo[4,5-c]pyridinyl-methyl)phenylsulphonyl-3-amino- 5-methylhexanoic acid isopropyl ester,
169. N-Methyl-N-4-(1H-2-methylimidazo[4,5-c]pyridinyl-methyl)phenylsulphonyl-3-amino- 5-methylhexanoic acid n-butyl ester,
170. N-Methyl-N-4-(1H-2-methylimidazo[4,5-c]pyridinyl-methyl)phenylsulphonyl-3-amino- 5-methylhexanoic acid benzyl ester,
171. N-Methyl-N-4-(1H-2-methylimidazo[4,5-c]pyridinyl-methyl)phenylsulphonyl-3-amino- 4-phenylbutanoic acid ethyl ester,
172. N-Methyl-N-4-(1H-2-methylimidazo[4,5-c]pyridinyl-methyl)phenylsulphonyl-3-amino-4-( 4-methoxyphenyl)butanoic acid ethyl ester.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating an imidazole derivative represented by general formula II

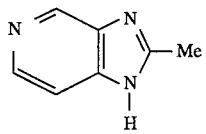

II with a suitable base (e.g. sodium hydride, potassium hydride, sodium bis(trimethylsilyl)amide, or potassium hydroxide), followed by a compound of general formula III

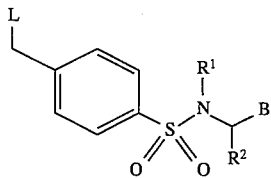

III wherein $R^1$, $R^2$ and B are as defined in general formula I, and L is chloro, bromo, iodo, methanesulphonyloxy, p-toluenesulphonyloxy or trifluoromethanesulphonyloxy; or (b) treating a substituted diamino compound of general formula IV

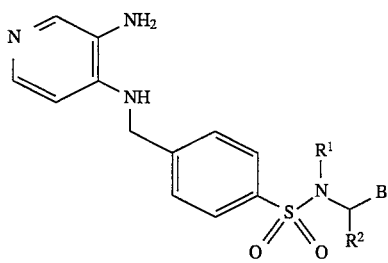

IV wherein $R^1$, $R^2$ and B are as defined in general formula I, with acetic acid or a suitable derivative thereof; or (c) treating a sulphonamide of general formula V

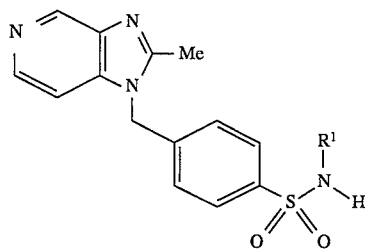

V wherein $R^1$ is as defined in general formula I, with a compound of general formula VI

VI wherein $R^2$ and B are as defined in general formula I and L' is hydroxyl, chloro, bromo, iodo, methanesulphonyloxy, p-toluenesulphonyloxy or trifluoromethanesulphonyloxy; and (d) optionally after step (a), step (b) or step (c) converting, in one or a plurality of steps, a compound of general formula I into another compound of general formula I.

The reaction of step (a) can for preference be conducted in an aprotic solvent (e.g. tetrahydrofuran, N,N-dimethylformamide or acetonitrile) to yield compounds of general formula I. In the case where an unsymmetrically substituted imidazole derivative is used the reaction can yield an isomeric mixture, which is separated by chromatography to yield compounds of general formula I.

In step (b), derivatives of acetic acid, which are suitable substrates for the reaction include acetyl halides of general formula VII $$MeCO_2X \qquad \text{VII}$$

wherein X is fluoride, chloride, bromide or iodide; trialkylorthoesters of general formula VIII

VIII wherein $R^7$ is $—C_1–C_6$ alkyl; imino ether salts of general formula IX

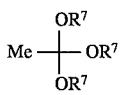

IX wherein $R^7$ and X are as defined above, or acetic anhydride. Acetyl halides of general formula VII, trialkylorthoesters of general formula VIII and imino ether salts of general formula IX are available in the art or can be prepared by methods analogous to those known in the art The reaction of step (c) can be conducted in the presence of triphenylphosphine and diethyl azodicarboxylate in an aprotic solvent (e.g. tetrahydrofuran) when L' is hydroxyl and in the presence of a base (e.g. sodium hydride, potassium hydride, sodium bis(trimethylsilyl)amide, or potassium hydroxide) in an aprotic solvent (e.g. tetrahydrofuran) when L' is chloro, bromo, iodo, methanesulphonyloxy, p-toluenesulphonyloxy or trifluoromethanesulphonyloxy.

By means of step (d) certain compounds of general formula I wherein B is as defined in general formula I but is not a $—CH_2OC(=O)NHR^6$ or $—NHC(C=O)OR^6$ group, may be prepared by treatment of a compound of general formula I wherein $R^2$ is hydrogen with base followed by an electrophile of general formula X LR²  X wherein R² is as defined in general formula I but is not a hydrogen atom, a phenyl or a substituted phenyl group, and L is chloro, bromo, iodo, methanesulphonyloxy, p-toluenesulphonyloxy or trifluoromethanesulphonyloxy. Electrophiles of general formula X are available in the art or can be prepared by procedures known to those skilled in the art.

Also by means of step (d) certain compounds of general formula I wherein B is a —CH₂OC(=O)R⁶ group may be prepared by treatment of a compound of general formula I wherein B is a —CH₂OH group with a suitable carboxylic acid derivative of general formula XI R⁶C(=O)Q  XI wherein R⁶ is as defined in general formula I and Q is a hydrogen atom, halide or a —(O=)CR⁶ group. The conditions for this reaction will depend on the nature of the group Q and will be apparent to one skilled in the art. The reaction will usually be carried out in the presence of a suitable base (e.g. triethylamine, pyridine and/or 4-dimethylaminopyridine) in an aprotic solvent (e.g. tetrahydrofuran or dichloromethane). Carboxylic acid derivatives of the general formula XI are available in the art or can be prepared by methods analogous to those known in the art.

Also by means of step (d) certain compounds of general formula I wherein B is a —CH₂OSO₂R⁶ group may be prepared by treatment of a compound of general formula I wherein B is a —CH₂OH group with a suitable sulphonyl halide of general formula XII R⁶SO₂Hal  XII wherein R⁶ is as defined in general formula I and Hal is fluoro, chloro, bromo or iodo, in the presence of a suitable base (e.g. triethylamine) in an aprotic solvent (e.g. tetrahydrofuran or dichloromethane). Sulphonyl halides of general formula XII are available in the art or can be prepared by methods analogous to those known in the art.

Also by means of step (d) certain compounds of general formula I wherein B is a —CH₂OP(=O)OR⁶OR⁶ group may be prepared by treatment of a compound of general formula I wherein B is a —CH₂OH group with a suitable halophosphate of general formula XIII R⁶OR⁶OP(=O)Hal XIII wherein R⁶ is as defined in general I formula I and Hal is fluoro, chloro, bromo or iodo, in the presence of a suitable base (e.g. triethylamine) in an aprotic solvent (e.g. tetrahydrofuran or dichloromethane). Halophosphates of general formula XIII are available in the art or can be prepared by methods analogous to those known in the art.

Also by means of step (d) certain compounds of general formula I wherein B is a —CH₂OC(=O)NHR⁶ group may be prepared by treatment of a compound of general formula I wherein B is a —CH₂OH group with an isocyanate of general formula XIV R⁶—N=C=O 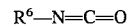 XIV wherein R⁶ is as defined in general formula I. Isocyanates of general formula XIV are available in the art or can be prepared by methods analogous to those known in the art.

Also by means of step (d) certain compounds of general formula I wherein B is a —CH₂OC(=O)NHR⁶ group may be prepared by a two step process involving initial treatment of a compound of general formula I wherein B is a —CH₂OH group with a reagent of general formula XV

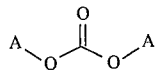 XV wherein A is a pyridin-2-yl or N-succinimidyl group, in the presence of a suitable base (e.g. triethylamine) in an aprotic solvent (e.g. dichloromethane) to give an anhydride of general formula XVI

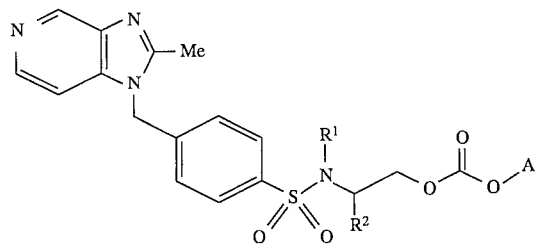 XVI wherein R¹ and R² are as defined in general formula I and A is as defined above, and subsequent treatment of the anhydride of general formula XVI with an amine of general formula XVII R⁶NH₂  XVII wherein R⁶ is as defined in general formula I. Each step is for preference conducted in an aprotic solvent (e.g. dichloromethane). Reagents of general formula XV are available in the art or can be prepared by methods analogous to those known in the art. Amines of general formula XVII are available in the art or can be prepared by methods analogous to those known in the art.

Also by means of step (d) certain compounds of general formula I wherein B is a —CH₂OH group may be prepared by the reduction of a compound of general formula. I wherein B is a —CH₂OC(=O)R⁶ or —CO₂R⁶ group with a suitable hydride reducing reagent (e.g. lithium aluminium hydride or diisobutylaluminium hydride) in an aprotic solvent (e.g. tetrahydrofuran or toluene).

Also by means of step (d) certain compounds of general formula I wherein B is a 1,2,4-oxadiazol-5-yl group may be prepared by treatment of a compound of general formula I wherein B is a —CO₂H group with pentafluorophenol and a coupling agent such as N-(3-dimethylaminopropyl)-N'-ethylcarbodiimide in a solvent such as dichloromethane. The resulting pentafluorophenyl ester is treated with an amide oxime of general formula XVIII

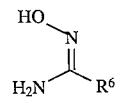 XVIII wherein R⁶ is as defined in general formula I in a suitable aprotic solvent (e.g. chloroform), followed by cyclisation under Dean-Stark conditions in suitable solvent (e.g. xylene, toluene, benzene or ethyl acetate). The cyclisation may be aided by the addition of activated molecular sieves. Amide oximes of general formula XVIII are known in the art or may be prepared by methods analogous to those known in the art.

Also by means of step (d) certain compounds of general formula I wherein B is a 1,2,4-oxadiazol-5-yl group may be prepared by treatment of a compound of general formula I wherein B is a —CO₂NH₂ group, with a derivative R⁵C(OR⁸)₂N(R⁹)₂ wherein R⁵ is as defined in general formula I and R⁸ and R⁹ are independently —C₁-C₆ alkyl followed by hydroxylamine under dehydrating conditions such as heating in acetic acid with a co-solvent (e.g. dioxane). Compounds of general formula I wherein B is a —$CO_2NH_2$ group may be obtained by treatment of a compound of general formula I wherein B is a —$CO_2R^6$, wherein $R^6$ is as defined in general formula I, with ammonia. Derivatives $R^5C(OR^8)_2N(R^9)_2$ are known in the art or may be prepared by methods analogous to those known in the art.

Also by means of step (d) certain compounds of general formula I wherein B is a 1,2,4-oxadiazol-3-yl group may be prepared by treatment of a compound of general formula I wherein B is a —CN group with hydroxylamine followed by heating with a carboxylic acid derivative of general formula $R^5C(=O)Q$, $R^5C(=NH)R^7$ or $R^5C(-OR^7)_3$ wherein $R^5$ is as defined in general formula I, Q is a halide, 4-nitrophenoxy or —(O=)$CR^5$ group, and $R^7$ is as defined above. Compounds of general formula I wherein B is a —CN group may be obtained by dehydration of a compound of general formula I wherein B is a —$CO_2NH_2$. Carboxylic acid derivatives of general formula $R^5C(=O)Q$, $R^5C(=NH)R^7$ or $R^5C(OR^7)_3$ are known in the art or may be prepared by methods analogous to those known in the art.

Also by means of step (d) certain compounds of general formula I wherein B is a 1,3,4-oxadiazol-2-yl group may be prepared by treatment of a compound of general formula I wherein B is a —$CO_2Q$ group, wherein Q is a halide, 4-nitrophenoxy, pentafluorophenoxy, —$OC_1$-$C_6$ alkyl or —(O=)$CC_1$-$C_6$ alkyl group, with hydrazine followed by a carboxylic acid derivative of general formula $R^5C(=O)Q$, $R^5C(=NH)R^7$ or $R^5C(OR^7)_3$, wherein $R^5$ is as defined in general formula I, Q is a halide, 4-nitrophenoxy, pentafluorophenoxy or —(O=)$CR^5$ group, and $R^7$ is as defined above, with heating.

Imidazole derivatives of general formula II are available in the art or can be prepared by methods analogous to those known in the art.

Compounds of general formula III may be prepared by treatment of an amine of general formula XIX

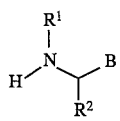

XIX wherein $R^1$, $R^2$ and B are as defined in general formula I, with a sulphonyl halide of general formula XX

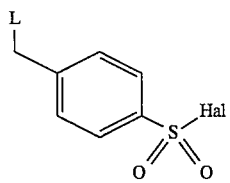

XX wherein L is chloro, bromo, iodo, methanesulphonyloxy, p-toluenesulphonyloxy or trifluoromethanesulphonyloxy and Hal is a halide (e.g. fluoro, chloro or bromo), in the presence of a suitable base (e.g. triethylamine) in a suitable aprotic solvent (e.g. dichloromethane, tetrahydrofuran, ethyl acetate or dioxan). Amines of general formula XIX and sulphonyl halides of general formula XX are known in the art or may be prepared by methods known in the art.

Alternatively compounds of general formula III may be prepared by the treatment of a sulphonamide of general formula XXI

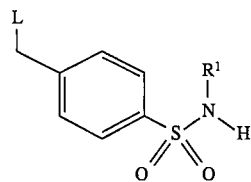

XXI wherein $R^1$ is as defined in general formula I, with a compound of general formula VI in the presence of triphenylphosphine and diethyl azodicarboxylate in an aprotic solvent (e.g. tetrahydrofuran) when L' is hydroxyl and in the presence of a base (e.g. sodium hydride, potassium hydride, sodium bis(trimethylsilyl)amide, or potassium hydroxide) in an aprotic solvent (e.g. tetrahydrofuran) when L' is chloro, bromo, iodo, methanesulphonyloxy, p-toluenesulphonyloxy or trifluoromethanesulphonyloxy. Sulphonamides of general formula XXI and alcohols of general formula VI are known in the art or may be prepared by methods known in the art.

Substituted 1,2-diamines of general formula IV may be prepared by the reduction of a substituted 1,2-nitroamine of general formula XXII

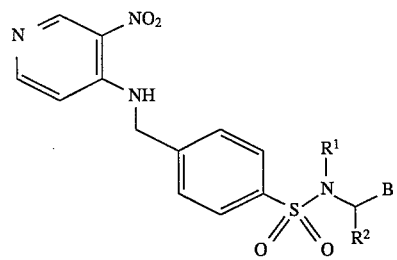

XXII wherein $R^1$, $R^2$ and B are as defined in general formula I, for example in the presence of hydrogen and a catalyst such as palladium or platinum.

Substituted 1,2-nitroamines of general formula XXII may be prepared by a number of methods. The first of these methods involves the treatment of a nitro compound of general formula XXIII

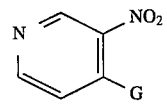

XXIII wherein G is halo or —$OC_1$-$C_6$ alkyl, is treated with an amino compound of general formula XXIV

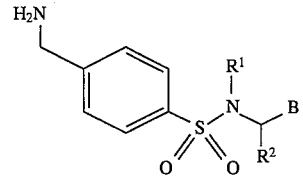

XXIV wherein $R^1$, $R^2$ and B are as defined in general formula I. Nitro compounds of general formula XXIII are available in the art or can be prepared by methods analogous to those known in the art. Amino compounds of general formula XXIV can be prepared by treatment of a compound of general formula III with hexamethylenetetramine followed by treatment with ethanolic hydrochloric acid or by sequential treatment of a compound of general formula III with sodium azide followed by either triphenylphosphine in 'wet' tetrahydrofuran or hydrogenation over a suitable catalyst.

A second procedure for the preparation of substituted 1,2-nitroamines of general formula XXII involves the reduction of an imino nitro compound of general formula XXV

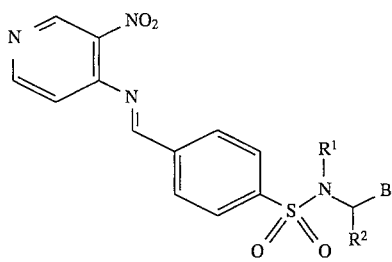

XXV wherein $R^1$, $R^2$ and B are as defined in general formula I, for example by the action of sodium cyanoborohydride.

The imino nitro compounds of general formula XXV may be prepared by treating a 1,2-nitroamine of formula XXVI

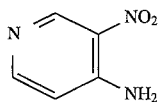

XXVI with a substituted carbonyl derivative of general formula XXVII

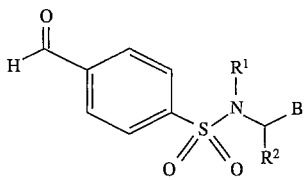

XXVII wherein $R^1$, $R^2$ and B are as defined in general formula I. The 1,2-nitroamine of formula XXVI is available in the art or can be prepared by methods analogous to those known in the art. Substituted carbonyl derivatives of general formula XXVII may be prepared by treatment of a compound of general formula III with an oxidising agent (e.g. dimethyl sulphoxide), or by treatment of a compound of general formula III with hexamethylenetetramine in aqueous ethanol.

Alternatively substituted 1,2-nitroamines of general formula XXII may be prepared by the reduction of a 1,2-nitroamide of general formula XXVIII

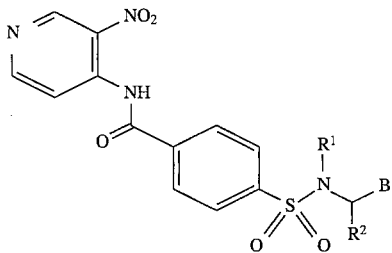

XXVIII wherein $R^1$, $R^2$ and B are as defined in general formula I, with a suitable metal hydride reducing agent such as for example lithium aluminium hydride.

The 1,2-nitroamides of general formula XXVIII may be prepared by the coupling of a 1,2-nitroamine of formula XXVI with an acid chloride of general formula XXIX

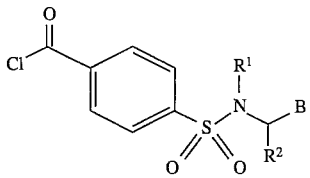

XXIX wherein $R^1$, $R^2$ and B are as defined in general formula I, in an aprotic solvent and in the presence of a suitable base such as, for example, triethylamine. Alternatively, the reaction may be conducted utilising an acid anhydride of general formula XXX

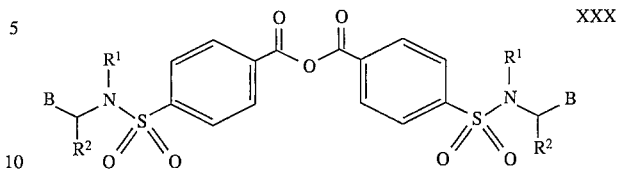

XXX wherein $R^1$, $R^2$ and B are as defined in general formula I. Another procedure for preparing 1,2-nitroamides of general formula XXVII involves reaction of a 1,2-nitroamine of formula XXVI with a carboxylic acid of general formula XXXI

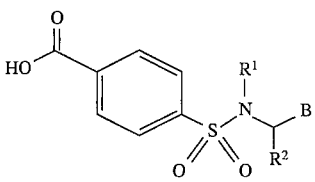

XXXI wherein $R^1$, $R^2$ and B are as defined in general formula I, in the presence of a coupling reagent (e.g. 1,3-dicyclohexyl-carbodiimide). Acid chlorides of general formula XXIX, acid anhydrides of general formula XXX and carboxylic acids of general formula XXXI may be prepared from carbonyl derivatives of general formula XXVII by procedures known to those skilled in the art.

Sulphonamides of general formula V may be prepared by methods analogous to those described in steps (a) and (b) above for the preparation of compounds of general formula I.

The appropriate solvents employed in the above reactions are solvents wherein the reactants are soluble but do not react with the reactants. The preferred solvents vary from reaction to reaction and are readily ascertained by one of ordinary skill in the art.

Compounds of general formulae III, IV and V are valuable intermediates in the preparation of compounds of general formula I, as are other novel compounds specifically or generically disclosed herein. According to a third aspect of the invention, there is therefore provided a compound of general formula III. According to a fourth aspect of the invention, there is provided a compound of general formula IV. According to a fifth aspect of the invention, there is provided a compound of general formula V.

This invention also relates to a method of treatment for patients (or animals including mammalian animals raised in the dairy, meat, or fur trades or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a sixth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an seventh aspect of the invention there is provided the use of a compound of general formula I in the preparation of an agent for the treatment or prophylaxis of PAF-mediated diseases, and/or the treatment of inflammatory disorders; such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a eighth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or nonaqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid nonionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula I exhibit in vitro and in vivo antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Pharmacological Example 1. The ability of compounds of general formula I to reverse the hypotension caused by an infusion of PAF in rats was measured according to Pharmacology Example 2.

The following examples illustrate the invention, but are not intended to limit the scope in any way.

The following abbreviations have been used in the Examples:

DCM—Dichloromethane
DIPE—Diisopropylether
DMF—N,N-Dimethylformamide
HPLC—High performance liquid chromatography
NBS—N-Bromosuccinimide
TDA-1—Tris(2-(2-methoxyethoxy)ethyl)amine
THF—Tetrahydrofuran
TLC—Thin layer chromatography Column chromatography was performed with "flash" grade silica gel. Unless otherwise stated anhydrous magnesium sulphate or anhydrous sodium sulphate was used for drying organic solutions. Unless otherwise stated $^1$H NMR and $^{13}$C NMR spectra were recorded on a Bruker AC-250 spectrometer at 250 MHz and 62.9 MHz respectively using CDCl$_3$ as a solvent and internal reference and are reported as δ ppm from TMS.

EXAMPLE 1

N-Methyl-N-4-(1H-2-methylimidazo[4,5-c]pyridinylmethyl)phenylsulphonyl-L-leucinol

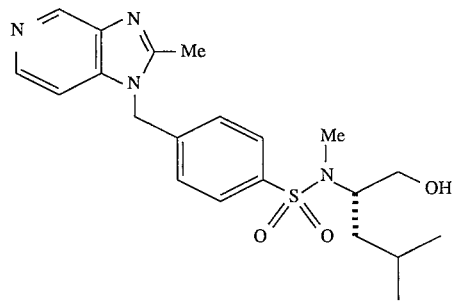

(a) 4-Bromomethylphenylsulphonylchloride

To a solution of p-toluenesulphonyl chloride (50 g, 0.26 mol) in benzene (150 ml) and NBS (46.7 g, 0.26 tool) heated at reflux was added 2,2'-azobis(2-methylpropionitrile) (100 mg). The mixture was heated at reflux for 12 h and allowed to cool to room temperature. The white precipitate of succinimide that formed was separated and discarded. The filtrate was taken up in DCM (200 ml) and washed with water (3×100 ml) followed by brine (100 ml) and dried. Filtration, concentration and subsequent crystallisation (from DIPE) gave in two crops 4-bromomethylphenylsulphonylchloride (46.3 g, 66%) as a white crystalline solid.

m.p. 75°–76° C.

$\delta_H$ 8.02 (2H, d, J 8.5 Hz), 7.64 (2H, d, J 8.5 Hz), 4.52 (2H, s).

(b) N-4-Bromomethylphenylsulphonyl-L-leucine ethyl ester

L-leucine ethyl ester hydrochloride (75.0 g. 0.403 mol) was suspended in THF (300 ml) at 0° C., and triethylamine (67 ml, 0.484 mol) added slowly. After stirring for 15 mins a solution of 4-bromomethylphenylsulphonyl chloride (108.4 g, 0.403 mol) in THF (100 ml) was added via cannular. The reaction mixture was allowed to stir overnight at ambient temperature. The solvent was removed under low pressure and the organics were extracted into ethyl acetate (200 ml) and washed with water (100 ml) and brine (100 ml). The organic portion was dried, filtered and the solvent evaporated under low pressure. The product was recrystallised from DIPE (500 ml) to give N-4-bromomethylphenylsulphonyl-L-leucine ethyl ester (134.0 g, 85%) as a white crystalline solid.

$\delta_H$ 7.84 (2H, d, J 8.3 Hz), 7.52 (2H, d, J 8.3 Hz), 5.06 (1H, d, J 10.1 Hz), (2H, s), 3.97–3.82 (3H, m), 1.85–1.79 (1H, m), 1.49 (2H, t, J 7.1 Hz), 1.08 t, J 7.1 Hz), 0.92 (3H, d, J 6.7 Hz), 0.91 (3H, d, J 6.5 Hz).

(c) N-4-Azidomethylphenylsulphonyl-L-leucine ethyl ester

A solution of sodium azide (75.0 g, 1.054 mol) in water (150 ml) was added to a solution of the N-4-bromomethylphenylsulphonyl-L-leucine ethyl ester (89.0 g, 0.221 mol) in dichloromethane (150 ml). Benzyltriethylammonium chloride (10 g, 0.044 mol) was added and the heterogeneous reaction mixture stirred vigorously for 60 h. The organic portion was separated, washed thoroughly with water, dried, filtered and concentrated to a golden oil, which crystallised on standing. The resulting white solid was freeze dried overnight to yield N-4-azidomethylphenylsulphonyl-L-leucine ethyl ester (78.2 g, 97%).

m.p. 75°–77° C.

Analysis calculated for $C_{15}H_{22}N_4O_4S$ Requires C 50.83H 6.26N 15.81 Found C 50.80H 6.28N 15.82 i.r. (DCM) 2930, 2100, 1730, 1335, 1150 cm$^{-1}$ $[\alpha]_D^{25}$ –16.4 (c 2.0, DCM)

$\delta_H$ 7.86 (2H, d, J 8.4 Hz), 7.45 (2H, d, J 8.6 Hz), 5.13, (1H, d, J 10.0 Hz), 4.43 (2H, s), 3.98–3.84 (3H, m), 1.83–1.75 (1H, m), 1.49 (2H, dd, J 7.7, 6.7 Hz), 1.09 (3H, t, J 7.1 Hz), 0.91 (3H, d, J 6.7 Hz), 0.89 (3H, d, J 6.5 Hz).

(d) N-Methyl-N-4-azidomethylphenylsulphonyl-L-leucine ethyl ester

A 60% dispersion of sodium hydride in mineral oil (9.68 g, 0.242 mol) was added in portions to a solution of N-4-azidomethylphenylsulphonyl-L-leucine ethyl ester (78.0 g, 0.220 mol) in THF (200 ml) at 0° C. After stirring for 20 mins iodomethane (28 ml, 0.44 mol) was added slowly, and the reaction allowed to warm to ambient temperature overnight. Saturated ammonium chloride solution (ca. 15 ml) was added and the THF removed under reduced pressure. The resulting residue was taken up in dichloromethane, washed with saturated hydrogen carbonate solution then water, dried, filtered and concentrated to give N-methyl-N-4-azidomethylphenylsulphonyl-L-leucine ethyl ester as an orange oil (76.0 g, 94%).

Analysis calculated for $C_{16}H_{24}N_4O_4S$ Requires C 52.16H 6.57N 15.21 Found C 52.20H 6.54N 15.12 i.r. (DCM) 2100, 1735, 1340, 1160 cm$^{-1}$ $[\alpha]_D^{20}$ –15.3 (c 2.2, DCM)

$\delta_H$ 7.83 (2H, dd, J 8.2, 1.6 Hz), 7.45 (2H, br d, J 8.3 Hz), 4.71–4.65 (1H, m), 4.44 (2H, s), 3.96–3.86 (2H, m), 2.86 (3H, s), 1.67–1.58 (3H, m), 1.09 ( 3H, t, J 7.1 Hz), 0.99 (3H, d, J 5.0 Hz), 0.97 (3H, d, J 6.1 Hz).

(e) N-Methyl-N-4-aminomethylphenylsulphonyl-L-leucine ethyl ester

Triphenylphosphine (101.80 g, 0.388 mol) was added to a solution of N-methyl-N-4-azidomethylphenylsulphonyl-L-leucine ethyl ester (71.5 g, 0.194 mol) in a mixture of THF and water (4:1, 200 ml), and the reaction mixture stirred overnight at ambient temperature. The THF was removed under reduced pressure, and the product extracted with ethyl acetate, dried, filtered and concentrated to an orange oil. This was purified by chromatography (silica: gradient elution; 1:2 ethyl acetate/hexane; ethyl acetate; 10% methanol in ethyl acetate) to give N-methyl-N-4-aminomethylphenylsulphonyl-L-leucine ethyl ester (38 g, 58%) as a yellow oil.

$\delta_H$ 7.76 (2H, dd, J 8.5, 1.7 Hz), 7.45 (2H, d, J 8.3 Hz), 4.71–4.65 (1H, m), 3.95 (2H, s), 3.95–3.85 (2H, m), 2.83 (3H, s), 1.95 (2H, br s), 1.68–1.57 (3H, m), 1.06 (3H, t, J 7.1 Hz), 0.97 (3H, d, J 5.4 Hz), 0.95 (3H, d, J 5.9 Hz).

(f) N-Methyl-N-4-(N'-3-nitropyridin-4-yl)aminomethylphenylsulphonyl-L-leucine ethyl ester 4-Chloro-3-nitropyridine (6.0 g, 38 mmol) was added to a stirred solution of N-methyl-N-4-aminomethylphenylsulphonyl-L-leucine ethyl ester (13.0 g, 38 mmol) and triethylamine (5.3 ml, 38 mmol) in chloroform (150 ml) at ambient temperature. The reaction mixture was stirred for 60 h, then washed with water, dried, filtered and the solvent removed under reduced pressure to leave a brown oil. This was purified by chromatography over silica (gradient elution; 33% ethyl acetate in hexane; ethyl acetate) to give N-methyl-N-4-(N'-3-nitropyridin- 4-yl)aminomethyl-phenylsulphonyl-L-leucine ethyl ester (10.9 g, 62%) as a yellow-amorphous solid.

m.p. 71°–75° C.

i.r. (DCM) 3390, 1730, 1510, 1330 cm$^{-1}$ $[\alpha]_D^{25}$ –13.8 (c 2.0, DCM)

$\delta_H$ 9.00 (1H, s) 8.55 (1H, t, J 5.9 Hz), 8.04 (1H, d, J 6.1 Hz), 7.60 ( 2H, d, J 8.3 Hz), 7.32 (2H, d, J 8.3 Hz), 6.50 (1H, d, J 6.2 Hz), 4.57 (2H, d, J 5.9 Hz), 4.50–4.44 (1H, m), 3.75–3.62 (2H, m), 2.69 (3H, s), 1.45 (3H, br d), 0.86 (3H, t, J 7.1 Hz) 0.77 (6H, d, J 5.9 Hz).

(g)   N-Methyl-N-4-(N'-3-aminopyridin-4-yl)aminomethylphenylsulphonyl-L-leucine ethyl ester A solution of N-methyl-N-4-(N'-3-nitropyridin-4-yl)aminomethylphenylsulphonyl-L-leucine ethyl ester (10.9 g, 0.023 mol) in ethanol (40 ml) was hydrogenated at 100 p.s.i. overnight in the presence of 10% palladium on charcoal (1.0 g). The catalyst was removed by filtration through GF/F filter paper, and the filtrate evaporated under reduced pressure to give N-methyl-N-4-(N'-3-aminopyridin- 4-yl)aminomethylphenylsulphonyl-L-leucine ethyl ester (8.90 g, 87%) as a brown foam.

$\delta_H$ 7.86 (1H, s) 7.83 (1H, d, J 5.5 Hz), 7.73 (2H, d, J 8.3 Hz), 7.41 (2H, d, J 8.3 Hz), 6.29 (1H, d, J 5.4 Hz), 5.09–4.97 (1H, m), 4.67–4.61 (1H, m), 4.44 (2H, d, J 5.6 Hz), 3.90–3.81 (2H, m), 2.84 (3H, s), 1.62–1.57 (5H, m), 1.04 (3H, t Hz), 0.96 (3H, d, J 6.0 Hz), 0.95 (3H, d, J 6.1 Hz).

(h) N-Methyl-N-4-(1H-2-methylimidazo[4,5-c]pyridinylmethyl)phenylsulphonyl-L-leucine ethyl ester N-Methyl-N-4-(N'-3-aminopyridin-4-yl)aminomethylphenylsulphonyl-L-leucine ethyl ester (8.90 g, 20.5 mmol) was refluxed overnight in acetic anhydride (90 ml). The reaction mixture was allowed to cool, then methanol added cautiously until effervescence ceased. The volatiles were removed under reduced pressure and the residue partitioned between saturated sodium hydrogen carbonate solution and ethyl acetate. The organic portion was washed with saturated sodium hydrogen carbonate (×3), and water, dried, filtered and concentrated to a brown oil. This was passed down a pad of silica (3% methanol in DCM) to remove baseline material, and the product further purified by medium pressure liquid chromatography (silica gel: 3% methanol in DCM plus trace of triethylamine) to give a pale yellow oil (5.12 g, 55%), which solidified slowly on standing. Recrystallisation from ethyl acetate/DIPE gave N-methyl-N-4-(1H-2-methylimidazo[ 4,5-c]pyridinylmethyl)phenylsulphonyl-L-leucine ethyl ester as a white crystalline solid.

m.p. 105° C.

Analysis calculated for $C_{23}H_{30}N_4O_4S$ Requires C 60.24H 6.60N 12.22 Found C 60.21H 6.59N 12.08 i.r. (KBr) 2960, 1730, 1330, 1150 cm$^{-1}$ $[\alpha]_D^{20}$ −6.7 (c 2.0, CDCl$_3$)

$\delta_H$ 9.03 (1H, s), 8.37 (1H, d, J 5.5 Hz), 7.76 (2H, d, J 8.4 Hz), 7.18–7.11 (3H, m), 5.39 (2H, s), 4.65–4.59 (1H, m), 3.83 (2H, q, J 7.1 Hz), 2.82, (3H, s), 2.59 (3H, s), 1.69–1.55 (3H, m), 1.02.(3H, t, J 7.1 Hz), 0.97 (3H, d, J 6.1 Hz), 0.95 (3H, d, J 6.2 Hz).

(i) N-Methyl-N-4-(1H-2-methylimidazo[4,5-c]pyridinylmethyl)phenylsulphonyl-L-leucinol Lithium aluminium hydride (250 mg, 6.5 mmol) was added to a stirred solution of N-methyl-N-4-(1H-2-methylimidazo[4,5-c]pyridinylmethyl)phenylsulphonyl-L-leucine ethyl ester (2.0 g, 4.4 mmol) in dry THF (30 ml) under argon at room temperature. The reaction mixture was stirred overnight. Analysis by TLC (10% methanol in DCM) indicated that the reaction had not gone to completion. Additional lithium aluminium hydride (165 mg, 4.4 mmol) was added and the mixture stirred overnight. Water (0.5 ml) was added dropwise, followed by 15% aqueous sodium hydroxide (0.5 ml) and finally water (1.5 ml). The mixture was stirred for 0.5 h, filtered through celite and concentrated under reduced pressure. Chromatography (8–10% methanol in DCM) of the residue gave N-methyl-N-4-(1H-2-methylimidazo[4,5-c]pyridinylmethyl)phenylsulphonyl-L-leucinol (1.57 g, 89%) as a colourless oil.

i.r. (KBr) 3252, 2954, 1331, 1151 cm$^{-1}$ $\delta_H$ 8.79 (1H, s), 8.16 (1H, d, J 5.6 Hz), 7.69 (2H, d, J 8.3 Hz), 7.08 ( 1H, br s), 7.04 (2H, d, J 8.7 Hz), 5.32 (2H, s), 4.05–3.90 (2H, m), 3.44–3.36 (2H, m), 2.61 (3H, s), 2.46 (3H, s), 1.40–1.27 (1H, m), 1.13–1.08 (2H, m), 0.72 (6H, d, J 6.5 Hz); $\delta_C$ 153.66, 141.49, 141.07, 140.08, 140.02, 139.33, 139.22, 127.94, 126.49, 104.85, 62.10, 57.03, 46.63, 37.17, 28.01, 24.22, 22.60, 21.66.

EXAMPLES 2–21

The compounds of Examples 2–21 are prepared by the method of Example 1 employing the appropriate amino acid derivative in lieu of L-leucine ethyl ester hydrochloride in Step (b) and for certain compounds missing out the methylation Step (d) or employing a different alkyl halide in lieu of methyl iodide in Step (d).

2. N-4-(1H-2-Methylimidazo[4,5-c]pyridinylmethyl)phenylsulphonyl-L-leucinol
3. N-Methyl-N-4-(1H-2-methylimidazo[4,5-c]pyridinylmethyl)phenylsulphonyl-D-leucinol
4. N-Ethyl-N-4-(1H-2-methylimidazo[4,5-c]pyridinylmethyl)phenylsulphonyl-L-leucinol
5. N-Allyl-N-4-(1H-2-methylimidazo[4,5-c]pyridinylmethyl)phenylsulphonyl-L-leucinol
6. N-Propyl-N-4-(1H-2-methylimidazo[4,5-c]pyridinylmethyl)phenylsulphonyl-L-leucinol
7. N-Benzyl-N-4-(1H-2-methylimidazo[4,5-c]pyridinylmethyl)phenylsulphonyl-L-leucinol
8. N-4-Methoxybenzyl-N-4-(1H-2-methylimidazo[4,5-c]pyridinylmethyl)phenylsulphonyl-L-leucinol
9. N-Methyl-N-4-(1H-2-methylimidazo[4,5-c]pyridinylmethyl)phenylsulphonyl-L-isoleucinol
10. N-Methyl-N-4-(1H-2-methylimidazo[4,5-c]pyridinylmethyl)phenylsulphonyl-L-phenylalaninol
11. N-Methyl-N-4-(1H-2-methylimidazo[4,5-c]pyridinylmethyl)phenylsulphonyl-L-valinol
12. N-Methyl-N-4-(1H-2-methylimidazo[4,5-c]pyridinylmethyl)phenylsulphonyl-L-tryptophanol
13. N-Methyl-N-4-(1H-2-methylimidazo[4,5-c]pyridinylmethyl)phenylsulphonyl-L-methioninol
14. N-Methyl-N-4-(1H-2-methylimidazo[4,5-c]pyridinylmethyl)phenylsulphonyl-O-methyl-L-tyrosinol
15. N-Methyl-N-4-(1H-2-methylimidazo[4,5-c]pyridinylmethyl)phenylsulphonyl-L-norleucinol
16. N-Methyl-N-4-(1H-2-methylimidazo[4,5-c]pyridinylmethyl)phenylsulphonyl-L-phenylglycinol
17. N-Methyl-N-4-(1H-2-methylimidazo[4,5-c]pyridinylmethyl)phenylsulphonyl-L-t-butylglycinol
18. N-Methyl-N-4-(1H-2-methylimidazo[4,5-c]pyridinylmethyl)phenylsulphonyl-D,L-ethylglycinol
19. N-Methyl-N-4-(1H-2-methylimidazo[4,5-c]pyridinylmethyl)phenylsulphonyl-D,L-allylglycinol
20. N-Methyl-N-4-(1H-2-methylimidazo[4,5-c]pyridinylmethyl)phenylsulphonyl-L-cyclopropylalaninol
21. N-Methyl-N-4-(1H-2-methylimidazo[4,5-c]pyridinylmethyl)phenylsulphonyl-L-cyclopentylalaninol
22. N-Methyl-N-4-(1H-2-methylimidazo[4,5-c]pyridinylmethyl)phenylsulphonyl-L-cyclohexylalaninol

EXAMPLE 23

O-Ethanoyl-N-methyl-N-4-(1H-2-methylimidazo[4,5-c]pyridinylmethyl)phenylsulphonyl-L-leucinol

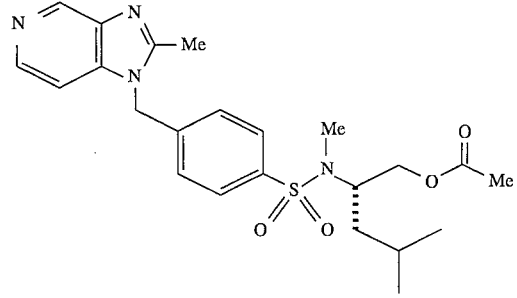

Acetic anhydride (1.6 ml, 17.4 mmol) was added slowly to a stirred solution of N-methyl-N-4-(1H-2-methylimidazo[4,5-c]pyridinylmethyl )phenylsulphonyl-L-leucinol (350 rag, 0.86 mmol) in a stirred mixture of dry DCM (10 ml) and pyridine (16 ml) containing 4-dimethylaminopyridine (10 mg) at room temperature. The mixture was stirred overnight. DCM was added and the mixture washed with 10% aqueous citric acid, saturated aqueous sodium hydrogen carbonate, saturated aqueous copper sulphate, brine, dried, filtered and concentrated. Chromatography (7% methanol in DCM) of the residue gave 0-ethanoyl-N-methyl-N-4-(1H-2-methylimidazo[4,5-c]pyridinylmethyl)phenylsulphonyl-L-leucinol (76 mg, 20%) as a pale yellow oil.

i.r. (DCM) 2930, 1740, 1360, 1150 cm$^{-1}$ $\delta_H$ 9.03 (1H, s), 8.37 (1H, d, J 4.4 Hz), 7.73 (2H, d, J 7.6 Hz), 7.12 ( 3H, m), 5.37 (2H, s), 4.27–4.16 (1H, m), 3.96–3.82 (2H, m), 2.64 (3H, s), 2.56 ( 3H, s), 1.86 (3H, s), 1.47–1.36 (1H, m), 1.28–1.08.(2H, m), 0.82 (6H, d, J 6.5 Hz);

$\delta_C$ 170.38, 153.30, 141.93, 140.35. 139.52, 127.98, 126.65, 104.69, 63.16, 53.71, 46.67, 37.62, 28.07, 24.28, 22.81, 21.93, 20.60.

EXAMPLES 24–43

The compounds of Examples 24–43 are prepared by the method of Example 23 employing the appropriate N-substituted-N-4-(1H-2-methylimidazo[4,5-c]pyridinylmethyl)phenylsulphonyl amino acid alcohol derivative in lieu of N-methyl-N-4-(1H-2-methylimidazo[ 4,5-c]pyridinylmethyl)phenylsulphonyl-L-leucinol.

24. O-Ethanoyl-N-methyl-N-4-(1H-2-methylimidazo[4,5-c]pyridinylmethyl)phenylsulphonyl-D-leucinol
25. O-Ethanoyl-N-ethyl-N-4-(1H-2-methylimidazo[4,5-c]pyridinylmethyl)phenylsulphonyl-L-leucinol
26. O-Ethanoyl-N-allyl-N-4-(1H-2-methylimidazo[4,5-c]pyridinylmethyl)phenylsulphonyl-L-leucinol
27. O-Ethanoyl-N-propyl-N-4-(1H-2-methylimidazo[4,5-c]pyridinylmethyl)phenylsulphonyl-L-leucinol
28. O-Ethanoyl-N-benzyl-N-4-(1H-2-methylimidazo[4,5-c]pyridinylmethyl)phenylsulphonyl-L-leucinol
29. O-Ethanoyl-N-4-methoxybenzyl-N-4-(1H-2-methylimidazo[ 4,5-c]pyridinylmethyl)phenylsulphonyl-L-leucinol
30. O-Ethanoyl-N-methyl-N-4-(1H-2-methylimidazo[ 4,5-c]pyridinylmethyl)2-phenylsulphonyl-L-isoleucinol
31. O-Ethanoyl-N-methyl-N-4-(1H-2-methylimidazo[4,5-c]pyridinylmethyl)phenylsulphonyl-L-phenylalininol
32. O-Ethanoyl-N-methyl-N-4-(1H-2-methylimidazo[4,5-c]pyridinylmethyl)phenylsulphonyl-L-valinol
33. O-Ethanoyl-N-methyl-N-4-(1H-2-methylimidazo[4,5-c]pyridinylmethyl)phenylsulphonyl-L-tryptophanol
34. O-Ethanoyl-N-methyl-N-4-(1H-2-methylimidazo[4,5-c]pyridinylmethyl)phenylsulphonyl-L-methioninol
35. O-Ethanoyl-N-methyl-N-4-(1H-2-methylimidazo[ 4,5-c]pyridinylmethyl)phenylsulphonyl-O-methyl-L-tyrosinol
36. O-Ethanoyl-N-methyl-N-4-(1H-2-methylimidazo[4,5-c]pyridinylmethyl)phenylsulphonyl-L-norleucinol
37. O-Ethanoyl-N-methyl-N-4-(1H-2-methylimidazo[4,5-c]pyridinylmethyl)phenylsulphonyl-L-phenylglycinol
38. O-Ethanoyl-N-methyl-N-4-(1H-2-methylimidazo[4,5-c]pyridinylmethyl)phenylsulphonyl-L-t-butylglycinol
39. O-Ethanoyl-N-methyl-N-4-(1H-2-methylimidazo[4,5-c]pyridinylmethyl)phenylsulphonyl-D,L-ethylglycinol
40. O-Ethanoyl-N-methyl-N-4-(1H-2-methylimidazo[4,5-c]pyridinylmethyl)phenylsulphonyl-D,L-allylglycinol
41. O-Ethanoyl-N-methyl-N-4-(1H-2-methylimidazo[ 4,5-c]pyridinylmethyl)phenylsulphonyl-L-cyclopropylalininol
42. O-Ethanoyl-N-methyl-N-4-(1H-2-methylimidazo[ 4,5-c]pyridinylmethyl)phenylsulphonyl-L-cyclopentylalininol
43. O-Ethanoyl-N-methyl-N-4-(1H-2-methylimidazo[ 4,5-c]pyridinylmethyl)phenylsulphonyl-L-cyclohexylalininol

EXAMPLE 44

O-Octadecanoyl-N-methyl-N-4-(1H-2-methylimidazo[4,5-c]pyridinylmethyl)phenylsulphonyl-L-leucinol

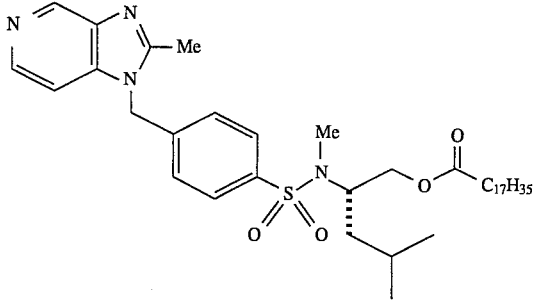

Stearoyl chloride (200 mg, 0.72 mmol) was added to a stirred solution of N-methyl-N-4-(1H-2-methylimidazo[4,5-c]pyridinylmethyl)phenylsulphonyl-L-leucinol (300 mg, 0.72 mmol) and triethylamine (0.1 ml, 0.72 mmol) in dry THF (10 ml) at room temperature under argon. The mixture was stirred overnight and the solvent removed under reduced pressure. The residue was taken up in DCM and washed with saturated aqueous sodium hydrogen carbonate and brine, dried, filtered and concentrated. Chromatography (3% methanol in DCM) gave O-octadecanoyl-N-methyl-N-4-(1H-2-methylimidazo[4,5-c]pyridinylmethyl)phenylsulphonyl-L-leucinol (182 mg, 37%) as a white crystalline solid.

m.p. 59° C.

i.r. (CDCl$_3$) 2930, 2850, 1725, 1340, 1160 cm$^{-1}$ $\delta_H$ 8.97 (1 H, s), 8.33 (1 H, s), 7.71 (2H, d, J 8.3 Hz), 7.13 (1 H, br s), 7.10 (2H, d, J 8.2 Hz), 5.34 (2H, s), 4.24–4.13 (1H, m), 3.96–3.81 (2H, m), 2.62 (3H, s), 2.53 (3H, s), 2.16 (2H, t, J 7.6 Hz), 1.65–1.03 (33H, m), 0.84–0.53 (9H, m); $\delta_C$ 187.63, 176.58, 173.20, 153.53, 141.56, 141.37, 140.29, 139.46, 127.92, 126.66, 104.74, 63.19, 53.70, 46.70, 37.63, 33.93, 31.76, 29.52, 29.32, 29.20, 28.99, 28.23, 24.60, 24.28, 22.79, 22.53, 21.94, 13.96.

EXAMPLES 45–49

The compounds of Examples 45–49 were prepared by the method of Example 44 employing the appropriate acid chloride in lieu of stearoyl chloride.

45. O-Propanoyl-N-methyl-N-4-(1H-2-methylimidazo[4,5-c]pyridinylmethyl)phenylsulphonyl-L-leucinol

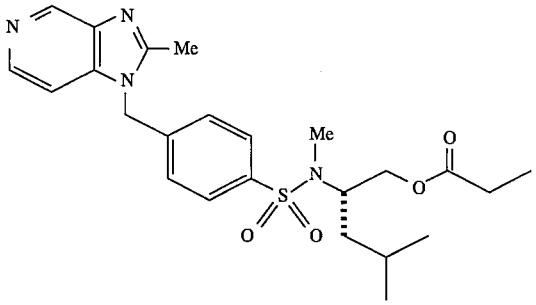

Yellow oil (38% yield after chromatography (5% methanol in DCM)):

i.r. (CDCl$_3$) 2960, 1735, 1340, 1155 cm$^{-1}$

δ$_H$ 8.99 (1H, s), 8.33 (1H, br d), 7.73 (2H, d, J 8.3 Hz), 7.11 (3H, m), 5.37 (2H, s), 4.29–4.17 (1H, m), 4.00–3.85 (2H, m), 2.64 (3H, s), 2.55 (3H, s), 2.16 ( 2H, q, J 7.4 Hz), 1.50–1.32 (1H, m), 1.25–1.13 (2H, m), 1.03 (3H, t, J 7.5 Hz), 0.81 (6H, br d);

δ$_C$ 173.62, 153.22, 142.10, 141.99, 140.56, 140.14, 139.59, 128.00, 126.68, 104.56, 63.25, 53.92, 46.74, 37.85, 28.26, 27.26, 24.41, 22.78, 22.03, 13.60.

46. O-2-Furoyl-N-methyl-N-4-(1H-2-methylimidazo[4,5-c]pyridinylmethyl)phenylsulphonyl-L-leucinol

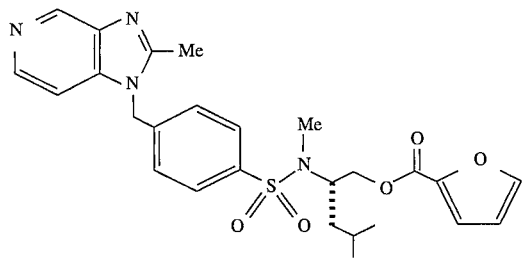

Yellow oil (22% yield after chromatography (5% methanol in DCM)):

i.r. (CDCl$_3$) 2960, 1720, 1340, 1180, 1120 cm$^{-1}$ δ$_H$ 9.00 (1H, br s), 8.34 (1H, br s), 7.72 (2H, d, J 8.3 Hz), 7.45 (1H, d, J 1.8 Hz), 7.12–7.10 (2H, m), 7.00 (2H, d, J 8.2 Hz), 6.39 (1H, dd, J 3.6, 1.8 Hz), 5.32 (2H, s), 4.43–4.32 (1H, m), 4.20 (1H, dd, J 11.6, 7.9 Hz), 4.04 (1H, dd, J 11.7, 4.5 Hz), 2.67 (3H, s), 2.53 (3H, s), 1.53–1.17 (3H, m), 0.86 (3H, d, J 6.4 Hz), 0.85 (3H, d, J 6.6 Hz);

δ$_C$ 158.07, 153.57, 146.53, 144.12, 141.68, 140.30, 139.51, 128.18, 126.62, 118.57, 111.97, 63.88, 53.93, 46.79, 37.87, 28.36, 24.44, 22.99, 22.03.

47. O-Ethyloxaloyl-N-methyl-N-4-(1H-2-methylimidazo[4,5-c]pyridinylmethyl)phenylsulphonyl-L-leucinol

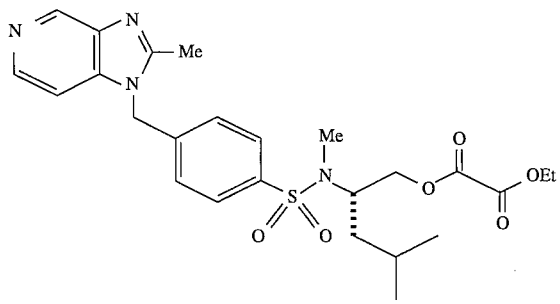

Pale yellow oil (29% yield after chromatography (3% methanol in DCM)):

i.r. (CDCl$_3$) 2960, 1780–1730, 1410–1350, 1130 cm$^{-1}$ δ$_H$ 8.95 (1H, s), 8.29 (1H, d, J 5.6 Hz), 7.71 (2H, d, J 8.3 Hz), 7.12 ( 1H, s), 7.07 (2H, d, J 8.6 Hz), 5.34 (2H, s), 4.27–4.01 (3H, m), 4.21 (2H, q, J 7.1 Hz), 2.63 (3H, s), 2.52 (3H, s), 1.40–0.98 (6H, m), 0.79 (3H, d, J 6.4 Hz), 0.78 (3H, d, J 5.2 Hz); δ$_C$ 200.22, 177.61, 157.16, 156.88, 153.32, 141.89, 141.67, 140.06, 139.73, 139.63, 127.95, 126.67, 104.61, 65.91, 63.09, 53.23, 46.59, 37.41, 28.32, 24.18, 22.69, 21.78, 13.77.

48. O-Benzoyl-N-methyl-N-4-(1H-2-methylimidazo[4,5-c]pyridinylmethyl)phenylsulphonyl-L-leucinol

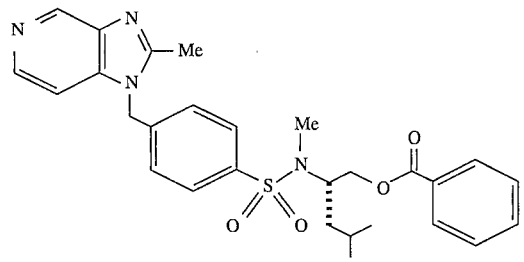

White foam (59% yield after chromatography (3–5% methanol in DCM)):

Analysis calculated for C$_{28}$H$_{32}$N$_4$O$_4$S.0.6H$_2$O Requires C 63.28 H 6.30 N 10.54 Found C 63.21 H 6.24 N 10.38 i.r. (CDCl$_3$) 2960, 1725, 1615, 1275, 1160 cm$^{-1}$ δ$_H$ 9.06 (1H, s), 8.39 (1H, d, J 5.5 Hz), 7.97 (2H, d, J 8.4 Hz), 7.77 ( 2H, d, J 8.2 Hz), 7.54 (1H, br dd), 7.39 (2H, dd, J 8.0, 7.4 Hz), 7.11 (1H, d, J 5.5 Hz), 7.00 (2H, d, J 8.2 Hz), 5.30 (2H, s), 4.49–4.42 (1H, m), 4.27 (1H, dd, J 11.7, 7.9 Hz), 4.13 (1H, dd, J 11.7, 4.5 Hz), 2.75 (3H, s), 2.56 (3H, s), 1.58–1.25 (3H, m), 0.93 (3H, d, J 6.4 Hz), 0.91 (3H, d, J 6.6 Hz).

49. O-2-Acetoxybenzoyl-N-methyl-N-4-(1H-2-methylimidazo[4,5-c]pyridinylmethyl)phenylsulphonyl-L-leucinol

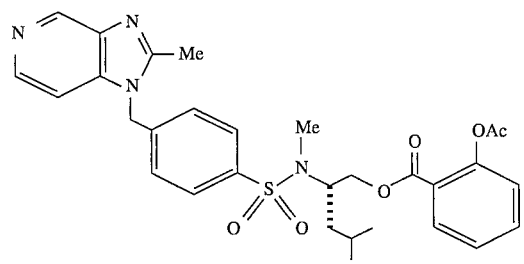

Yellow foam (22% yield after chromatography (5–8% methanol in DCM)):

i.r. (CDCl$_3$) 2960, 1760, 1725, 1340, 1180 cm$^{-1}$

δ$_H$ 9.01 (1H, s), 8.34 (1H, d, J 5.2 Hz), 7.92 (1H, dd, J 7.8, 1.5 Hz), 7.71 (2H, d, J 8.2 Hz), 7.47 (1H, m), 7.20 (1H, m), 7.08 (1H, d, J 5.4 Hz), 7.02 (1H, d, J 8.1 Hz), 6.94 (2H, d, J 8.2 Hz), 5.26 (2H, s), 4.47–4.33 (1H, m), 4.15–4.01 (2H, m), 2.68 (3H, s), 2.50 (3H, s), 2.30 (3H, s), 1.58–1.20 (3H, m), 0.88 (3H, d, J 6.4 Hz), 0.86 (3H, d, J 6.6 Hz);

δ$_C$ 169.38, 163.63, 153.32, 150.75, 141.95, 141.78, 140.17, 140.04, 139.54, 133.95, 131.48, 127.96, 126.65, 125.83, 123.67, 104.67, 64.04, 53.89, 46.64, 37.92, 28.26, 24.38, 22.88, 21.97, 20.89, 13.86.

EXAMPLES 50–77

The compounds of Examples 50–77 are prepared by the method of Example 44 employing the appropriate acid chloride in lieu of stearoyl chloride and for certain compounds the appropriate N-substituted-N-4-(1H-2-methylimidazo[4,5-c]pyridinylmethyl)phenylsulphonyl amino acid alcohol derivative was employed in lieu of N-methyl-N-4-(1H-2-methylimidazo[4,5-c]pyridinylmethyl)phenylsulphonyl-L-leucinol.

50. O-Propanoyl-N-4-(1H-2-methylimidazo[4,5-c]pyridinylmethyl)phenylsulphonyl-L-leucinol
51. O-Propanoyl-N-ethyl-N-4-(1H-2-methylimidazo[4,5-c]pyridinylmethyl)phenylsulphonyl-L-leucinol 52. O-Propanoyl-N-allyl-N-4-(1H-2-methylimidazo[4,5-c]pyridinylmethyl)phenylsulphonyl-L-leucinol
53. O-Propanoyl-N-methoxybenzyl-N-4-(1H-2-methylimidazo[4,5-c]pyridinylmethyl)phenylsulphonyl-L-leucinol
54. O-Propanoyl-N-methyl-N-4-(1H-2-methylimidazo[4,5-c]pyridinylmethyl)phenylsulphonyl-L-isoleucinol
55. O-Propanoyl-N-methyl-N-4-(1H-2-methylimidazo[4,5-c]pyridinylmethyl)phenylsulphonyl-L-cyclopentylalininol
56. O-Butanoyl-N-methyl-N-4-(1H-2-methylimidazo[4,5-c]pyridinylmethyl)phenylsulphonyl-L-leucinol
57. O-Pentanoyl-N-methyl-N-4-(1H-2-methylimidazo[4,5-c]pyridinylmethyl)phenylsulphonyl-L-leucinol
58. O-Hexanoyl-N-methyl-N-4-(1H-2-methylimidazo[4,5-c]pyridinylmethyl)phenylsulphonyl-L-leucinol
59. O-Octanoyl-N-methyl-N-4-(1H-2-methylimidazo[4,5-c]pyridinylmethyl)phenylsulphonyl-L-leucinol
60. O-Decanoyl-N-methyl-N-4-(1H-2-methylimidazo[4,5-c]pyridinylmethyl)phenylsulphonyl-L-leucinol
61. O-Dodecanoyl-N-methyl-N-4-(1H-2-methylimidazo[4,5-c]pyridinylmethyl)phenylsulphonyl-L-leucinol
62. O-Tetradecanoyl-N-methyl-N-4-(1H-2-methylimidazo[4,5-c]pyridinylmethyl)phenylsulphonyl-L-leucinol
63. O-Hexadecanoyl-N-methyl-N-4-(1H-2-methylimidazo[4,5-c]pyridinylmethyl)phenylsulphonyl-L-leucinol
64. O-2-Thiophenecarbonyl-N-methyl-N-4-(1H-2-methylimidazo[4,5-c]pyridinylmethyl)phenylsulphonyl-L-leucinol
65. O-2-Tetrahydrofuroyl-N-methyl-N-4-(1H-2-methylimidazo[4,5-c]pyridinylmethyl)phenylsulphonyl-L-leucinol
66. O-2-Pyridinecarbonyl-N-Methyl-N-4-(1H-2-methylimidazo[4,5-c]pyridinylmethyl)phenylsulphonyl-L-leucinol
67. O-3-Pyridinecarbonyl-N-methyl-N-4-(1H-2-methylimidazo[4,5-c]pyridinylmethyl)phenylsulphonyl-L-leucinol
68. O-4-Pyridinecarbonyl-N-methyl-N-4-(1H-2-methylimidazo[4,5-c]pyridinylmethyl)phenylsulphonyl-L-leucinol
69. O-3-Quinolinecarbonyl-N-methyl-N-4-(1H-2-methylimidazo[4,5-c]pyridinylmethyl)phenylsulphonyl-L-leucinol
70. O-2-Trifluoromethylbenzoyl-N-methyl-N-4-(1H-2-methylimidazo[4,5-c]pyridinylmethyl)phenylsulphonyl-L-leucinol
71. O-2-Bromobenzoyl-N-methyl-N-4-(1H-2-methylimidazo[4,5-c]pyridinylmethyl)phenylsulphonyl-L-leucinol
72. O-3-Chlorobenzoyl-N-methyl-N-4-(1H-2-methylimidazo[4,5-c]pyridinylmethyl)phenylsulphonyl-L-leucinol
73. O-4-Methoxybenzoyl-N-methyl-N-4-(1H-2-methylimidazo[4,5-c]pyridinylmethyl)phenylsulphonyl-L-leucinol
74. O-4-Fluorobenzoyl-N-methyl-N-4-(1H-2-methylimidazo[4,5-c]pyridinylmethyl)phenylsulphonyl-L-leucinol
75. O-3,4-Dimethoxybenzoyl-N-methyl-N-4-(1H-2-methylimidazo[4,5-c]pyridinylmethyl)phenylsulphonyl-L-leucinol
76. O-3-Chloro-4-methoxybenzoyl-N-methyl-N-4-(1H-2-methylimidazo[4,5-c]pyridinylmethyl)phenylsulphonyl-L-leucinol
77. O-2,2-Dimethylpropanoyl-N-methyl-N-4-(1H-2-methylimidazo[4,5-c]pyridinylmethyl)phenylsulphonyl-L-leucinol

EXAMPLE 78

O-2-(3,4-Dimethoxyphenylmercapto)ethanoyl-N-methyl-N-4-(1H-2-methylimidazo[4,5-c]pyridinylmethyl)phenylsulphonyl-L-leucinol

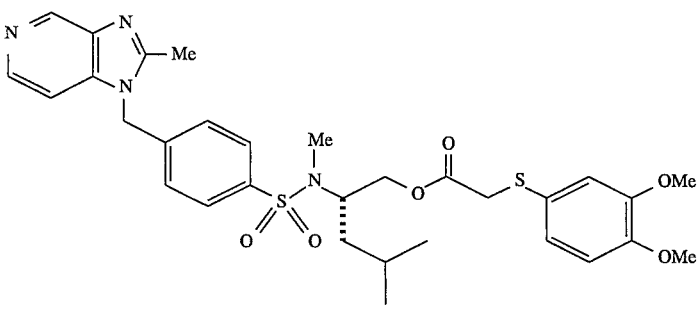

(a) Pentafluorophenyl 2-(3,4-dimethoxyphenylmercapto)ethanoate

A solution of 2-(3,4-dimethoxyphenylmercapto)ethanoic acid (1.71 g, 7.5 mmol), N-methylmorpholine (0.99 ml, 9.0 mmol), N-(3-dimethylaminopropyl)-N'-ethylcarbodiimide hydrochloride (1.87 g, 9.7 mmol) and pentafluorophenol (2.76 g, 15.0 mmol) in DCM (100 ml) was stirred at room temperature overnight. The solution was washed with 2M hydrochloric acid, saturated aqueous sodium hydrogen carbonate and brine, dried, filtered and concentrated to give crude pentafluorophenyl 2-(3,4-dimethoxyphenylmercapto)ethanoate (2.95 g, 99%) as pink oil which was used directly in the next step.

$\delta_H$ 7.16 (1H, dd, J 8.3, 2.2 Hz), 7.09 (1H, d, J 2.1 Hz), 6.85 (1H, d, J 8.3 Hz), 3.89 (6H, s), 3.81 (2H, s).

(b) O-2-(3,4-Dimethoxyphenylmercapto)ethanoyl-N-methyl-N-4-(1H-2-methylimidazo[4,5-c]pyridinylmethyl)phenylsulphonyl-L-leucinol A mixture of N-methyl-N-4-(1H-2-methylimidazo[4,5-c]pyridinylmethyl)phenylsulphonyl-L-leucinol (3.12 g, 7.5 mmol), pentafluorophenyl 2-(3,4-dimethoxyphenylmercapto)ethanoate (2.95 g, 7.4 mmol) and 4-N,N-dimethylaminopyridine (20 mg) in DCM (100 ml) was heated at reflux overnight. The mixture was cooled, washed with saturate aqueous sodium hydrogen carbonate and brine, dried, filtered and evaporated. Chromatography (4–6% methanol in DCM) gave O-2-(3,4-dimethoxyphenylmercapto)ethanoyl-N-methyl-N-4-(1H- 2-methylimidazo[4,5-c]pyridinylmethyl)phenylsulphonyl-L-leucinol (4.46 g, 95%) as a white foam.

i.r. (CDCl$_3$) 1735, 1610, 1585 cm$^{-1}$ $\delta_H$ 9.03 (1H, s), 8.35 (1H, d, J 5.5 Hz), 7.75 (2H, d, J 8.3 Hz), 7.14–7.11 (3H, m), 7.00–6.97 (2H, m), 6.77 (1H, dd, J 7.1, 1.9 Hz), 5.38 (2H, s), 4.27–4.16 (1H, m), 4.02–3.88 (2H, m), 3.85 (3H, s), 3.84 (3H, s), 3.39 (2H, s), 2.64 (3H, s), 2.58 (3H, s), 1.45–1.34 (1H, m), 1.27–1.07 (2H, m), 0.81 (6H, d, J 6.6 Hz);

$\delta_C$ 169.47, 153.25, 149.09, 142.14, 142.02, 140.33, 140.11, 139.76, 139.64, 128.05, 126.68, 125.12, 124.59, 115.07, 111.56, 104.58, 64.32, 55.93, 55.86, 53.62, 46.70, 37.90, 37.56, 28.23, 24.29, 22.61, 21.94, 13.69.

EXAMPLE 79

O-Retinoyl-N-methyl-N-4-(1H-2-methylimidazo[4,5-c]pyridinylmethyl)phenylsulphonyl-L-leucinol

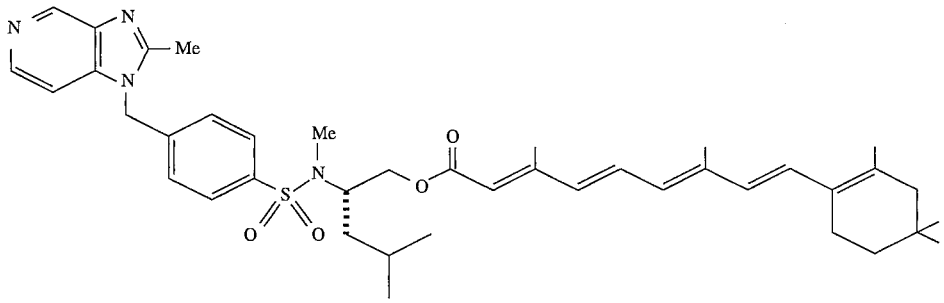

O-Retinoyl-N-methyl-N-4-(1H-2-methylimidazo[4,5-c]pyridinylmethyl)phenylsulphonyl-L-leucinol was prepared by the procedure of Example 78 employing retinoic acid in lieu of 2-(3,4-dimethoxyphenylmercapto)ethanoic acid as starting material.

Yellow foam (69% yield after chromatography (5% methanol in DCM)):

i.r. (DCM) 2925, 1710, 1610, 1570, 1340, 1145 $cm^{-1}$ $\delta_H$ 9.06 (1H, s), 8.42 (1H, d, J 5.9 Hz), 7.84 (2H, d, J 8.3 Hz), 7.33 (1H, d, J 5.9 Hz), 7.35–7.32 (2H, m), 7.04 (1H, dd, J 15.0, 11.4 Hz), 6.39–6.13 (4H, m), 5.61 (1H, s), 5.46 (2H, s), 4.36–4.25 (1H, m), 4.00–3.87 (2H, m), 2.73 (3H, s), 2.65 (3H, s), 2.33 (3H, s), 2.03 (3H, s), 2.05–1.95 (2H, m), 1.72 (3H, s), 1.68–1.23 (7H, m), 1.04 (6H, s), 0.92 (3H, d, J 6.4 Hz), 0.91 (3H, d, J 6.6 Hz);

$\delta_C$ (major signals) 117.45, 104.86, 63.01, 54.02, 46.85, 39.53, 37.92, 34.20, 33.05, 28.91, 28.46, 24.38, 23.00, 22.00, 21.69, 19.15, 13.92, 13.87, 12.91.

EXAMPLES 80–85

The compounds of Examples 80–85 are prepared by the method of Example 78 employing the appropriate carboxylic acid in lieu of 2-(3,4-dimethoxyphenylmercapto)ethanoic acid and N-methyl-N-4-(1H-2-methylimidazo[4,5-c]pyridinylmethyl)phenylsulphonyl-L-leucinol as starting material.

80. O-2-(4-Methoxyphenyl)ethanoyl-N-methyl-N-4-(1H-2-methylimidazo[ 4,5-c]pyridinylmethyl)phenylsulphonyl-L-leucinol
81. O-2-(3,4-Dimethoxyphenyl)ethanoyl-N-methyl-N-4-(1H-2-methylimidazo[4,5-c]pyridinylmethyl)phenylsulphonyl-L-leucinol
82. O-3-(4-Methoxyphenyl)propanoyl-N-methyl-N-4-(1H-2-methylimidazo[ 4,5c]pyridinylmethyl)phenylsulphonyl-L-leucinol
83. O-3-(3,4-Dimethoxyphenyl)propanoyl-N-methyl-N-4-(1H-2-methylimidazo[4,5-c]pyridinylmethyl)phenylsulphonyl-L-leucinol
84. O-3-(3-Chloro-4-methoxyphenyl)propanoyl-N-methyl-N-4-(1H-2-methylimidazo[4,5-c]pyridinylmethyl)phenylsulphonyl-L-leucinol
85. O-3-(Pyridin-3-yl)propanoyl-N-methyl-N-4-(1H-2-methylimidazo[ 4,5-c]pyridinylmethyl)phenylsulphonyl-L-leucinol

EXAMPLE 86

O-(N'-Benzyloxycarbonyl)-L-leucinoyl-N-Methyl-N-4-(1H-2-methylimidazo[4,5-c]pyridinylmethyl)phenylsulphonyl-L-leucinol

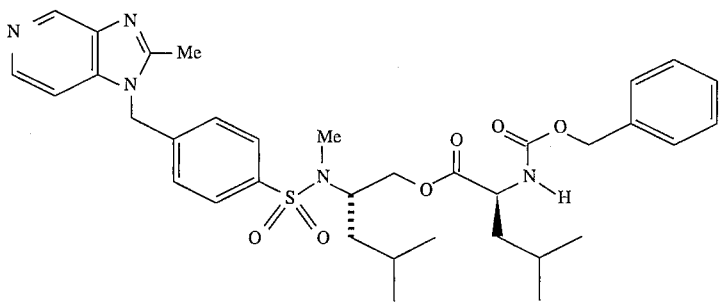

A mixture of N-methyl-N-4-(1H-2-methylimidazo[4,5-c]pyridinylmethyl)phenylsulphonyl-L-leucinol (350 mg, 0.86 mmol), N-benzyloxycarbonyl-L-leucine p-nitrophenyl ester (332 mg, 0.86 mmol) and imidazole (20 mg) in dry DCM (10 ml) was heated at reflux for 48 h. The solvent was removed under reduced pressure and the residue was dissolved in ethyl acetate, washed with 10% aqueous potassium carbonate and brine, dried, filtered and concentrated. Chromatography (7% methanol in DCM) of the residue gave O-(N'-benzyloxycarbonyl)-L-leucinoyl-N-methyl-N-4-(1H-2-methylimidazo[4,5-c]pyridinylmethyl)phenylsulphonyl-L-leucinol (290 mg, 51%) as a white foam.

i.r. (DCM) 2930, 1740, 1725, 1340, 1150 $cm^{-1}$ $\delta_H$ 9.05 (1H, s), 8.39 (1H, d, J 5.4 Hz), 7.78 (2H, d, J 7.5 Hz), 7.37–(5H, m), 7.21 (1H, d, J 5.6 Hz), 7.15 (2H, d, J 8.3 Hz), 5.41–5.33 (3H, m), 5.12 (2H, s), 4.29–4.21 (2H, m), 4.08 (1H, dd, J 11.6, 4.8 Hz), 3.89 (1H, dd, J 11.6, 8.2 Hz), 2.67 (3H, s), 2.60 (3H, s), 1.68–1.56 (2H, m), 1.52–1.39.(2H, m), 1.25–1.19 (2H, m), 0.92 (6H, br d, J 7.3 Hz), 0.87 (6H, br d, J 5.7 Hz);

δ$_C$ 172.46, 155.97, 153.54, 141.85, 141.74, 140.36, 140.21, 139.75, 136.36, 128.45, 128.07, 127.90, 126.81, 104.77, 66.84, 63.98, 53.59, 52.55, 46.79, 41.51, 37.71, 28.26, 24.66, 24.40, 22.84, 22.76, 22.06, 21.81.

EXAMPLES 87–95

The compounds of Examples 87–95 are prepared by the method of Example 86 employing the appropriate amino acid derivative in lieu of N-benzyloxycarbonyl-L-leucine p-nitrophenyl ester.
87. O-(N',N'-Dibenzyl)-L-leucinoyl-N-methyl-N-4-(1H-2-methylimidazo[ 4,5-c]pyridinylmethyl)phenylsulphonyl-L-leucinol
88. O-(N'-Benzyloxycarbonyl)glycinoyl-N-methyl-N-4-(1H-2-methylimidazo[4,5-c]pyridinylmethyl)phenylsulphonyl-L-leucinol
89. O-(N'-Benzyloxycarbonyl)-D-leucinoyl-N-methyl-N-4-(1H-2-methylimidazo[4,5-c]pyridinylmethyl)phenylsulphonyl-L-leucinol
90. O-(N'-Benzyloxycarbonyl)-L-phenylalininoyl-N-methyl-N-4-(1H-2-methylimidazo[4,5-c]pyridinylmethyl)phenylsulphonyl-L-leucinol
91. O-(N',N'-dibenzyl)glycinoyl-N-methyl-N-4-(1H-2-methylimidazo[ 4,5-c]pyridinylmethyl)phenylsulphonyl-L-leucinol
92. O-(N'-Benzyloxycarbonyl)-L-norleucinoyl-N-methyl-N-4-(1H-2-methylimidazo[ 4,5-c]pyridinylmethyl)phenylsulphonyl-L-leucinol
93. O-(N'-Butoxycarbonyl)-L-leucinoyl-N-methyl-N-4-(1H-2-methylimidazo[4,5-c]pyridinylmethyl)phenylsulphonyl-L-leucinol
94. O-(N'-Benzyloxycarbonyl)-L-valinoyl-N-methyl-N-4-(1H-2-methylimidazo[4,5-c]pyridinylmethyl)phenylsulphonyl-L-leucinol
95. O-(N'-Benzyloxycarbonyl)-L-phenylglycinoyl-N-methyl-N-4-(1H-2-methylimidazo[ 4,5-c]pyridinylmethyl)phenylsulphonyl-L-leucinol

EXAMPLE 96

O-Diethoxyphosphoryl-N-methyl-N-4-(1H-2-methylimidazo[ 4,5-c]pyridinylmethyl)phenylsulphonyl-L-leucinol

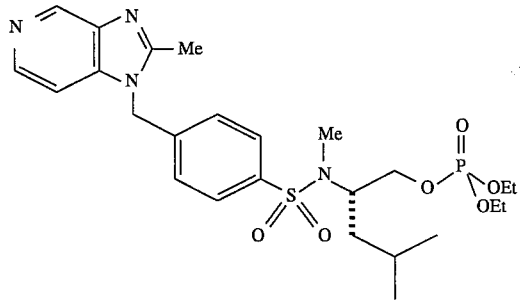

O-Diethoxyphosphoryl-N-methyl-N-4-(1H-2-methylimidazo[4,5-c]pyridinylmethyl)phenylsulphonyl-L-leucinol was prepared by the method of Example 44 employing diethyl chlorophosphate in lieu of stearoyl chloride.

Pale yellow oil (13% yield after chromatography (3–7% methanol in DCM)):

i.r. (CDCl$_3$) 2960, 1610, 1345, 1180 cm$^{-1}$

δ$_H$ 9.01 (1H, s), 8.35 (1H, d, J 5.3 Hz), 7.77 (2H, d, J 8.3 Hz), 7.16–7.11 ( 3H, m), 5.38 (2H, s), 4.27–4.16 (1H, m), 4.09–3.97 (4H, m), 3.87 (1H, d, J 5.8 Hz), 3.84 (1H, d, J 5.8 Hz), 2.68 (3H, s), 2.57 (3H, s), 2.49–1.33 (1H, m), 1.28–1.17 (8H, m), 0.84 (6H, d, J 6.5 Hz);

δ$_C$ 153.32, 142.06, 141.93, 140.15, 140.05, 139.77, 139.61, 128.12, 126.65, 104.65, 67.05, 66.96, 63.90, 63.81, 54.73, 54.60, 46.73, 37.16, 28.45, 24.26, 22.88, 21.91, 16.06, 15.96.

EXAMPLES 97–99

The compounds of Examples 97–99 are prepared by the method of Example 96 employing the appropriate chlorophosphate derivative in lieu of diethyl chlorophosphate.
97. O-Dimethoxyphosphoryl-N-methyl-N-4-(1H-2-methylimidazo[ 4,5-c]pyridinylmethyl)phenylsulphonyl-L-leucinol
98. O-Diphenoxyphosphoryl-N-methyl-N-4-(1H-2-methylimidazo[ 4,5-c]pyridinylmethyl)phenylsulphonyl-L-leucinol
99. O-Diisopropoxyphosphoryl-N-methyl-N-4-(1H-2-methylimidazo[ 4,5-c]pyridinylmethyl)phenylsulphonyl-L-leucinol

EXAMPLE 100

O-Methylsulphonyl-N-methyl-N-4-(1H-2-methylimidazo[4,5-c]pyridinylmethyl)phenylsulphonyl-L-leucinol

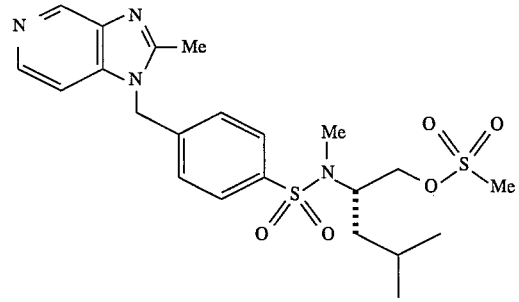

O-Methylsulphonyl-N-methyl-N-4-(1H-2-methylimidazo[4,5-c]pyridinylmethyl)phenylsulphonyl-L-leucinol was prepared by the method of Example 44 employing methanesulphonyl chloride in lieu of stearoyl chloride.

White foam (61% yield after chromatography (3% methanol in DCM)):

i.r. (CDCl$_3$) 2960, 1615, 1360 cm$^{-1}$

δ$_H$ 9.05 (1H, s), 8.39 (1H, d, J 5.5 Hz), 7.80 (2H, d, J 8.4 Hz), 7.17–7.14 (3H, m), 5.40 (2H, s), 4.34–4.28 (1H, m), 4.09–4.02 (2H, m), 2.90 (3H, s), 2.72 ( 3H, s), 2.60 (3H, s), 1.53–1.15 (3H, m), 0.89 (6H, d, J 6.5 Hz);

δ$_C$ 153.36, 142.16, 142.04, 140.18, 139.90, 128.16, 126.78, 104.68, 68.34, 53.90, 46.77, 37.29, 30.87, 28.39, 24.33, 22.92, 21.85.

EXAMPLES 101–104

The compounds of Examples 101–104 are prepared by the method of Example 100 employing the appropriate sulphonyl chloride derivative in lieu of methanesulphonyl chloride.
101. O-Ethylsulphonyl-N-methyl-N-4-(1H-2-methylimidazo[4,5-c]pyridinylmethyl)phenylsulphonyl-L-leucinol
102. O-Propylsulphonyl-N-methyl-N-4-(1H-2-methylimidazo[4,5-c]pyridinylmethyl)phenylsulphonyl-L-leucinol
103. O-Phenylsulphonyl-N-methyl-N-4-(1H-2-methylimidazo[4,5-c]pyridinylmethyl)phenylsulphonyl-L-leucinol 104. O-4-Methylphenylsulphonyl-N-methyl-N-4-(1H-2-methylimidazo[ 4,5-c]pyridinylmethyl)phenylsulphonyl-L-leucinol

EXAMPLE 105

O-Benzylaminocarbonyl-(N-methyl-N-4-(1H-2-methylimidazo[4,5-c]pyridinylmethyl)phenylsulphonyl)-L-leucinol

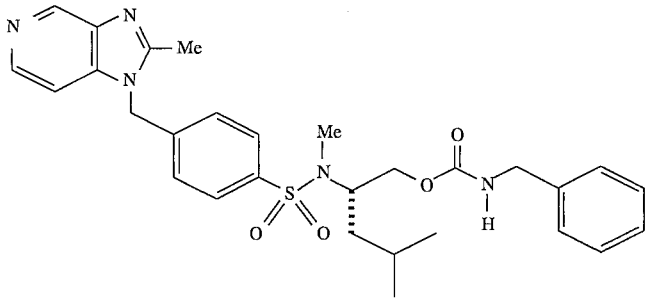

(a) Dipyrid-2-ylcarbonate

Triethylamine (10.5 ml, 75 mmol) was added slowly to a solution of triphosgene (3.0 g, 10 mmol) and 2-hydroxypyridine (5.7 g, 60 mmol) in dry DCM (500 ml) at 0° C. under argon. The mixture was allowed to warm to room temperature and was stirred overnight. The solvent was removed under reduced pressure and the residue taken up in ethyl acetate (500 ml), washed with saturated aqueous sodium hydrogen carbonate (2×150 ml) and brine (200 ml), dried, filtered and concentrated to give an orange oil. Crystallisation from ethyl acetate/hexane gave dipyrid-2-ylcarbonate as an off-white crystalline solid (3.70 g, 57%).

$\delta_H$ 8.42 (2H, dd, J 4.8, 1.1 Hz), 7.83 (2H, ddd, J 7.8, 7.7, 1.8 Hz), 7.30–7.23 (4H, m).

(b) O-Pyridin-2-yloxycarbonyl-N-methyl-N-4-(1H-2-methylimidazo[ 4,5-c]pyridinylmethyl)phenylsulphonyl-L-leucinol Dipyrid-2-ylcarbonate (234 mg, 1.1 mmol) was added to a stirred solution of triethylamine (100 μμl, 1.1 mmol) and N-methyl-N-4-(1H-2-methylimidazo[ 4,5c]pyridinylmethyl)phenylsulphonyl-L-leucinol (300 mg, 0.7 mmol) in dry DCM (5 ml) at room temperature under argon. The mixture was stirred overnight, DCM (40 ml) added and the solution washed with saturated aqueous sodium hydrogen carbonate and brine. The organics were dried, filtered and concentrated to give crude O-pyridin-2-yloxycarbonyl-N-methyl-N-4-(1H-2-methylimidazo[4,5-c]pyridinylmethyl)phenylsulphonyl-L-leucinol (366 mg, 95%) as a white foam, which was used directly in the next step.

$\delta_H$ 8.97 (1H, s), 8.36–8.29 (2H, m), 7.86–7.77 (3H, m), 7.29–7.23 (1H, m), 7.17–7.05 (4H, m), 5.36 (2H, s), 4.45–4.33 (1H, m), 4.09–4.06 (2H, m), 3.46 (3H, s), 2.72 (3H, s), 1.63–1.46 (1H, m), 1.42–1.16 (2H, m), 0.90 (6H, d, J 6.5 Hz).

(c) O-Benzylaminocarbonyl-N-methyl-N-4-(1H-2-methylimidazo[4,5-c]pyridinylmethyl)phenylsulphonyl-L-leucinol A solution of O-pyridin-2-yloxycarbonyl-(N-methyl-N-4-(1H-2-methylimidazo[4,5-c]pyridinylmethyl)phenylsulphonyl)-L-leucinol (366 mg, 0.7 mmol) in dry DCM (2 ml) was added to a stirred solution of benzylamine (90 μl, 0.8 mmol) in dry DCM (5 ml) at room temperature under argon. The mixture was stirred overnight, DCM (40 ml) added and the solution washed with 10% aqueous citric acid. The organics were concentrated under reduced pressure and the residue partitioned between ethyl acetate and saturated aqueous sodium hydrogen carbonate. The organic phase was washed with brine, dried, filtered and evaporated to give a yellow foam. Chromatography (5% methanol in DCM) gave O-benzylaminocarbonyl-N-methyl-N-4-(1H-2-methylimidazo[4, 5-c]pyridinylmethyl)phenylsulphonyl-L-leucinol (140 mg, 37%) as a colourless oil.

i.r. (CDCl$_3$) 3450, 1725, 1340, 1150 cm$^{-1}$ $\delta_H$ 8.96 (1H, s), 8.30 (1H, d, J 5.6 Hz), 7.73 (2H, d, J 8.2 Hz), 7.32–7.21 (5H, m), 7.08–7.05 (1H, m), 7.06 (2H; d, J 8.3 Hz), 5.49–5.15 (1H, m), 5.25 (2H, s), 4.28–4.20 (1H, m), 4.27 (2H, d, J 5.9 Hz), 3.92 (2H, d, J 6.5 Hz), 2.63 (3H, s), 2.51 (3H, s), 1.50–1.30 (1H, m), 1.30–1.05 (2H, m), 0.83 (3H, d, J 6.1 Hz), 0.82 (3H, d, J 6.4 Hz);

$\delta_C$ 155.86, 153.57, 141.58, 141.41, 140.31, 139.66, 139.42, 138.22, 128.56, 128.06, 127.42, 127.30, 104.73, 63.69, 54.09, 46.64, 44.88, 37.46, 28.04, 24.29, 22.88, 21.93.

EXAMPLE 106–109

The compounds of Examples 106–109 were prepared by the procedure of Example 105 employing the appropriate amine.

106. O-4-Ethoxycarbonylpiperazinecarbonyl-N-methyl-N-4-(1H-2-methylimidazo[4,5-c]pyridinylmethyl)phenylsulphonyl-L-leucinol

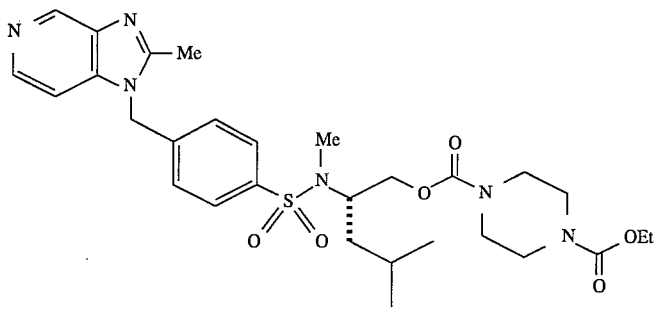

Colourless oil (14% yield after chromatography (5% methanol in DCM)):

i.r. (CDCl$_3$) 3330, 2930, 1715–1650, 1420–1335, 1110–1080 cm$^{-1}$ $\delta_H$ 9.01 (1H, s), 8.34 (1H, d, J 5.6 Hz), 7.74 (2H, d, J 8.3 Hz), 7.14–7.10 (3H, m), 5.38 (2H, s), 4.34–4.23 (1H, m), 4.11 (2H, q, J 7.0 Hz), 3.98 (2H, d, J 7.1 Hz), 3.45 (8H,s), 2.61 (3H, s), 2.56 (3H, s), 1.96–1.34 (1H, m), 1.22 (3H, t, J 7.2 Hz), 1.12 (2H, dd, J 7.0, 6.8 Hz), 0.80 (3H, d, J 6.3 Hz), 0.79 (3H, d, J 6.4 Hz);

$\delta_C$ 155.28, 154.60, 153.26, 142.00, 141.87, 140.42, 140.11, 139.73, 139.52, 127.87, 126.65, 104.56, 63.57, 61.41, 54.01, 46.69, 43.50, 43.27, 37.36, 27.76, 24.41, 22.75, 22.10, 14.51.

107. O-5-Ethyl-1,3,4-thiadiazol-2-ylaminocarbonyl-N-methyl-N-4-(1H-2methylimidazo[4,5-c]pyridinylmethyl)phenylsulphonyl-L-leucinol $\delta_H$ 8.96 (1H, s), 8.60 (1H, d, J 5.7 Hz), 7.78 (2H, d, J 8.3 Hz), 7.69 (1H, d, J 5.6 Hz), 6.94 (2H, d, J 8.3 Hz), 5.42, 5.39 (2H, 2s), 4.49–4.37 (1H, m), 4.23 (1H, dd, J 11.7, 10.6 Hz), 4.03 (1H, dd, J 11.8, 4.0 Hz), 3.08 (2H, q, J 7.6 Hz), 2.89 (3H, s), 2.46 (3H, s), 1.80–1.66 (1H, m), 1.51–1.39 (1H, m), 1.44 (3H, t, J 7.6 Hz), 1.26–1.14 (1H, m), 1.00 (3H, d, J 6.3 Hz), 0.98 (3H, d, J 6.6 Hz);

$\delta_C$ 167.01, 160.68, 154.69, 152.79, 141.54, 141.31, 140.75, 140.00, 139.79, 105.87, 65.16, 54.50, 47.07, 37.84, 28.22, 24.50, 23.64, 23.05, 22.16, 14.01.

108. O-Pyridin-2-ylmethylaminocarbonyl-N-methyl-N-4-(1H-2-methylimidazo[4,5-c]pyridinylmethyl)phenylsulphonyl-L-leucinol

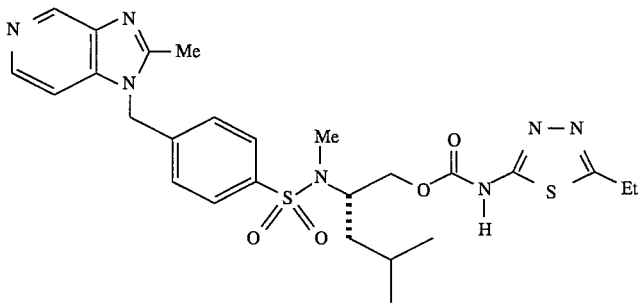

White foam (1% yield after chromatography (5–8% methanol in DCM)):

i.r. (CDCl$_3$) 3370, 2960, 1735–1715, 1430, 1140 cm$^{-1}$

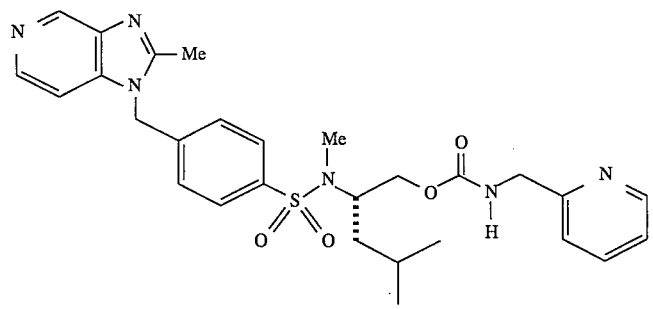

White foam (61% yield after chromatography (5–10% methanol in DCM)):

i.r. (CDCl$_3$) 3665, 3630, 2960, 1735–1690, 1345, 1175 cm$^{-1}$ $\delta_H$ 8.93 (1H, s), 8.45 (1H, dd, J 4.8, 1.0 Hz), 8.28 (1H, d, J 5.6 Hz), 7.74 (2H, d, J 8.2 Hz), 7.62 (1H, ddd, J 7.7, 7.6, 1.6 Hz), 7.23 (1H, d, J 7.8 Hz), 7.17–7.08 (4H, m), 5.87–5.83 (1H, m), 5.34 (2H, s), 4.35 (2H, dd, J 5.7, 5.5 Hz), 4.28–4.17 (1H, m), 3.90 (2H, d, J 6.3 Hz), 2.63 (3H, s), 2.51 (3H, s), 1.49–1.41 (1H, m), 1.23–1.10 (2H, m), 0.83 (3H, d, J 6.3 Hz), 0.82 (3H, d, J 6.6 Hz);

$\delta_C$ 156.63, 155.88, 153.44, 148.85, 141.63, 141.59, 140.24, 140.14, 139.57, 139.46, 136.80, 128.07, 126.60, 122.37, 121.69, 104.67, 63.65, 54.14, 50.18, 46.66, 45.81, 37.50, 28.02, 24.26, 22.67, 21.90.

109. O-Octadecylaminocarbonyl-N-methyl-N-4-(1H-2-methylimidazo[ 4,5-c]pyridinylmethyl)phenylsulphonyl-L-leucinol

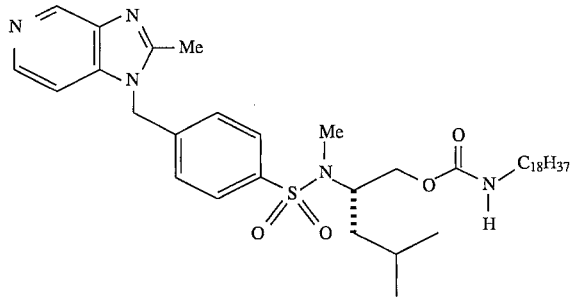

Colourless oil (5% yield after chromatography (3% methanol in DCM)):

i.r. (CDCl$_3$) 3440, 2920, 1710, 1335, 1140 cm$^{-1}$ $\delta_H$ 9.04 (1H, s), 8.37 (1H, d, J 5.6 Hz), 7.78 (2H, d, J 8.4 Hz), 7.14 ( 3H, m), 5.39 (2H, s), 4.74–4.65 (1H, m), 4.27–4.22 (1H, m), 3.90 (2H, d, J 6.5 Hz), 3.13–3.04 (2H, m), 2.64 (3H, s), 2.58 (3H, s), 1.46–1.35 (3H, m), 1.33–1.10 (32H, m), 0.87–0.83 (9H, m);

$\delta_C$ 155.88, 153.32, 142.08, 141.98, 140.20, 139.48, 128.17, 126.65, 104.59, 3.47, 54.14, 46.79, 41.06, 37.54, 31.86, 29.89, 29.63, 29.29, 29.23, 28.13, 6.67, 24.40, 22.95, 22.63, 22.02, 14.05.

EXAMPLE 110–130

The compounds of Examples 110–130 are prepared by the procedure of Example 105 employing the appropriate amine.

110. O-Methylaminocarbonyl-N-methyl-N-4-(1H-2-methylimidazo[ 4,5-c]pyridinylmethyl)phenylsulphonyl-L-leucinol
111. O-Ethylaminocarbonyl-N-methyl-N-4-(1H-2-methylimidazo[ 4,5-c]pyridinylmethyl)phenylsulphonyl-L-leucinol
112. O-n-Prop ylaminocarbonyl-N-methyl-N-4-(1H-2-methylimidazo[ 4,5-c ]pyridinylmethyl)phenylsulphonyl-L-leucinol
113. O-i-Propylaminocarbonyl-N-methyl-N-4-(1H-2-methylimidazo[ 4,5-c]pyridinylmethyl)phenylsulphonyl-L-leucinol
114. O-n-Pentylaminocarbonyl-N-methyl-N-4-(1H-2-methylimidazo[ 4,5-c]pyridinylmethyl)phenylsulphonyl-L-leucinol
115. O-n-Hexylaminocarbonyl-N-methyl-N-4-(1H-2-methylimidazo[ 4,5-c]pyridinylmethyl)phenylsulphonyl-L-leucinol
116. O-n-Octylaminocarbonyl-N-methyl-N-4-(1H-2-methylimidazo[ 4,5-c]pyridinylmethyl)phenylsulphonyl-L-leucinol
117. O-n-Decylaminocarbonyl-N-methyl-N-4-(1H-2-methylimidazo[ 4,5-c]pyridinylmethyl)phenylsulphonyl-L-leucinol
118. O-n-Dodecylamino carbonyl-N-methyl-N-4-(1H-2-methylimidazo[ 4,5-c]pyridinylmethyl)phenylsulphonyl-L-leucinol
119. O-n-Tetradecyl aminocarbonyl-N-methyl-N-4-(1H-2-methylimidazo[ 4,5-c]pyridinylmethyl)phenylsulphonyl-L-leucinol
120. O-n-Hexadecylaminocarbonyl-N-methyl-N-4-(1H-2-methylimidazo[ 4,5-c]pyridinylmethyl)phenylsulphonyl-L-leucinol
121. O-t-Butylaminocarbonyl-N-methyl-N-4-(1H-2-methylimidazo[ 4,5-c]pyridinylmethyl)phenylsulphonyl-L-leucinol
122. O-Pyridin-2-ylaminocarbonyl-N-methyl-N-4-(1H-2-methylimidazo[ 4,5-c]pyridinylmethyl)phenylsulphonyl-L-leucinol
123. O-Pyridin-4-ylmethylaminocarbonyl-N-methyl-N-4-(1H-2-methylimidazo[4,5-c]pyridinylmethyl)phenylsulphonyl-L-leucinol
124. O-Pyridin-3-ylmethylaminocarbonyl-N-methyl-N-4-(1H-2-methylimidazo[4,5-c]pyridinylmethyl)phenylsulphonyl-L-leucinol
125. O-4-Methoxyphenylaminocarbonyl-N-methyl-N-4-(1H-2-methylimidazo[4,5-c]pyridinylmethyl)phenylsulphonyl-L-leucinol
126. O-3,4-Dimethoxybenzylaminocarbonyl-N-methyl-N-4-(1H-2-methylimidazo[4,5-c]pyridinylmethyl)phenylsulphonyl-L-leucinol
127. O-2-(4-Methoxyphenyl)ethylaminocarbonyl-N-methyl-N-4-(1H-2-methylimidazo[4,5-c]pyridinylmethyl)phenylsulphonyl-L-leucinol
128. O-2-(3,4-Dimethoxyphenyl)ethylaminocarbonyl-N-methyl-N-4-(1H-2methylimidazo[4,5-c]pyridinylmethyl)phenylsulphonyl-L-leucinol
129. O-3-(3,4-Dimethoxyphenyl)propylaminocarbonyl-N-methyl-N-4-(1H-2methylimidazo[4,5-c]pyridinylmethyl)phenylsulphonyl-L-leucinol
130. O-3-(Pyridin-3-yl)propylaminocarbonyl-N-methyl-N-4-(1H-2-methylimidazo[4,5-c]pyridinylmethyl)phenylsulphonyl-L-leucinol

EXAMPLE 131

N-Methyl-N-4-(1H-2-methylimidazo[4,5-c]pyridinylmethyl)phenylsulphonyl-2-thienylmethylamine

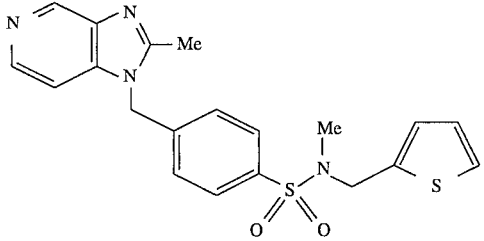

(a) 4-Bromomethylphenylsulphonyl-2-thienylmethylamine

4-Bromomethylphenylsulphonyl-2-thienylmethylamine was prepared by the procedure of Example 1 Step (b) employing 2-thienylmethylamine in lieu of L-leucine ethyl ester hydrochloride.

Yellow amorphous solid (66% yield after chromatography (1:3 ethyl acetate/hexane)):

$\delta_H$ 7.85 (2H, d, J 8.3 Hz), 7.54 (2H, dd, J 8.3 Hz), 7.21 (1H, d, J 4.7 Hz), 6.91–6.87 (2H, m), 4.75 (1H, br s), 4.51 (2H, s), 4.39 (2H, d, J 5.7 Hz).

(b) N-Methyl 4-bromomethylphenylsulphonyl-2-thienylmethylamine

A mixture of 4-bromomethylphenylsulphonyl-2-thienylmethylamine (10.0 g, 28.9 mmol), dimethylsulphate (2.75 ml, 28.9 mmol) and potassium carbonate (19.96 g, 144 mmol) in acetone (100 ml) was stirred overnight at room temperature. The solvent was removed under reduced pressure and the residue taken up in ethyl acetate, washed with water and brine, dried, filtered and evaporated. Chromatography of the residue (1:2 ethyl acetate/hexane) gave N-methyl 4-bromomethylphenylsulphonyl-2-thienylmethylamine (1.60 g, 15%) as a colourless oil which was used directly in the next step.

(c) N-Methyl-N-4-(1H-2-methylimidazo[4,5-c]pyridinylmethyl)phenylsulphonyl-2-thienylmethylamine A suspension of potassium hydroxide (0.60 g, 10.0 mmol), TDA-1 (4 drops) in dry acetonitrile (20 ml) was stirred for 10 min. at room temperature under argon. 2-Methylimidazo[4,5-c]pyridine (0.60 g, 4.4 mmol) was added and the reaction mixture was heated at 80° C. for 40 min and cooled to 40° C. A solution of N-methyl 4-bromomethylphenylsulphonyl-2-thienylmethylamine (1.6 g, 4.4 mmol) in dry acetonitrile (10 ml) was added and the reaction mixture stirred at 40° C. overnight and cooled to room temperature. The solvent was removed and the residue taken up in ethyl acetate, washed with brine, dried, filtered and concentrated. Column chromatography (6% methanol in DCM) gave N-methyl-N-4-(3 H-2-methylimidazo[ 4,5-c]pyridinylmethyl)phenylsulphonyl-2-thienylmethylamine (0.17 g, 9%), N-methyl-N-4-(1H-2-methylimidazo[4,5-c]pyridinylmethyl)phenylsulphonyl- 2-thienylmethylamine (0.21 g, 12%) and N-methyl-N-4-(5H-2-methylimidazo[4,5-c]pyridinylmethyl)phenylsulphonyl- 2-thienylmethylamine. The 3H- and 5H-regioisomers, although not claimed in this patent application, are antagonists of platelet activating factor. N-Methyl-N-4-(1H-2-methylimidazo[4,5-c]pyridinylmethyl)phenylsulphonyl-2-thienylmethylamine was obtained as a yellow oil.

i.r. (CDCl$_3$) 2210, 1610, 1350, 1160 cm$^{-1}$ $\delta_H$ 9.02 (1H, s), 8.37 (1H, s), 7.71 (2H, d, J 8.3 Hz), 7.16 (4H, m), 6.86 (2H, m), 5.39 (2H, s), 4.35 (2H, s), 2.66 (3H, s), 2.58 (3H, s);

$\delta_C$ 153.29, 141.86, 141.63, 140.01, 139.92, 137.70, 137.60, 127.96, 127.24, 126.80, 126.55, 125.99, 104.65, 48.48, 46.57, 33.99.

EXAMPLE 132

N-Methyl-N-4-(1H-2-methylimidazo[4,5-c]pyridinylmethyl)phenylsulphonyltetrahydrofurfurylamine

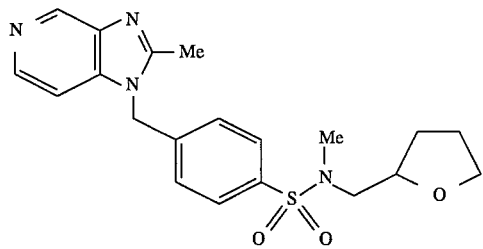

N-Methyl-N-4-(1H-2-methylimidazo[4,5-c]pyridinylmethyl)phenylsulphonyl-2-tetrahydrofurfurylamine was prepared by the procedure of Example 131 employing tetrahydrofurfurylamine in lieu of 2-thienylmethylamine.

Yellow foam (10% yield for last step after chromatography (5% methanol in DCM)):

i.r. (CDCl$_3$) 2860, 1600, 1340, 1150 cm$^{-1}$ $\delta_H$ 8.52 (1H, s), 8.33 (1H, s), 7.61 (2H, d, J 8.2 Hz), 7.53 (1H, d, J 3.9 Hz), 7.11 (2H, d, J 8.3 Hz), 5.39.(2H, s), 3.95–3.87 (1H, m), 3.74–3.55 (2H, m), 3.08 (1H, dd, J 13.8, 4.2 Hz), 2.83 (1H, dd, J 13.9, 6.6 Hz), 2.72 (3H, s), 2.53 (3H, s), 1.91–1.72 (3H, m), 1.62–1.52 (1H, m);

$\delta_C$ 154.95, 147.63, 142.07, 139.67, 132.79, 132.17, 127.93, 126.71, 113.83, 7.55, 67.91, 53.48, 46.79, 36.05, 28.79, 25.19.

EXAMPLE 133

N-4-(1H-2-Methylimidazo[4,5-c]pyridinylmethyl)phenylsulphonyl-2-(N'-methylpyrrol-2-yl)ethylamine

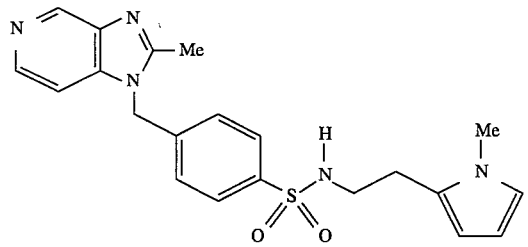

N-Methyl-N-4-(1H-2-methylimidazo[4,5-c]pyridinylmethyl)phenylsulphonyl-2-(N'-methylpyrrol- 2-yl)ethylamine was prepared by the procedure of Example 131 Steps (a) and (c) employing (N'-methylpyrrol-2-yl)ethylamine as starting material in lieu of 2-thienylmethylamine.

Yellow oil (0.3% yield for last step after chromatography (8% methanol in DCM)):

i.r. (CDCl$_3$) 1605, 1510, 1340, 1230, 1160, 985 cm$^{-1}$ $\delta_H$ 9.04 (1H, s), 8.40 (1H, s), 7.79 (2H, d, J 8.3 Hz), 7.20 (1H, s), 7.16 (2H, d, J 8.4 Hz), 6.51–6.50 (1H, m), 6.00 (1H, t, J 3.1 Hz), 5.77 (1H, dd, J 3.4, 1.8 Hz), 5.42 (2H, s), 5.08 (1H, t, J 6.3 Hz), 3.45 (3H, s), 3.22–3.14 (2H, m), 2.76 ( 2H, t, J 6.8 Hz), 2.01 (3H, s).

EXAMPLE 134

N-Methyl-N-4-(1H-2-methylimidazo[4,5-c ]pyridinylmethyl)phenylsulphonyl-1-(4-fluorophenyl)-1-(2-thienyl)methylamine

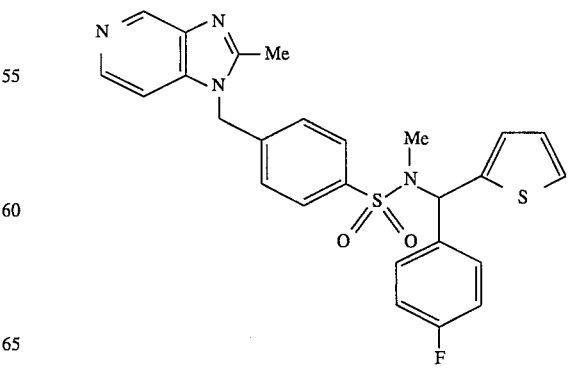

(a) (4-Fluorophenyl)-(2-thienyl)methanol

Lithium aluminium hydride (3.68 g, 97 mmol) was added portionwise to a stirred solution of (4-fluorophenyl)-(2-thienyl)ketone (10.0 g, 48.5 mmol) in dry THF (160 ml) at room temperature under argon. The mixture was stirred overnight and water (3.7 ml) added dropwise with caution. After 0.5 h 15% aqueous sodium hydroxide (3.7 ml) was added and the mixture stirred for 0.5 h, finally water (11 ml) was added and the mixture stirred for 0.5 h. The precipitate was removed by filtration through celite and the flitrate was concentrated under reduced pressure to give (4-fluorophenyl)-(2-thienyl)methanol (10.0 g, 99%) as a yellow oil.

$\delta_H$ 7.45–7.39 (2H, m), 7.28 (1H, dd, J 5.1, 1.1 Hz), 7.09–7.02 (2H, m), 6.96 (1H, dd, J 5.1, 3.5 Hz), 6.90–6.88 (1H, m), 6.04 (1H, s), 2.62 (1H, br s).

(b) (4-Fluorophenyl)-(2-thienyl)methylamine

A solution of diethyl azodicarboxylate (4.20 g, 24 mmol) in dry THF (20 ml) was added dropwise to a stirred mixture of (4-fluorophenyl)-(2-thienyl)methanol (5.0 g, 24 mmol), phthalamide (3.53 g, 24 mmol) and triphenyl phosphine (6.3 g, 24 mmol) in dry THF (60 ml) at room temperature under argon. The reaction mixture was stirred overnight and the solvent removed under reduced pressure. Diethyl ether was added and the mixture was placed in the refrigerator overnight. The precipitate that formed was removed by filtration and the filtrate was concentrated under reduced pressure. The residue was dissolved in ethanol (160 ml) and hydrazine hydrate (1.20 g, 24 mmol) was added and the resulting mixture heated at reflux for 2 h. Concentrated hydrochloric acid was added dropwise until a precipitate formed and the mixture was filtered. The flitrate was concentrated under reduced pressure and taken up in ethyl acetate, 1M sodium hydroxide added and the organic layer separated. The aqueous layer was extracted with ether and the organics were combined and concentrated under reduced pressure to give a brown oil. Chromatography (1% methanol in DCM) gave (4-fluorophenyl)-(2-thienyl)methylamine (2.4 g, 48%).

$\delta_H$ 7.44–7.36 (2H, m), 7.22 (1H, dd, J 5.1. 1.0 Hz), 7.08–7.00 (2H, m), 6.95 (1H, dd, J 5.0, 3.5 Hz), 6.85 (1H, dd, J 3.4, 0.9 Hz), 5.42 (1H, s), 2.11 (2H, s).

(c) N-Methyl-N-4-(1H-2-methylimidazo[4,5-c]pyridinylmethyl)phenylsulphonyl-1-(4-fluorophenyl)-1-(2-thienyl)methylamine N-Methyl-N-4-(1H-2-methylimidazo[4,5-c]pyridinylmethy l)phenylsulphonyl-1-(4-fluorophenyl)- 1-(2-thienyl)methylamine was prepared by the procedure of Example 131 employing (4-fluorophenyl)-(2-thienyl)methylamine as starting material.

Yellow amorphous solid (3% yield for the last step after chromatography (4% methanol in DCM) to separate the desired 1H-regioisomer from the 3H- and 5H-regioisomers):

i.r. (CDCl$_3$) 1605, 1510, 1340, 1230, 1160, 985 cm$^{-1}$ $\delta_H$ 9.06 (1H, br s), 8.50 (1H, br s), 7.67 (2H, d, J 8.2 Hz), 7.28–7.20 ( 3H, m), 7.11–7.06 (3H, m), 7.01–6.94 (2H, m), 6.85–6.82 (1H, m), 6.68 (1H, br s), 6.58 (1H, s), 5.37 (2H, s), 2.72 (3H, s), 2.59 (3H, s);

$\delta_C$ 164.27, 160.32, 154.60, 140.99, 140.63, 140.13, 139.35, 139.30, 133.62, 129.89, 129.76, 128.05, 127.91, 126.71, 126.56, 125.65, 115.45, 115.10, 59.75, 47.01, 30.65, 14.05.

EXAMPLE 135

N-4-(1H-2-Methylimidazo[4,5-c]pyridinylmethyl)phenylsulphonyl-1-(2thienyl)propylamine

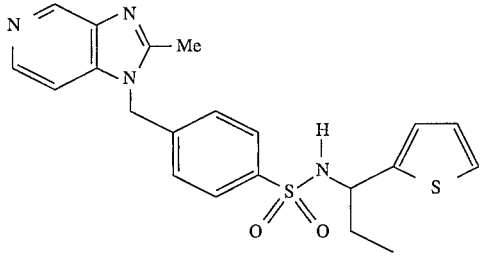

N-4-(1H-2-Methylimidazo[4,5-c]pyridinylmethyl)phenylsulphonyl-1-(2-thienyl)propylamine was prepared by the procedures of Example 134 Steps (a) and (b) and Example 131 Steps (a) and (c) employing ethyl-(2-thienyl)ketone as starting material.

White crystalline solid (4% yield for the last step after chromatography (5–8% methanol in DCM) to separate the desired 1H-regioisomer from the 3H- and 5H-regioisomers): m.p. 185°–186° C.

i.r. (CDCl$_3$) 1610, 1410, 1340, 1160, 1030 cm$^{-1}$ $\delta_H$ 9.00 (1H, s), 8.38 (1H, d, J 5.6 Hz), 7.63 (2H, d, J 8.3 Hz), 7.14 ( 1H, d, J 5.7 Hz), 6.99 (2H, d, J 8.3 Hz), 6.92 (1H, dd, J 3.4, 3.1 Hz), 6.67–6.64 (2H, m), 6.09 (1H, d, J 8.0 Hz), 5.33 (2H, s), 4.54 (1H, dr, J 7.5, 7.3 Hz), 2.57 (3H, s), 1.92–1.77 (2H, m), 0.86 (3H, t, J 7.3 Hz);

$\delta_C$ 153.69, 144.75, 141.42, 141.35, 141.15, 140.20, 139.52, 138.86, 127.46, 126.40, 126.12, 124.76, 124.23, 104.93, 55.15, 46.70, 31.08, 10.48.

EXAMPLE 136

N-Methyl-N-4-(1H-2-methylimidazo[4,5-c]pyridinylmethyl)phenylsulphonyl-1-(2-furyl)-3-methylbutylamine

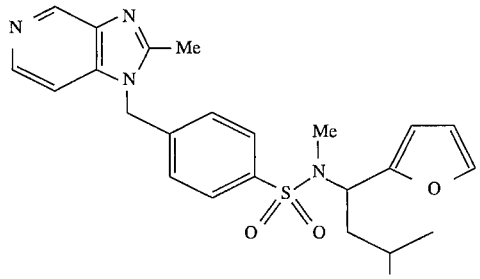

(a) 1-(2-Furyl)-3-methylbutanol

Furan was added dropwise to a stirred solution of n-butyllithium (2.5M in hexanes, 58.8 ml, 147 mmol) in dry THF (200 ml) at −20° C. under argon. The mixture was allowed to warm to room temperature and was then heated at reflux for 4 h. The mixture was cooled to −30° C. and isovaleraldehyde (12.8 g, 147 mmol) was added dropwise. The mixture was allowed to warm to room temperature and was then heated at reflux for 16 h. The reaction mixture was allowed to cool to room temperature, poured onto crushed ice, extracted with ether and the combined organic extracts dried over anhydrous potassium carbonate, filtered and concentrated to give a dark yellow oil. Distillation under reduced pressure gave 1-(2-furyl)-3-methylbutanol (11.0 g, 49%) as a colourless oil.

δ$_H$ 7.35 (1H, dd, J 1.8, 0.8 Hz), 6.31 (1H, dd, J 3.1, 1.8 Hz), 6.21 (1H, d, J 2.9 Hz), 4.73 (1H, t, J 6.8 Hz), 2.19 (1H, br s), 1.80–1.64 (3H, m), 0.94 (3H, d, J 6.2 Hz), 0.92 (3H, d, J 6.1 Hz).

(b) N-4-Bromomethylphenylsulphonyl-1-(2-furyl)-3-methylbutylamine

N-4-Bromomethylphenylsulphonyl-1-(2-furyl)-3-methylbutylamine was prepared by the procedures of Example 134 Step (b) and Example 1 Steps (b) and (d) employing 1-(2-furyl)-3-methylbutanol in lieu of (4-fluorophenyl)-(2-thienyl)methanol as starting material.

Yellow oil (26% yield for last step after chromatography (1:8 ethyl acetate/hexane)):

δ$_H$ 7.65 (2H, dd, J 6.5, 1.9 Hz), 7.38 (2H, dd, J 8.5, 2.1 Hz), 7.07 (1H, d, J 1.6 Hz), 6.07 (1H, dd, J 3.3, 1.7 Hz), 5.86 (1H, d, J 3.3 Hz), 4.84 (1H, d, J 8.8 Hz), 4.50–4.45 (1H, m), 4.45 (2H, s), 1.69–1.52 (3H, m), 0.88 (3H, d, J 6.4 Hz), 0.87 (3H, d, J 6.3 Hz).

(c) N-Methyl-N-4-(1H-2-methylimidazo[4,5-c]pyridinylmethyl)phenylsulphonyl-1-(2-furyl )-3-methylbutylamine N-Methyl-N-4-(1H-2-methylbenzimidazolylmethyl)phenylsulphonyl-1-(2-furyl)-3-methylbutylamine was prepared by the procedure of Example 131 Steps (b) and (c) employing N-4-bromomethylphenylsulphonyl-1-(2-furyl)-3-methylbutylamine in lieu of N-4-bromomethylphenylsulphonyl-2-thienylmethylamine.

Pale yellow oil (14.5% yield after chromatography (3–7% methanol in DCM)):

Analysis calculated for $C_{24}H_{28}N_4O_3S$ Requires C 63.69H 6.24N 12.38 Found C 63.14H 6.28N 12.23 i.r. (CDCl$_3$) 2960, 1610, 1345, 1150, 1015 cm$^{-1}$

δ$_H$ 8.98 (1H, s), 8.32 (1H, d, J 5.4 Hz), 7.66 (2H, d, J 8.2 Hz), 7.10 ( 1H, d, J 5.5 Hz), 7.06 (2H, d, J 8.3 Hz), 6.98–6.97 (1H, m), 6.08–6.06 (1H, m), 5.93 (1H, d, J 3.3 Hz), 5.12 (2H, s), 5.10–5.40 (1H, m), 2.55 (3H, s), 2.54 (3H, s), 1.63–1.52 (3H, m), 0.90–0.86 (6H, m);

EXAMPLE 137

N-4-(1H-2-Methylbenzimidazolylmethyl)phenylsulphonyl-1-(2-Benzothiazolyl)-3-methylbutylamine

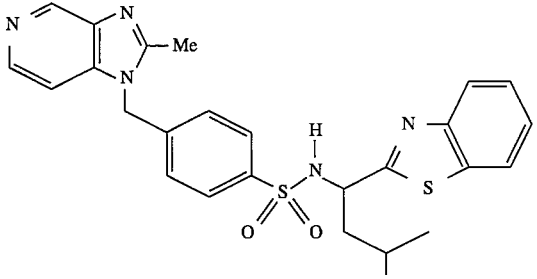

(a) 1-(2-Benzothiazolyl)-3-methylbutanol

A solution of n-butyllithium (2.5M in hexanes; 65.1 ml, 0.163 mol) was added to a stirred solution of benzothiazole (20.0 g, 0.148 mol) in dry THF (250 ml) under argon at −78° C. After 10 min a solution of isovaleraldehyde (17.4 ml, 0.163 mol) in dry THF (50 ml) was added slowly and the mixture stirred for 1 h at −78° C. The reaction mixture was removed from the cooling bath and after 10 min was quenched by the addition of excess water and the mixture extracted with ethyl acetate. The combined organic layers were washed with water, dried, filtered and evaporated. Chromatography (20–30% diethyl ether in hexane) gave 1-(2-benzothiazolyl)-3-methylbutanol (5.8 g, 18%) as an amorphous yellow solid.

δ$_H$ 7.99 (1H, dd, J 7.7, 1.0 Hz), 7.90 (1H, dd, J 7.8, 1.1 Hz), 7.48 (1H, ddd, J 8.3, 7.3, 1.2 Hz), 7.38 (1H, ddd, J 8.2, 7.4, 1.1 Hz), 5.16 (1H, dd, J 8.9, 5.1 Hz), 3.00 (1H, br s), 2.01–1.95 (1H, m), 1.89–1.82 (2H, m), 1.04 (3H, d, J 6.4 Hz), 1.03 (3H, d, J 6.5 Hz).

(b) 1-(2-Benzothiazolyl)-3-methylbutylamine 1-(2-Benzothiazolyl)-3-methylbutylamine was prepared by the procedure of Example 134 Step (b) employing 1-(2-benzothiazolyl)-3-methylbutanol in lieu of (4-fluorophenyl)-(2-thienyl)methanol as starting material.

Pale yellow oil (98% yield after chromatography (2–4% methanol in DCM)):

δ$_H$ 7.97 (1H, br d, J 8.4 Hz), 7.89 (1H, br d, J 7.7 Hz), 7.72–7.36 (2H, m), 6.66 (2H, br s), 4.43 (1H, dd, J 8.4, 5.4 Hz), 1.88–1.68 (3H, m), 1.01–0.97 (6H, m).

(c) N-4-Bromomethylphenylsulphonyl-1-(2-benzothiazolyl)-3-methylbutylamine

N-4-Bromomethylphenylsulphonyl-1-(2-benzothiazolyl)-3-methylbutylamine was prepared by the procedures of Example 1 Step (b) employing 1-(2-benzothiazolyl)-3-methylbutylamine in lieu of L-leucine ethyl ester hydrochloride as starting material.

δhd H 7.88–7.69 (2H, m), 7.72 (2H, d, J 8.4 Hz), 7.44 (1H, ddd, J 8.1, 7.4, 1.2 Hz), 7.37–7.31 (1H, m), 7.19 (2H, d, J 8.1 Hz), 5.58 (1H, d, J 9.0 Hz), 4.85–4.76 ( 1H, m), 4.27 (2H, s), 1.85–1.72 (3H, m), 0.94 (3H, d, J 6.6 Hz), 0.92 (3H, d, J 6.5 Hz).

(d) N-4-(1H-2-Methylbenzimidazolylmethyl)phenylsulphonyl-1-(2-benzothiazole)-3-methylbutylamine N-4-(1H-2-Methylbenzimidazolylmethyl)phenylsulphonyl-1-(2-benzothiazolyl)-3-methylbutylamine was prepared by the procedure of Example 131 Step (c) employing N-4-bromomethylphenylsulphonyl-1-(2-benzothiazolyl)-3-methylbutylamine in lieu of N-4-bromomethylphenylsulphonyl-2-thienylmethylamine.

Off-white crystalline solid (5% yield after chromatography (4–8% methanol in DCM) and crystallisation (ethyl acetate)): m.p. 195°–197° C.

Analysis calculated for $C_{24}H_{28}N_4O_3S$ Requires C 63.69H 6.24N 12.38 Found C 63.14H 6.28N 12.23 i.r. (CDCl$_3$) 2960, 1410, 1345, 1160, 1015 cm$^{-1}$ 67 $_H$ 9.03 (1H, br s), 8.37 (1H, br s), 7.82–7.70 (2H, m), 7.68 (2H, d, J 8.2 Hz), 7.44 (1H, ddd, J 7.7, 7.7, 1.4 Hz), 7.35 (1H, ddd, J 7.6, 7.6, 1.2 Hz), 6.98 (1H, br s), 6.84 (2H, d, J 8.3 Hz), 6.55 (1H, br s), 5.12 (2H, s), 4.83–4.80 (1H, m), 2.37 (3H, s), 1.84–1.70 (3H, m), 0.90 (3H, d, J 5.9 Hz), 0.89 (3H, d, J 5.9 Hz);

δ$_C$ 171.70, 153.57, 152.38, 141.70, 140.52, 140.33, 139.32, 134.60, 128.09, 126.21, 125.30, 122.80, 121.58, 104.50, 54.65, 46.58, 46.22, 24.53, 22.67, 21.59.

EXAMPLE 138–154

The compounds of Examples 138–154 are prepared by the procedure of Example 136 employing the appropriate organolithium reagent as starting material.

138. N-Methyl-N-4-(1H-2-methylimidazo[4,5-c]pyridinylmethyl)phenylsulphonyl-1-( 2-thienyl )-3-methylbutylamine 139. N-Methyl-N-4-(1H-2-methylimidazo[4,5-c]pyridinylmethyl)phenylsulphonyl-1-(pyridin- 3-yl)-3-methylbutylamine 140. N-Methyl-N-4-(1H-2-methylimidazo[4,5-c]pyridinylmethyl)phenylsulphonyl-1-(N'-methyl- 2-pyrrolyl)-3-methylbutylamine 141. N-Methyl-N-4-(1H-2-methylimidazo[4,5-c]pyridinylmethyl)phenylsulphonyl-1-(pyrazin-2-yl)-3-methylbutylamine
142. N-Methyl-N-4-(1H-2-methylimidazo[4,5-c]pyridinylmethyl)phenylsulphonyl-1-(6-methylpyrazin-2-yl)-3-methylbutylamine
143. N-Methyl-N-4-(1H-2-methylimidazo[4,5-c]pyridinylmethyl)phenylsulphonyl-1-(6-ethylpyrazin-2-yl)-3-methylbutylamine
144. N-Methyl-N-4-(1H-2-methylimidazo[4,5-c]pyridinylmethyl)phenylsulphonyl-1-(6-ethyl-1,2-pyridazin-3-yl)-3-methylbutylamine
145. N-Methyl-N-4-(1H-2-methylimidazo[4,5-c]pyridinylmethyl)phenylsulphonyl-1-(2-ethyl-1,3-pyrimidin-5-yl)-3-methylbutylamine
146. N-Methyl-N-4-(1H-2-methylimidazo[4,5-c]pyridinylmethyl)phenylsulphonyl-1-(1,3-dithian-2-yl)-3-methylbutylamine
147. N-Methyl-N-4-(1H-2-methylimidazo[4,5-c]pyridinylmethyl)phenylsulphonyl-1-(2-thienyl)pentylamine
148. N-Methyl-N-4-(1H-2-methylimidazo[4,5-c]pyridinylmethyl)phenylsulphonyl-1-(4-fluorophenyl)-1-(2-furyl)methylamine
149. N-Methyl-N-4-(1H-2-methylimidazo[4,5-c]pyridinylmethyl)phenylsulphonyl-2-(4-methoxyphenyl)-1-(2-furyl)ethylamine
150. N-Methyl-N-4-(1H-2-methylimidazo[4,5-c]pyridinylmethyl)phenylsulphonyl-1-(pyridin-2-yl)-3-methylbutylamine
151. N-Methyl-N-4-(1H-2-methylimidazo[4,5-c]pyridinylmethyl)phenylsulphonyl-1-(2-methoxypyridin-3-yl)-3-methylbutylamine
152. N-Methyl-N-4-(1H-2-methylimidazo[4,5-c]pyridinylmethyl)phenylsulphonyl-1-(pyridin-3-ylmethyl)-3-methylbutylamine
153. N-Methyl-N-4-(1H-2-methylimidazo[4,5-c]pyridinylmethyl)phenylsulphonyl-1-(2-benzo[b]thienyl)-3-methylbutylamine
154. N-Methyl-N-4-(1H-2-methylimidazo[4,5-c]pyridinylmethyl)phenylsulphonyl-1-(3-methylisoxazol-5-ylmethyl)-3-methylbutylamine

EXAMPLE 155

N-Methyl-N-4-(1H-2-methylbenzimidazolylmethyl)phenylsulphonyl-1-( 3-methyl-1,2,4-oxadiazol-5-yl)-3-methylbutylamine

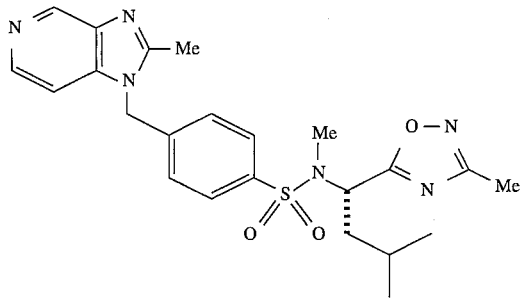

(a) N-Methyl-N-4-(1H-2-methylimidazo[4,5-c]pyridinylmethyl)phenylsulphonyl-L-leucine amide Aqueous ammonia (160 ml) was added to a stirred solution of N-methyl-N-4-(1H-2-methylimidazo[4,5-c]pyridinylmethyl)phenylsulphonyl-L-leucine ethyl ester (2.0 g, 4.4 mmol) in methanol (80 ml). The reaction mixture was stirred overnight at room temperature, the solvent removed under reduced pressure and the residue azeotroped with toluene to give crude N-Methyl-N-4-(1H-2-methylimidazo[4,5-c]pyridinylmethyl)phenylsulphonyl-L-leucine amide (1.86 g, 99%) as a yellow solid. Chromatography (10% methanol in DCM) followed by crystallisation from acetonitrile gave pure product as a white crystalline solid.

m.p. 198°–200° C.

Analysis calculated for $C_{21}H_{27}N_5O_3S$ Requires C 58.72H 6.34N 16.30 Found C 58.72H 6.37N 16.46 i.r. (MeCN) 3470, 3350, 1690, 1180 cm$^{-1}$ $\delta_H$ (CD$_3$OD) 8.31 (1H, s), 8.27 (1H, d, J 5.7 Hz), 7.78 (2H, d, J 8.4 Hz), 7.74 (1H, d, J 5.8 Hz), 7.27 (2H, d, J 8.4 Hz), 5.61 (2H, s), 4.42 (1H, dd, J 8.9, 6.1 Hz), 2.85 (3H, s), 2.59 (3H, s), 1.55–1.23 (5H, m), 0.82 (3H, d, J 6.2 Hz), 0.80 (3H, d, J 6.2 Hz).

(b) N-Methyl-N-4-(1H-2-methylimidazo[4,5-c]pyridinylmethyl)phenylsulphonyl-1-(3-methyl-1,2,4-oxadiazol-5-yl)-3-methylburylamine A mixture of N-methyl-N-4-(1H-2-methylimidazo[4,5-c]pyridinylmethyl)phenylsulphonyl-L-leucine amide (1.50 g, 3.5 mmol) in N,N-dimethylacetamide dimethyl acetal (5 ml) was heated at reflux for 2.5 h under argon. The volatiles were removed under reduced pressure and the residue treated with a solution of hydroxylamine hydrochloride (365 mg, 5.25 mmol) in 1M aqueous sodium hydroxide (5.25 ml). Dioxan (5 ml) was added, followed by acetic acid (10 ml) and the resulting solution stirred at room temperature for 0.5 h and then heated at 90° C. overnight. The reaction mixture was concentrated, diluted with saturated aqueous potassium carbonate and extracted with DCM, dried and evaporated. Chromatography (6% methanol in DCM) gave N-methyl-N-4-(1H-2-methylimidazo[4,5-c]pyridinylmethyl)phenylsulphonyl-1-(3-methyl-1,2,4-oxadiazol-5-yl)-3-methylbutylamine as a white foam (215 mg, 13%).

Analysis calculated for $C_{23}H_{32}N_6O_3S.0.7H_2O$ Requires C 58.96H 6.02N 17.94 Found C 57.50H 6.06N 17.15 i.r. (DCM) 2930, 1610, 1585, 1340, 1150 cm$^{-1}$ $\delta_H$ 9.05 (1H, s), 8.40 (1H, br d), 7.74 (2H, d, J 8.3 Hz), 7.18 (1H, d, J 5.4 Hz), 7.12 (2H, d, J 8.4 Hz), 5.39 (2H, s), 5.39–5.30 (1H, m), 2.81 (3H, s), 2.60 (3H, s), 2.19 (3H, s), 1.84–1.65 (3H, m), 0.99 (3H, d, J 6.1 Hz), 0.97 (3H, d, J 6.2 Hz).

EXAMPLE 156

N-Methyl-N-4-(1H-2-methylimidazo[4,5-c]pyridinylmethyl)phenylsulphonyl-1(3-ethyl- 1,2,4-oxadiazol-5-yl)-3-methylbutylamine

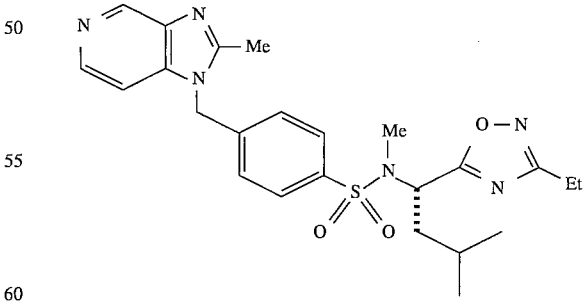

(a) N-Methyl-N-4-(1H-2-methylimidazo[4,5-c]pyridylmethyl)phenylsulphonyl-L-leucine A solution of N-methyl-N-4-(1H-2-methylimidazo[4,5-c]pyridylmethyl)phenylsulphonyl-L-leucine ethyl ester (6.00 g, 13 mmol) in 8M hydrochloric acid (100 ml) was refluxed for 3 hours. The reaction mixture was concentrated to an orange gum which was taken up in ethyl acetate and evaporated to dryness, to give N-methyl-N-4-(1H-2-methylimidazo[4,5-c]pyridylmethyl)phenylsulphonyl-L-leucine (5.30 g, 94%) as a pale yellow solid. i.r. (KBr) 3660–3150, 1720–1695, 1610, 1325, 1145 cm$^{-1}$ $\delta_H$ (CD$_3$OD) 8.36 (1H, s), 8.29 (1H, d, J 5.7 Hz), 7.77 (2H, d, J 8.4 Hz), 7.56 (1H, d, J 5.7 Hz), 7.27 (2H, d, J 8.3 Hz), 5.61 (2H, s), 4.55–4.49 (1H, m), 2.79 (3H, s), 2.59 (3H, s), 1.64–1.46 (3H, m), 0.89 (3H, d, J 6.0 Hz), 0.88 (3H, d, J 5.8 Hz).

(b) N-Methyl-N-4-(1H-2-methylimidazo[4,5-c]pyridinylmethyl)phenylsulphonyl-L-leucine pentafluorophenyl ester N-Methyl-N-4-(1H-2-methylimidazo[4,5-c]pyridinylmethyl)phenylsulphonyl-L-leucine pentafluorophenyl ester was prepared by the procedure of Example 78 Step (a) employing N-methyl-N-4-(1H-2-methylimidazo[4,5-c]pyridinylmethyl)phenylsulphonyl-L-leucine in lieu of 2-(3,4-dimethoxyphenylmercapto)ethanoate.

$\delta_H$ 8.98 (1H, s), 8.31 (1H, d, J 5.8 Hz), 7.78 (2H, d, J 8.3 Hz), 7.23 (1H, d, 5.8 Hz), 7.16 (2H, d, J 8.3 Hz), 5.44 (2H, s), 5.09–5.03 (1H, m), 2.89 (3H, s), 2.58 (3H, s), 1.86–1.65 (3H, m), 1.03 (3H, d, J 5.5 Hz), 1.01 (3H, d, J 5.1 Hz).

(c) N-Methyl-N-4-(1H-2-methylimidazo[4,5-c]pyridinylmethyl)phenylsulphonyl-1-(3-ethyl-1,2,4-oxadiazol-5-yl)-3-methylbutylamine A solution of N-methyl-N-4-(1H-2-methylimidazo[4,5-c]pyridinylmethyl)phenylsulphonyl-L-leucine pentafluorophenyl ester (1.60 g, 2.7 mmol) in chloroform (50 ml) was treated with propionamide oxime (0.28 g, 3.2 mmol) and heated at reflux for 10 h. The mixture was cooled, washed with saturated aqueous sodium hydrogen carbonate and brine, dried, filtered and concentrated. The residue was dissolved in ethyl acetate and heated at reflux over activated molecular sieves. The reaction mixture was filtered and concentrated. Chromatography (7% methanol in DCM) gave N-methyl-N-4-(1H-2-methylimidazo[4,5-c]pyridinylmethyl)phenylsulphonyl-1-(3-ethyl-1,2,4-oxadiazol-5-yl)-3-methylbutylamine (673 mg, 52%) as a brown oil. A portion was further purified by reverse phase preparative HPLC (C-18 silica; 50–80% 0.01 M ammonium acetate in methanol) to give N-methyl-N-4-(1H-2-methylimidazo[4,5-c]pyridinylmethyl)phenylsulphonyl-1-(3-ethyl-1,2,4-oxadiazol-5-yl)-3-methylbutylamine as a white solid.

i.r. (CDCl$_3$) 2965, 1615, 1585, 1345, 1165 cm$^{-1}$ $\delta_H$ 9.00 (1H, s) 8.35 (1H, d, J 5.6 Hz), 7.67 (2H, d, J 8.3 Hz), 7.12 (1H, d, J 5.4 Hz), 7.06 (2H, d, J 8.3 Hz), 5.38–5.32 (1H, m), 5.34 (2H, s), 2.78 (3H, s), 2.55 (3H, s), 2.50 (2H, q, J 7.5 Hz), 2.13–1.62 (3H, m), 1.11 (3H, t, J 7.6 Hz), 0.95 (3H, d, J 5.9 Hz), 0.94 (3H, d, J 6.2 Hz);

$\delta_C$ 176.58, 171.19, 153.19, 142.17, 142.05, 140.14, 139.98, 139.84, 138.79, 128.18, 126.58, 104.52, 51.58, 46.72, 39.56, 29.54, 24.22, 22.63, 21.35, 19.37, 13.82, 11.07.

EXAMPLE 157

N-Methyl-N-4-(1H-2-methylimidazo[4,5-c]pyridinylmethyl)phenylsulphonyl-1-(3-octadecyl-1,2,4-oxadiazol-5-yl)-3-methylbutylamine

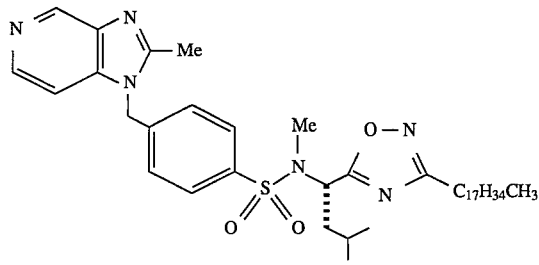

N-Methyl-N-4-(1H-2-methylimidazo[4,5-c]pyridinylmethyl)phenylsulphonyl-1-(3-octadecyl- 1,2,4-oxadiazol-5-yl)-3-methylbutylamine was prepared by the procedure of Example 156 employing octadecylamide oxime in lieu of propionamide oxime.

Pale brown oil (21% yield after chromatography (5–8.5% methanol in DCM)):

i.r. (CDCl$_3$) 2930, 1585, 1350, 1155 cm$^{-1}$ $\delta_H$ 9.00 (1H, s), 8.35 (1H, d, J 4.9 Hz), 7.68 (2H, d, J 8.4 Hz), 7.12 (1H, d, J 5.5 Hz), 7.07 (2H, d, J 8.4 Hz), 5.38–5.31 (3H, m), 2.77 (3H, s), 2.55 (3H, s), 2.49 (2H, dd, J 7.9, 7.3 Hz), 1.81–1.52 (5H, m), 1.36–1.17 (32H, m), 0.96 (3H, d, J 6.1 Hz), 0.94 (3H, d, J 6.3 Hz), 0.85 (3H, t, J 6.6 Hz);

$\delta_C$ 176.49, 170.32, 153.29, 142.11, 141.95, 140.17, 139.95, 139.86, 138.73, 128.18, 126.59, 104.59, 51.52, 46.73, 39.51, 31.80, 29.57, 29.36, 29.23, 29.07, 8.95, 26.76, 25.66, 24.22, 22.66, 22,56, 21.37, 13.99, 13.86.

EXAMPLES 158–161

The compounds of Example 158–161 are prepared by the procedure of Example 156 employing the appropriate amide oxime in lieu of propionamide oxime.

158. N-Methyl-N-4-(1H-2-methylimidazo[ 4,5-c]pyridinylmethyl)phenylsulphonyl-1-(3-propyl-1,2,4-oxadiazol-5-yl)-3-methylbutylamine
159. N-Methyl-N-4-(1H-2-methylimidazo[ 4,5-c]pyridinylmethyl)phenylsulphonyl-1-(3-n-butyl-1,2,4-oxadiazol-5-yl)-3-methylbutylamine
160. N-Methyl-N-4-(1H-2-methylimidazo[ 4,5-c]pyridinylmethyl)phenylsulphonyl-1-(3-phenyl-1,2,4-oxadiazol-5-yl)-3-methylbutylamine
161. N-Methyl-N-4-(1H-2-methylimidazo[ 4,5-c]pyridinylmethyl)phenylsulphonyl-1-(3-benzyl-1,2,4-oxadiazol-5-yl )-3-methylbutylamine

EXAMPLE 162

N-Methyl-N-4-(1H-2-methylimidazo[ 4,5-c]pyridinylmethyl)phenylsulphonyl-1(5-methyl-1,3,4-oxadiazol-2-yl)-3-methylbutylamine

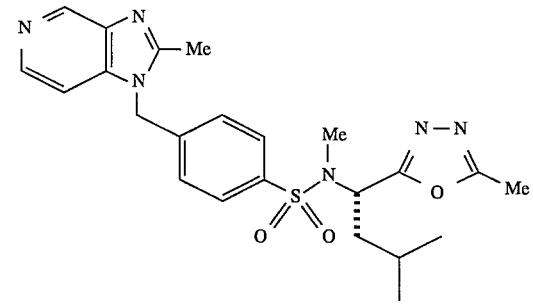

Excess hydrazine hydrate (1.7 ml) was added to a solution of N-methyl-N-4(1H-2-methylimidazo[4,5-c]pyridinylmethyl)phenylsulphonyl-L-leucine ethyl ester (2.00 g, 4.4 mmol) in toluene (3 ml) and the mixture heated at reflux for 7 days. The mixture was cooled and triethylorthoacetate (10 ml) was added and the resulting mixture heated at reflux overnight. The volatiles were removed under reduced pressure and the residue partitioned between ethyl acetate and saturated aqueous sodium hydrogen carbonate. The organic layer was separated and washed with brine, dried, filtered and evaporated. The residue was filtered through a pad of silica (eluting with 6% methanol in DCM) to give a pale pink oil, which was then heated at ca. 160° C. for 24 h under argon. Chromatography (5% methanol in DCM) gave N-Methyl-N-4-(1H-2-methylimidazo[4,5-c]pyridinylmethyl)phenylsulphonyl-1-5-methyl-1,3,4-oxadiazol-2-yl )-3-methylbutylamine (257 mg, 13%) as a yellow oil.

i.r. (DCM) 1610, 1590, 1340, 1150 cm$^{-1}$ $\delta_H$ 8.94 (1H, s), 8.29 (1H, d, J 5.4 Hz), 7.64 (2H, d, J 8.4 Hz), 7.09 (1H, d, J 5.6 Hz), 7.04 (2H, d, J 8.3 Hz), 5.32 (2H, s), 5.29–5.23 (1H, m), 2.69 (3H, s), 2.51 (3H, s), 2.22 (3H, s), 1.70–1.64 (2H, m), 1.59–1.49 (1H, m), 0.87 (3H, d, J 6.3 Hz), 0.85 (3H, d, J 6.5 Hz);

$\delta_C$ 164.21, 163.55, 153.26, 141.69, 141.65, 139.98, 139.60, 138.55, 104.56, 53.30, 50.58, 46.54, 38.78, 29.29, 24.04, 22.44, 21.37, 13.77, 10.51.

EXAMPLES 163–165

The compounds of Example 163–165 are prepared by the procedure of Example 162 employing the appropriate trialkylortho ester deivative in lieu of triethylorthoacetate.

163. N-Methyl-N-4-(1H-2-methylimidazo[4,5-c]pyridinylmethyl)phenylsulphonyl-1-(5-ethyl-1,3,4-oxadiazol-2-yl)-3-methylbutylamine
164. N-Methyl-N-4-(1H-2-methylimidazo[4,5-c]pyridinylmethyl)phenylsulphonyl-1-(5-propyl-1,3,4-oxadiazol-2-yl)-3-methylbutylamine
165. N-Methyl-N-4-(1H-2-methylimidazo[4,5-c]pyridinylmethyl)phenylsulphonyl-1-(5-phenyl-1,3,4-oxadiazol-2-yl)-3-methylbutylamine

EXAMPLE 166

N-Methyl-N-4-(1H-2-methylimidazo[4,5-c]pyridinylmethyl)phenylsulphonyl-β-alanine ethyl ester

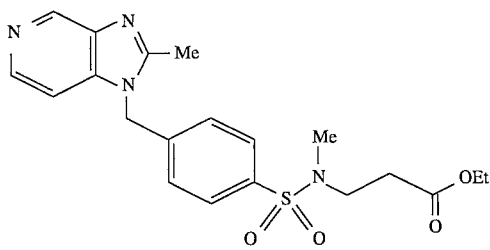

N-Methyl-N-4-(1H-2-methylimidazo[4,5-c]pyridinylmethyl)phenylsulphonyl-β-alanine ethyl ester was prepared by the procedures of Example 1 Steps (b) and (d) and Example 131 Step (c) employing β-alanine ethyl ester hydrochloride as starting material.

Colourless oil (10% yield for last step after chromatography (5% methanol in DCM)):

i.r. (CDCl$_3$) 1725, 1340, 1160 cm$^{-1}$ $\delta_H$ 8.93 (1H, br s), 8.27 (1H, d, J 5.5 Hz), 7.63 (2H, d, J 8.3 Hz), 7.14–7.06 (3H, m), 5.34 (2H, s), 4.02 (2H, q, J 7.1 Hz), 3.21 (2H, t, J 7.2 Hz), 2.67 (3H, s), 2.51 (3H, s), 2.50 (2H, t, J 7.1 Hz), 1.15 (3H, t, J 7.2 Hz);

$\delta_C$ 170.81, 153.32, 141.62, 141.58, 140.05, 139.89, 137.40, 132.15, 128.30, 127.96, 126.77, 104.61, 60.60, 46.55, 45.88, 35.28, 33.49, 13.90.

EXAMPLES 167–172

The compounds of Example 167–172 are prepared by the procedure of Example 166 employing the appropriate amino acid derivative in lieu of β-alanine ethyl ester hydrochloride 167. N-Methyl-N-4-(1H-2-methylimidazo[4,5-c]pyridinylmethyl)phenylsulphonyl-3-amino-5-methylhexanoic acid ethyl ester
168. N-Methyl-N-4-(1H-2-methylimidazo[4,5-c]pyridinylmethyl)phenylsulphonyl-3-amino-5-methylhexanoic acid isopropyl ester
169. N-Methyl-N-4-(1H-2-methylimidazo[4,5-c]pyridinylmethyl)phenylsulphonyl-3-amino-5-methylhexanoic acid n-butyl ester
170. N-Methyl-N-4-(1H-2-methylimidazo[4,5-c]pyridinylmethyl)phenylsulphonyl-3-amino-5-methylhexanoic acid benzyl ester
171. N-Methyl-N-4-(1H-2-methylimidazo[4,5-c]pyridinylmethyl)phenylsulphonyl-3-amino-4-phenylbutanoic acid ethyl ester
172. N-Methyl-N-4-(1H-2-methylimidazo[4,5-c]pyridinylmethyl)phenylsulphonyl-3-amino-4-(4-methoxyphenyl)butanoic acid ethyl ester

Comparative Example

N-Cyclohexyl-N-methyl-4-(1H-imidazo[4,5-c]pyridinylmethyl)benzamide

This compound is not within the scope of the invention: It has been included here as a comparative example. This compound was described in EP-A-0260613.

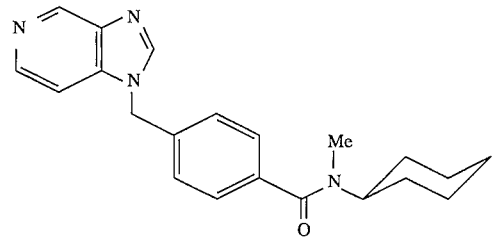

Comparative Example (a) N-Cyclohexyl-N-methyl-4-methylbenzamide

To an ice cold stirred solution of N-methylcylohexylamine (20 ml, 0.15 mol) and triethylamine (22 ml) in dry THF (100 ml) under argon was slowly added p-toluoyl chloride (20 ml, 0.15 mol). A white precipitate formed. The ice bath was removed and the mixture stirred at ambient temperature for 24 h. Ice cold 2M hydrochloric acid (100 ml) was added and the organic layer separated. The aqueous layer was extracted with ethyl acetate (3×100 ml). The combined organics were washed with brine (3×100 ml), dried, filtered and evaporated to give the crude amide, which was crystallised from hexane to give N-cyclohexyl-N-methyl-4-methylbenzamide (30.9 g, 87%) as a white crystalline solid.

m.p. 70°–71 ° C.

i.r. (nujol) 2920, 1640 cm$^{-1}$ $\delta_H$ 7.26 (2H, d, J 8.0 Hz), 7.18 (2H, d, J 8.3 Hz), 4.50, 3.50 (1H, 2br m), 3.08–2.68 (3H, br m), 2.37 (3H, s), 1.93–0.93 (10H, br m).

(b) N-Cyclohexyl-N-methyl-4-bromomethylbenzamide

Utilising the procedure described in Example 1 Step (a) employing N-cyclohexyl-N-methyl-4-methylbenzamide in lieu of p-toluene-sulphonyl chloride and tetrachloromethane as solvent yielded crude N-cyclohexyl-N-methyl-4-bromomethylbenzamide (67%) as an orange waxy solid.

i.r. (CH$_2$Cl$_2$) 2935, 1720 cm$^{-1}$ $\delta_H$ 7.46 (2H, d, J 8.1 Hz), 7.34 (2H, d, J 8.1 Hz), 4.51 (2H, s), 3.78, 3.50 (1H, 2br m), 2.97 (3H, br s), 1.89–0.98 (10H, br m).

(c) N-Cyclohexyl-N-methyl-4-(1H-imidazo[4,5-c]pyridinylmethyl)benzamide

Sodium bis(trimethylsilyl)amide (22 ml of 1M solution in THF) was added to a stirred solution of imidazo[4,5-c]pyridine (2.60 g, 0.02 mol) in dry THF (200 ml) under argon. A fine white precipitate formed. After 90 m the mixture was treated with N-cyclohexyl-N-methyl-4-bromomethylbenzamide (6.20 g, 0.02 mol) dissolved in dry THF (50 ml). The mixture was allowed to warm to ambient temperature and stirred overnight. Methanol (1 ml) was added, followed by water and the product extracted using ethyl acetate (3×150 ml). The combined organic layers were washed with water (2×100 ml), dried over anhydrous potassium carbonate and the solvent removed to give the crude product. Chromatography (10% methanol in ethyl acetate) followed by repeated fractional crystallisation (6 times from ethyl acetate/DIPE) gave the desired regioisomer N-cyclohexyl-N-methyl-4-(1H-imidazo[4,5-c]pyridinylmethyl)benzamide (0.39 g, 5%) as an off white crystalline solid.

m.p. 121–123° C.

Analysis calculated for C$_{21}$H$_{24}$N$_4$O.0.6H$_2$O Requires C 70.21H 7.07N 15.60 Found C 70.08H 6.91N 15.37 i.r. (KBr) 3080, 2930, 1615 cm$^{-1}$ $\delta_H$ 9.17 (1H, s), 8.42 (1H, d, J 5.6 Hz), 8.03 (1H, s), 7.37 (2H, d, J 7.8 Hz), 7.27–7.19 (3H, m), 5.42 (2H, s), 4.50, 3.37 (1H, 2br m), 2.96, 2.76 (3H, 2br, s), 2.05–1.02 (10H, br m).

Pharmacology Example 1

The inhibition of [$^3$H]-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at –70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained [$^3$H]-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5 mM MgCl$_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples.

After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

Inhibition=[(TB–TBA)/SB]×100 where the specific binding SB=TB–NSB

Table 1 lists results from this assay for inhibition of [$^3$H]-PAF receptor binding for illustrative examples of the compounds of this invention. Also presented in Table 1 is the result for a comparative example (N-cyclohexyl-N-methyl-4-(1H-imidazo[4,5-c]pyridinylmethyl)benzamide. This compound (a PAF antagonist described in EP-A-0260613) is not within the scope of the invention.

TABLE 1

| Results for inhibition of [$^3$H]-PAF receptor binding | |
|---|---|
| Example | Inhibition of [$^3$H]-PAF binding IC$_{50}$ nM |
| 1 | 7 |
| 44 | 1 |
| 45 | 0.5 |
| 47 | 2 |
| 49 | 2 |
| 79 | 4 |
| 109 | 3 |
| 155 | 2 |
| Comparative Example | 10,000 |

Pharmacology Example 2

The activity of the compounds of general formula I is also demonstrated in vivo by their ability to reverse the hypotension caused by an infusion of PAF in rats. Male Sprague-Dawley rats (300–350 g) were anaesthetised with a mixture of sodium pentobarbitone, 22.5 mg/kg and thiopental 62.5 mg/kg. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng/kg/min was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response ($ED_{50}$) calculated by straight line interpolation and the results are presented in Table 2.

TABLE 2

Results for inhibition of PAF-induced hypotension in the rat

| Example | $ED_{50}$ (μg/kg i.v.) |
| --- | --- |
| 44 | 4.6 |
| 49 | 2.2 |
| 78 | 5.8 |
| 108 | 6.6 |
| 156 | 0.6 |
| Comparative Example | 150 |

We claim:

1. A compound of general formula I:

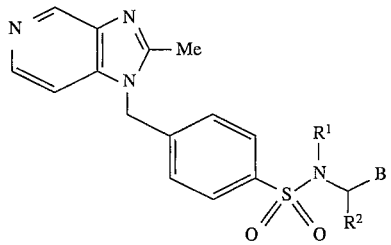

wherein:

$R^1$ represents hydrogen, —$C_1$-$C_6$ alkyl, —$C_2$-$C_6$ alkenyl, —$C_2$-$C_6$ alkynyl, —$COC_1$-$C_6$ alkyl, —$CO_2C_1$-$C_6$ alkyl, —($COC_1$-$C_6$ alkyl) phenyl, —$CO_2C_1$-$C_6$ alkyl)phenyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)$CO_2C_1$-$C_6$ alkyl, —$C_3$-$C_8$ cycloalkyl, —$C_4$-$C_8$ cycloalkenyl or a group —D wherein D represents a group:

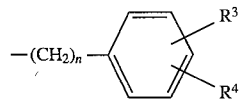

wherein n is an integer from 0 to 3, and each of $R^3$ and $R^4$ is independently hydrogen, —$C_1$-$C_6$ alkyl, —$C_2$-$C_6$ alkenyl, —$C_2$-$C_6$ alkynyl, halogen, —CN, —$CO_2H$, —$CO_2C_1$-$C_6$ alkyl, —$CONH_2$, —$CONHC_1$-$C_6$ alkyl, —$CONH(C_1$-$C_6$ alkyl)$_2$, —CHO, —$CH_2OH$, —$CF_3$, —$OC_1$-$C_6$ alkyl, —$SC_1$-$C_6$ alkyl, —$SOC_1$-$C_6$ alkyl, —$SO_2C_1$-$C_6$ alkyl, —$NH_2$ or —NHCOMe;

$R^2$ represents hydrogen, halogen, —$C_1$-$C_6$ alkyl optionally substituted by one or more halogen atoms, —$C_2$-$C_6$ alkenyl, —$C_2$-$C_6$ alkynyl, —($C_1$-$C_6$ alkyl)$CO_2C_1$-$C_6$ alkyl, —($C_1$-$C_6$ alkyl)$SC_1$-$C_6$ alkyl, —($C_1$-$C_6$ alkyl)$OC_1$-$C_6$ alkyl, —($C_1$-$C_6$ alkyl)$N(C_1$-$C_6$ alkyl)$_2$, —$C_3$-$C_8$ cycloalkyl, —$C_4$-$C_8$ cycloalkenyl, —($C_1$-$C_6$ alkyl)$C_3$-$C_8$ cycloalkyl, —($C_1$-$C_6$ alkyl)$C_4$-$C_8$ cycloalkenyl, —($C_1$-$C_6$ alkyl)$OC_3$-$C_8$ cycloalkyl, —($C_1$-$C_6$ alkyl)$OC_4$-$C_8$ cycloalkenyl, —($C_1$-$C_6$ alkyl)$SC_3$-$C_8$ cycloalkyl, —($C_1$-$C_6$ alkyl)$SC_4$-$C_8$ cycloalkenyl, a side chain of a naturally occurring amino acid, a group —D as defined above or a —($C_1$-$C_6$ alkyl)OD group wherein D is as defined above;

B represents a) a —$(CH_2)_mX$ group wherein m is an integer from 0 to 2 and the group X represents a 5- or 6-membered heterocyclic ring, which heterocyclic ring may be optionally fused to a benzene ring or to a further 5-, 6- or 7-membered heterocyclic ring containing one or more nitrogen atoms wherein the latter heterocyclic ring may also contain an oxygen or sulfur atom, and wherein any of the rings may be optionally substituted with one or more substituents selected from the group consisting of hydrogen, halogen, —$C_1$-$C_4$ perfluoroalkyl, hydroxyl, carbonyl, thiocarbonyl, carboxyl, —$CONH_2$, a group —D wherein D is as defined above, —$R^5$, —$OR^5$, —$SR^5$, —$SOR^5$, —$SO_2R^5$, —$NHR^5$, —$NR^5R^5$, —$CO_2R^5$ and —$CONHR^5$ wherein $R^5$ is —$C_1$-$C_{18}$ alkyl, —$C_2$-$C_6$ alkenyl, —$C_2$-$C_6$ alkynyl, —$C_3$-$C_8$ cycloalkyl or —$C_4$-$C_8$ cycloalkenyl each of which is optionally substituted with one or more substituents selected from the group consisting of halogen, hydroxyl, amino, carboxyl, —$C_1$-$C_4$ perfluoroalkyl, —$C_1$-$C_6$ alkyl, —$C_2$-$C_6$ alkenyl, —$C_2$-$C_6$ alkynyl, —$C_3$-$C_8$ cycloalkyl, —$C_4$-$C_8$ cycloalkenyl, —$OC_1$-$C_6$ alkyl, —$SC_1$-$C_6$ alkyl, tetrazol-5-yl, a group —D wherein D is as defined above and a heteroaryl or heteroarylmethyl group;

b) a group Y, wherein Y is —$CH_2OH$, —$CH_2OC(=O)R^6$, —$CH_2OC(=O)C(=O)OR^6$, —$CH_2OSO_2R^6$, —$CH_2OP(=O)OR^6OR^6$, —$NHC(C=O)OR^6$, —$CH_2OC(=O)NHR^6$, —$CH_2CO_2R^6$ or —$CH_2OC(=O)CH_2SR^6$ group wherein $R^6$ is, —$C_1$-$C_{18}$ alkyl, —$C_2$-$C_{20}$ alkenyl, —$C_2$-$C_{18}$ alkynyl, —($C_1$-$C_6$ alkyl)$OC_1$-$C_6$ alkyl, —($C_1$-$C_6$ alkyl)$SC_1$-$C_6$ alkyl, —($C_1$-$C_6$ alkyl)O($C_1$-$C_6$ alkyl)$OC_1$-$C_6$ alkyl, —$C_3$-$C_8$ cycloalkyl, —$C_4$-$C_8$ cycloalkenyl, a group D as defined above or a group —$(CH_2)_mX$ as defined above;

c) a —$CH_2OC(=O)CHR^2Y$ group wherein $R^2$ and Y are as defined above.

2. The compound of claim 1, wherein $R^1$ represents a hydrogen atom, a —$C_1$-$C_6$ alkyl group, a —$C_2$-$C_6$ alkenyl group or a group —D.

3. The compound of claim 1 wherein $R^2$ represents a hydrogen atom a —$C_1$-$C_6$ alkyl group, a —$C_2$-$C_6$ alkenyl group, a —($C_1$-$C_6$ alkyl)$C_3$-$C_8$ cycloalkyl group, a side chain of a naturally occurring amino acid or a group D.

4. The compound of claim 1, containing a group D wherein $R^3$ represents a hydrogen atom, a —$C_1$-$C_6$ alkyl group, a halogen atom, a —$CF_3$ group or a —$OC_1$-$C_6$ alkyl group, and $R^4$ represents a hydrogen atom or a —$OC_1$-$C_6$ alkyl group.

5. The compound of claim 1, wherein B is a group —$(CH_2)_mX$ wherein m is as defined in claim 1 and X represents a furanyl group, a thienyl group, a pyrrolinyl group, a tetrahydrofuranyl group, an oxadiazolyl group, a thiadiazolyl group, a pyridinyl group, a piperazinyl group, a benzotriazolyl group, a pyrazinyl group, a pyridazinyl group, a pyrimidinyl group, a dithianyl group, a benzo[b]thienyl group, a isoxazolyl group or a quinolinyl group.

6. The compound of claim 5, wherein the group X is substituted with one or more substituents selected from the group consisting of: hydrogen, a group —D, —$R^5$ and —$CO_2R^5$, wherein D and $R^5$ are as defined in claim 1.

7. The compound of claim 6, wherein $R^5$ represents a —$C_1$–$C_{18}$ alkyl group or a —$OC_1$–$C_6$ alkyl group.

8. The compound of claim 1, wherein B is a group Y as defined in claim 1 wherein $R^6$ represents a —$C_1$–$C_{18}$ alkyl group, a —$C_2$–$C_{20}$ alkenyl group, a group —D or a group —$(CH_2)_mX$ as defined in claim 1 or in any one of claims 5 to 7.

9. The compound of claim 1, wherein $R^1$ is hydrogen or methyl, $R^2$ is sec-butyl (side chain of L-leucine) and B is a group —$(CH_2)_mX$ as defined in claim 1 or a group Y wherein Y is a —$CH_2OH$, —$CH_2OC(=O)R^6$, —$CH_2OC(=O)NHR^6$ or —$CH_2OC(=O)CH_2SR^6$ group.

10. A compound selected from the group consisting of:
N-Methyl-N-4-(1H-2-methylimidazo[4,5-c]pyridinylmethyl)phenylsulphonyl-L-leucinol,
N-4-(1H-2-Methylimidazo[4,5-c]pyridinylmethyl)phenylsulphonyl-L-leucinol,
N-Methyl-N-4-(1H-2-methylimidazo[4,5-c]pyridinylmethyl)phenylsulphonyl-D-leucinol,
N-Ethyl-N-4-(1H-2-methylimidazo[4,5-c]pyridinylmethyl)phenylsulphonyl-L-leucinol,
N-Allyl-N-4-(1H-2-methylimidazo[4,5-c]pyridinylmethyl)phenylsulphonyl-L-leucinol,
N-Propyl-N-4-(1H-2-methylimidazo[4,5-c]pyridinylmethyl)phenylsulphonyl-L-leucinol,
N-Benzyl-N-4-(1H-2-methylimidazo[4,5-c]pyridinylmethyl)phenylsulphonyl-L-leucinol,
N-4-Methoxybenzyl-N-4-(1H-2-methyl imidazo[4,5-c]pyridinylmethyl)phenylsulphonyl-L-leucinol,
N-Methyl-N-4-(1H-2-methylimidazo[4,5-c]pyridinylmethyl)phenylsulphonyl-L-isoleucinol,
N-Methyl-N-4-(1H-2-methylimidazo[4,5-c]pyridinylmethyl)phenylsulphonyl-L-phenylalaninol,
N-Methyl-N-4-(1H-2-methylimidazo[4,5-c]pyridinylmethyl)phenylsulphonyl-L-valinol,
N-Methyl-N-4-(1H-2-methylimidazo[4,5-c]pyridinylmethyl)phenylsulphonyl-L-tryptophanol,
N-Methyl-N-4-(1H-2-methylimidazo[4,5-c]pyridinylmethyl)phenylsulphonyl-L-methioninol,
N-Methyl-N-4-(1H-2-methylimidazo[4,5-c]pyridinylmethyl)phenylsulphonyl-O-methyl-L-tyrosinol,
N-Methyl-N-4-(1H-2-methylimidazo[4,5-c]pyridinylmethyl)phenylsulphonyl-L-norleucinol,
N-Methyl-N-4-(1H-2-methylimidazo[4,5-c]pyridinylmethyl)phenylsulphonyl-L-phenylglycinol,
N-Methyl-N-4-(1H-2-methylimidazo[4,5-c]pyridinylmethyl)phenylsulphonyl-L-t-butylglycinol,
N-Methyl-N-4-(1H-2-methylimidazo[4,5-c]pyridinylmethyl)phenylsulphonyl-D,L-ethylglycinol,
N-Methyl-N-4-(1H-2-methylimidazo[4,5-c]pyridinylmethyl)phenylsulphonyl-D,L-allylglycinol,
N-Methyl-N-4-(1H-2-methylimidazo[4,5-c]pyridinylmethyl)phenylsulphonyl-L-cyclopropylalaninol,
N-Methyl-N-4-(1H-2-methylimidazo[4,5-c]pyridinylmethyl)phenylsulphonyl-L-cyclopentylalaninol,
N-Methyl-N-4-(1H-2-methylimidazo[4,5-c]pyridinylmethyl)phenylsulphonyl-L-cyclohexylalaninol,
O-Ethanoyl-N-methyl-N-4-(1H-2-methylimidazo[4,5-c]pyridinylmethyl)phenylsulphonyl-L-leucinol,
O-Ethanoyl-N-methyl-N-4-(1H-2-methylimidazo[4,5-c]pyridinylmethyl)phenylsulphonyl-D-leucinol,
O-Ethanoyl-N-ethyl-N-4-(1H-2-methylimidazo[4,5-c]pyridinylmethyl)phenylsulphonyl-L-leucinol,
O-Ethanoyl-N-allyl-N-4-(1H-2-methylimidazo[4,5-c]pyridinylmethyl)phenylsulphonyl-L-leucinol,
O-Ethanoyl-N-propyl-N-4-(1H-2-methylimidazo[4,5-c]pyridinylmethyl)phenylsulphonyl-L-leucinol,
O-Ethanoyl-N-benzyl-N-4-(1H-2-methylimidazo[4,5-c]pyridinylmethyl)phenylsulphonyl-L-leucinol,
O-Ethanoyl-N-4-methoxybenzyl-N-4-(1H-2-methylimidazo[4,5-c]pyridinylmethyl)phenylsulphonyl-L-leucinol,
O-Ethanoyl-N-methyl-N-4-(1H-2-methylimidazo[4,5-c]pyridinylmethyl)phenylsulphonyl-L-isoleucinol,
O-Ethanoyl-N-methyl-N-4-(1H-2-methylimidazo[4,5-c]pyridinylmethyl)phenylsulphonyl-L-phenylalininol,
O-Ethanoyl-N-methyl-N-4-(1H-2-methylimidazo[4,5-c]pyridinylmethyl)phenylsulphonyl-L-valinol,
O-Ethanoyl-N-methyl-N-4-(1H-2-methylimidazo[4,5-c]pyridinylmethyl)phenylsulphonyl-L-tryptophanol,
O-Ethanoyl-N-methyl-N-4-(1H-2-methylimidazo[4,5-c]pyridinylmethyl)phenylsulphonyl-L-methioninol,
O-Ethanoyl-N-methyl-N-4-(1H-2-methylimidazo[4,5-c]pyridinylmethyl)phenylsulphonyl-O'-methyl-L-tyrosinol,
O-Ethanoyl-N-methyl-N-4-(1H-2-methylimidazo[4,5-c]pyridinylmethyl)phenylsulphonyl-L-norleucinol,
O-Ethanoyl-N-methyl-N-4-(1H-2-methylimidazo[4,5-c]pyridinylmethyl)phenylsulphonyl-L-phenylglycinol,
O-Ethanoyl-N-methyl-N-4-(1H-2-methylimidazo[4,5-c]pyridinylmethyl)phenylsulphonyl-L-t-butylglycinol,
O-Ethanoyl-N-methyl-N-4-(1H-2-methylimidazo[4,5-c]pyridinylmethyl)phenylsulphonyl-D,L-ethylglycinol,
O-Ethanoyl-N-methyl-N-4-(1H-2-methylimidazo[4,5-c]pyridinylmethyl)phenylsulphonyl-D,L-allylglycinol,
O-Ethanoyl-N-methyl-N-4-(1H-2-methylimidazo[4,5-c]pyridinylmethyl)phenylsulphonyl-L-cyclopropylalininol,
O-Ethanoyl-N-methyl-N-4-(1H-2-methylimidazo[4,5-c]pyridinylmethyl)phenylsulphonyl-L-cyclopentylalininol,
O-Ethanoyl-N-methyl-N-4-(1H-2-methylimidazo[4,5-c]pyridinylmethyl)phenylsulphonyl-L-cyclohexylalininol,
O-Octadecanoyl-N-methyl-N-4-(1H-2-methylimidazo[4,5-c]pyridinylmethyl)phenylsulphonyl-L-leucinol,
O-Propanoyl-N-methyl-N-4-(1H-2-methylimidazo[4,5-c]pyridinylmethyl)phenylsulphonyl-L-leucinol,
O-2-Furoyl-N-methyl-N-4-(1H-2-methylimidazo[4,5-c]pyridinylmethyl)phenylsulphonyl-L-leucinol,
O-Ethyloxaloyl-N-methyl-N-4-(1H-2-methylimidazo[4,5-c]pyridinylmethyl)phenylsulphonyl-L-leucinol,
O-Benzoyl-N-methyl-N-4-(1H-2-methylimidazo[4,5-c]pyridinylmethyl)phenylsulphonyl-L-leucinol,
O-2-Acetoxybenzoyl-N-methyl-N-4-(1H-2-methylimidazo[4,5-c]pyridinylmethyl)phenylsulphonyl-L-leucinol,
O-Propanoyl-N-4-(1H-2-methylimidazo[4,5-c]pyridinylmethyl)phenylsulphonyl-L-leucinol,
O-Propanoyl-N-ethyl-N-4-(1H-2-methylimidazo[4,5-c]pyridinylmethyl)phenylsulphonyl-L-leucinol,
O-Propanoyl-N-allyl-N-4-(1H-2-methylimidazo[4,5-c]pyridinylmethyl)phenylsulphonyl-L-leucinol,
O-Propanoyl-N-methoxybenzyl-N-4-(1H-2-methylimidazo[4,5-c]pyridinylmethyl)phenylsulphonyl-L-leucinol,
O-Propanoyl-N-methyl-N-4-(1H-2-methylimidazo[4,5-c]pyridinylmethyl)phenylsulphonyl-L-isoleucinol,
O-Propanoyl-N-methyl-N-4-(1H-2-methylimidazo[4,5-c]pyridinylmethyl)phenylsulphonyl-L-cyclopentylalininol,
O-Butanoyl-N-methyl-N-4-(1H-2-methylimidazo[4,5-c]pyridinylmethyl)phenylsulphonyl-L-leucinol,
O-Pentanoyl-N-methyl-N-4-(1H-2-methylimidazo[4,5-c]pyridinylmethyl)phenylsulphonyl-L-leucinol, O-Hexanoyl-N-methyl-N-4-(1H-2-methylimidazo[4,5-c]pyridinylmethyl)phenylsulphonyl-L-leucinol,
O-Octanoyl-N-methyl-N-4-(1H-2-methylimidazo[4,5-c]pyridinylmethyl)phenylsulphonyl-L-leucinol,
O-Decanoyl-N-methyl-N-4-(1H-2-methylimidazo[4,5-c]pyridinylmethyl)phenylsulphonyl-L-leucinol,
O-Dodecanoyl-N-methyl-N-4-(1H-2-methylimidazo[4,5-c]pyridinylmethyl)phenylsulphonyl-L-leucinol,
O-Tetradecanoyl-N-methyl-N-4-(1H-2-methylimidazo[4,5-c]pyridinylmethyl)phenylsulphonyl-L-leucinol,
O-Hexadecanoyl-N-methyl-N-4-(1H-2-methylimidazo[4,5-c]pyridinylmethyl)phenylsulphonyl-L-leucinol,
O-2-Thiophenecarbonyl-N-methyl-N-4-(1H-2-methylimidazo[4,5-c]pyridinylmethyl)phenylsulphonyl-L-leucinol,
O-2-Tetrahydrofuroyl-N-methyl-N-4-(1H-2-methylimidazo[4,5-c]pyridinylmethyl)phenylsulphonyl-L-leucinol,
O-2-Pyridinecarbonyl-N-Methyl-N-4-(1H-2-methylimidazo[4,5-c]pyridinylmethyl)phenylsulphonyl-L-leucinol,
O-3-Pyridinecarbonyl-N-methyl-N-4-(1H-2-methylimidazo[4,5-c]pyridinylmethyl)phenylsulphonyl-L-leucinol,
O-4-Pyridinecarbonyl-N-methyl-N-4-(1H-2-methylimidazo[4,5-c]pyridinylmethyl)phenylsulphonyl-L-leucinol,
O-3-Quinolinecarbonyl-N-methyl-N-4-(1H-2-methylimidazo[4,5-c]pyridinylmethyl)phenylsulphonyl-L-leucinol,
O-2-Trifluoromethylbenzoyl-N-methyl-N-4-(1H-2-methylimidazo[ 4,5-c]pyridinylmethyl)phenylsulphonyl-L-leucinol,
O-2-Bromobenzoyl-N-methyl-N-4-(1H-2-methylimidazo[4,5-c]pyridinylmethyl)phenylsulphonyl-L-leucinol,
O-3-Chlorobenzoyl-N-methyl-N-4-(1H-2-methylimidazo[4,5-c]pyridinylmethyl)phenylsulphonyl-L-leucinol,
O-4-Methoxybenzoyl-N-methyl-N-4-(1H-2-methylimidazo[4,5-c]pyridinylmethyl)phenylsulphonyl-L-leucinol,
O-4-Fluorobenzoyl-N-methyl-N-4-(1H-2-methylimidazo[4,5-c]pyridinylmethyl)phenylsulphonyl-L-leucinol,
O-3,4-Dimethoxybenzoyl-N-methyl-N-4-(1H-2-methylimidazo[4,5-c]pyridinylmethyl)phenylsulphonyl-L-leucinol,
O-3-Chloro-4-methoxybenzoyl-N-methyl-N-4-(1H-2-methylimidazo[ 4,5-c]pyridinylmethyl)phenylsulphonyl-L-leucinol,
O-2,2-Dimethylpropanoyl-N-methyl-N-4-(1H-2-methylimidazo[ 4,5-c]pyridinylmethyl)phenylsulphonyl-L-leucinol,
O-2-(3,4-Dimethoxyphenylmercapto)ethanoyl-N-methyl-N-4-(1H-2-methylimidazo[4,5-c]pyridinylmethyl)phenylsulphonyl-L-leucinol,
O-Retinoyl-N-methyl-N-4-(1H-2-methylimidazo[4,5-c]pyridinylmethyl)phenylsulphonyl-L-leucinol,
O-2-(4-Methoxyphenyl)ethanoyl-N-methyl-N-4-(1H-2-methylimidazo[ 4,5-c]pyridinylmethyl)phenylsulphonyl-L-leucinol,
O-2-(3,4-Dimethoxyphenyl)ethanoyl-N-methyl-N-4-(1H-2-methylimidazo[ 4,5c]pyridinylmethyl)phenylsulphonyl-L-leucinol,
O-3-(4-Methoxyphenyl)propanoyl-N-methyl-N-4-(1H-2-methylimidazo[ 4,5-c]pyridinylmethyl)phenylsulphonyl-L-leucinol,
O-3-(3,4-Dimethoxyphenyl)propanoyl-N-methyl-N-4-(1H-2-methylimidazo[4,5-c]pyridinylmethyl)phenylsulphonyl-L-leucinol,
O-3-(3-Chloro-4-methoxyphenyl)propanoyl-N-methyl-N-4-(1H-2-methylimidazo[ 4,5-c]pyridinylmethyl)phenylsulphonyl-L-leucinol,
O-3-(Pyridin-3-yl)propanoyl-N-methyl-N-4-(1H-2-methylimidazo[ 4,5-c]pyridinylmethyl)phenylsulphonyl-L-leucinol,
O-(N'-Benzyloxycarbonyl)-L-leucinoyl-N-methyl-N-4-(1H-2-methylimidazo[4,5-c]pyridinylmethyl)phenylsulphonyl-L-leucinol,
O-(N',N'-Dibenzyl)-L-leucinoyl-N-methyl-N-4-(1H-2-methylimidazo[ 4,5-c]pyridinylmethyl)phenylsulphonyl-L-leucinol,
O-(N'-Benzyloxycarbonyl)glycinoyl-N-methyl-N-4-(1H-2-methylimidazo[ 4,5c]pyridinylmethyl)phenylsulphonyl-L-leucinol,
O-(N'-Benzyloxycarbonyl)-D-leucinoyl-N-methyl-N-4-(1H-2-methylimidazo[4,5-c]pyridinylmethyl)phenylsulphonyl-L-leucinol,
O-(N'-Benzyloxycarbonyl)-L-phenylalininoyl-N-methyl-N-4-(1H-2-methylimidazo[ 4,5-c]pyridinylmethyl)phenylsulphonyl-L-leucinol,
O-(N',N'-dibenzyl)glycinoyl-N-methyl-N-4-(1H-2-methylimidazo[ 4,5-c]pyridinylmethyl)phenylsulphonyl-L-leucinol,
O-(N'-Benzyloxycarbonyl)-L-norleucinoyl-N-methyl-N-4-(1H-2-methylimidazo[ 4,5-c]pyridinylmethyl)phenylsulphonyl-L-leucinol,
O-(N'-Butoxycarbonyl)-L-leucinoyl-N-methyl-N-4-(1H-2-methylimidazo[ 4,5c]pyridinylmethyl)phenylsulphonyl-L-leucinol,
O-(N'-Benzyloxycarbonyl)-L-valinoyl-N-methyl-N-4-(1H-2-methylimidazo[4,5-c]pyridinylmethyl)phenylsulphoriyl-L-leucinol,
O-(N'-Benzyloxycarbonyl)-L-phenylglycinoyl-N-methyl-N-4-(1H-2-methylimidazo[4,5-c]pyridinylmethyl)phenylsulphonyl-L-leucinol,
O-Diethoxyphosphoryl-N-methyl-N-4-(1H-2-methylimidazo[ 4,5-c]pyridinylmethyl)phenylsulphonyl-L-leucinol,
O-Dimethoxyphosphoryl-N-methyl-N-4-(1H-2-methylimidazo[ 4,5-c]pyridinylmethyl)phenylsulphonyl-L-leucinol,
O-Diphenoxyphosphoryl-N-methyl-N-4-(1H-2-methylimidazo[ 4,5-c ]pyridinylmethyl)phenylsulphonyl-L-leucinol,
O-Diisopropoxyphosphoryl-N-methyl-N-4-(1H-2-methylimidazo[ 4,5-c]pyridinylmethyl)phenylsulphonyl-L-leucinol,
O-Methylsulphonyl-N-methyl-N-4-(1H-2-methylimidazo[ 4,5-c]pyridinylmethyl)phenylsulphonyl-L-leucinol,
O-Ethylsulphonyl-N-methyl-N-4-(1H-2-methylimidazo[4,5-c]pyridinylmethyl)phenylsulphonyl-L-leucinol,
O-Propylsulphonyl-N-methyl-N-4-(1H-2-methylimidazo[4,5-c]pyridinylmethyl)phenylsulphonyl-L-leucinol,
O-Phenylsulphonyl-N-methyl-N-4-(1H-2-methylimidazo[4,5-c]pyridinylmethyl)phenylsulphonyl-L-leucinol,
O-4-Methylphenylsulphonyl-N-methyl-N-4-(1H-2-methylimidazo[ 4,5-c]pyridinylmethyl)phenylsulphonyl-L-leucinol,
O-Benzylaminocarbonyl-(N-methyl-N-4-(1H-2-methylimidazo[ 4,5-c]pyridinylmethyl)phenylsulphonyl)-L-leucinol,
O-4-Ethoxycarbonylpiperazinecarbonyl-N-methyl-N-4-(1H-2-methylimidazo[4,5-c]pyridinylmethyl)phenylsulphonyl-L-leucinol,
O-5-Ethyl-1,3,4-thiadiazol-2-ylaminocarbonyl-N-methyl-N-4-(1H-2-methylimidazo[ 4,5-c]pyridinylmethyl)phenylsulphonyl-L-leucinol,
O-Pyridin-2-ylmethylaminocarbonyl-N-methyl-N-4-(1H-2-methylimidazo[ 4,5c]pyridinylmethyl)phenylsulphonyl-L-leucinol,
O-Octadecylaminocarbonyl-(N-methyl-N-4-(1H-2-methylimidazo[ 4,5-c]pyridinylmethyl)phenylsulphonyl-L-leucinol,
O-Methylaminocarbonyl-(N-methyl-N-4-(1H-2-methylimidazo[ 4,5-c]pyridinylmethyl)phenylsulphonyl-L-leucinol,
O-Ethylaminocarbonyl-(N-methyl-N-4-(1H-2-methylimidazo[ 4,5-c]pyridinylmethyl)phenylsulphonyl-L-leucinol, O-n-Propylaminocarbonyl-(N-methyl-N-4-(1H-2-methylimidazo[4,5-c]pyridinylmethyl)phenylsulphonyl-L-leucinol,
O-i-Propylaminocarbonyl-(N-methyl-N-4-(1H-2-methylimidazo[4,5-c]pyridinylmethyl)phenylsulphonyl-L-leucinol,
O-n-Pentylaminocarbonyl-(N-methyl-N-4-(1H-2-methylimidazo[4,5-c]pyridinylmethyl)phenylsulphonyl-L-leucinol,
O-n-Hexylaminocarbonyl-(N-methyl-N-4-(1H-2-methylimidazo[4,5-c]pyridinylmethyl)phenylsulphonyl-L-leucinol,
O-n-Octylaminocarbonyl-(N-methyl-N-4-(1H-2-methylimidazo[4,5-c]pyridinylmethyl)phenylsulphonyl-L-leucinol,
O-n-Decylaminocarbonyl-(N-methyl-N-4-(1H-2-methylimidazo[4,5-c]pyridinylmethyl)phenylsulphonyl-L-leucinol,
O-n-Dodecylamino carbonyl-(N-methyl-N-4-(1H-2-methylimidazo[4,5-c]pyridinylmethyl)phenylsulphonyl-L-leucinol,
O-n-Tetradecylaminocarbonyl-(N-methyl-N-4-(1H-2-methylimidazo[4,5-c]pyridinylmethyl)phenylsulphonyl-L-leucinol,
O-n-Hexadecylaminocarbonyl-(N-methyl-N-4-(1H-2-methylimidazo[4,5-c]pyridinylmethyl)phenylsulphonyl-L-leucinol,
O-t-Butylaminocarbonyl-(N-methyl-N-4-(1H-2-methylimidazo[4,5-c]pyridinylmethyl)phenylsulphonyl-L-leucinol,
O-Pyridin-2-ylaminocarbonyl-(N-methyl-N-4-(1H-2-methylimidazo[4,5-c]pyridinylmethyl)phenylsulphonyl-L-leucinol,
O-Pyridin-4-ylmethylaminocarbonyl-N-methyl-N-4-(1H-2-methylimidazo[4,5-c]pyridinylmethyl)phenylsulphonyl-L-leucinol,
O-Pyridin-3-ylmethylaminocarbonyl-N-methyl-N-4-(1H-2-methylimidazo[4,5c]pyridinylmethyl)phenylsulphonyl-L-leucinol,
O-4-Methoxyphenylaminocarbonyl-N-methyl-N-4-(1H-2-methylimidazo[4,5-c]pyridinylmethyl)phenylsulphonyl-L-leucinol,
O-3,4-Dimethoxybenzylaminocarbonyl-N-methyl-N-4-(1H-2-methylimidazo[4,5-c]pyridinylmethyl)phenylsulphonyl-L-leucinol,
O-2-(4-Methoxyphenyl)ethylaminocarbonyl-N-methyl-N-4-(1H-2-methylimidazo[4,5-c]pyridinylmethyl)phenylsulphonyl-L-leucinol,
O-2-(3,4-Dimethoxyphenyl)ethylaminocarbonyl-N-methyl-N-4-(1H-2-methylimidazo[4,5-c]pyridinylmethyl)phenylsulphonyl-L-leucinol,
O-3-(3,4-Dimethoxyphenyl)propylaminocarbonyl-N-methyl-N-4-(1H-2-methylimidazo[4,5-c]pyridinylmethyl)phenylsulphonyl-L-leucinol,
O-3-(Pyridin-3-yl)propylaminocarbonyl-(N-methyl-N-4-(1H-2-methylimidazo[4,5-c]pyridinylmethyl)phenylsulphonyl-L-leucinol,
N-Methyl-N-4-(1H-2-methylimidazo[4,5-c]pyridinylmethyl)phenylsulphonyl-2-thienylmethylamine,
N-Methyl-N-4-(1H-2-methylimidazo[4,5-c]pyridinylmethyl)phenylsulphonyl-tetrahydrofurfurylamine,
N-4-(1H-2-Methylimidazo[4,5-c]pyridinylmethyl)phenylsulphonyl-2-(N'-methylpyrrol- 2-yl)ethylamine,
N-Methyl-N-4-(1H-2-methylimidazo[4,5-c]pyridinylmethyl)phenylsulphonyl-1(4-fluorophenyl)- 1-(2-thienyl)methylamine,
N-4-(1H-2-Methyl imidazo[4,5-c]pyridinylmethyl)phenylsulphonyl-1-(2-thienyl)propylamine,
N-Methyl-N-4-(1H-2-methylimidazo[4,5-c]pyridinylmethyl)phenylsulphonyl-1(2-furyl)-3-methylbutylamine,
N-4-(1H-2-Methylbenzimidazolylmethyl)phenylsulphonyl-1-(2-benzothiazolyl)-3-methylbutylamine,
N-Methyl-N-4-(1H-2-methylimidazo[4,5-c]pyridinylmethyl)phenylsulphonyl-1(2-thienyl)-3-methylbutylamine,
N-Methyl-N-4-(1H-2-methylimidazo[4,5-c]pyridinylmethyl)phenylsulphonyl- 1-(pyridin-3-yl)-3-methylbutylamine,
N-Methyl-N-4-(1H-2-methylimidazo[4,5-c]pyridinylmethyl)phenylsulphonyl- 1-(N'-methyl-2-pyrrolyl)-3-methylbutylamine,
N-Methyl-N-4-(1H-2-methylimidazo[4,5-c]pyridinylmethyl)phenylsulphonyl- 1(pyrazin-2-yl)-3-methylbutylainine,
N-Methyl-N-4-(1H-2-methylimidazo[4,5-c]pyridinylmethyl)phenylsulphonyl- 1-(6-methylpyrazin-2-yl)-3-methylbutylamine,
N-Methyl-N-4-(1H-2-methylimidazo[4,5-c]pyridinylmethyl)phenylsulphonyl- 1-(6-ethylpyrazin-2-yl)-3-methylbutylamine,
N-Methyl-N-4-(1H-2-methylimidazo[4,5-c]pyridinylmethyl)phenylsulphonyl- 1-(6-ethyl-1,2-pyridazin-3-yl)-3-methylbutylamine,
N-Methyl-N-4-(1H-2-methylimidazo[4,5-c]pyridinylmethyl)phenylsulphonyl-1-(2-ethyl-1,3-pyrimidin-5-yl)-3-methylbutylamine,
N-Methyl-N-4-(1H-2-methylimidazo[4,5-c]pyridinylmethyl)phenylsulphonyl- 1-(1,3-dithian-2-yl)-3-methylbutylamine,
N-Methyl-N-4-(1H-2-methylimidazo[4,5-c]pyridinylmethyl)phenylsulphonyl- 1-(2-thienyl)pentylamine,
N-Methyl-N-4-(1H-2-methylimidazo[4,5-c]pyridinylmethyl)phenylsulphonyl- 1-(4-fluorophenyl)-1-(2-furyl)methylamine,
N-Methyl-N-4-(1H-2-methylimidazo[4,5-c]pyridinylmethyl)phenylsulphonyl- 2(4-methoxyphenyl)-1-(2-furyl)ethylamine,
N-Methyl-N-4-(1H-2-methylimidazo[4,5-c]pyridinylmethyl)phenylsulphonyl- 1-(pyridin-2-yl)-3-methylbutylamine,
N-Methyl-N-4-(1H-2-methylimidazo[4,5-c]pyridinylmethyl)phenylsulphonyl- 1-(2-methoxypyridin-3-yl)-3-methylbutylamine,
N-Methyl-N-4-(1H-2-methylimidazo[4,5-c]pyridinylmethyl)phenylsulphonyl- 1-(pyridin-3-ylmethyl)-3-methylbutylamine,
N-Methyl-N-4-(1H-2-methylimidazo[4,5-c]pyridinylmethyl)phenylsulphonyl- 1-(2-benzo[b]thienyl)-3-methylbutylamine,
N-Methyl-N-4-(1H-2-methylimidazo[4,5-c]pyridinylmethyl)phenylsulphonyl- 1-(3-methylisoxazol-5-ylmethyl)-3-methylbutylamine,
N-Methyl-N-4-(1H-2-methylbenzimidazolylmethyl)phenylsulphonyl-1-( 3-methyl-1,2,4-oxadiazol-5-yl)-3-methylbutylamine,
N-Methyl-N-4-(1H-2-methylimidazo[4,5-c]pyridinylmethyl)phenylsulphonyl- 1-(3-ethyl-1,2,4-oxadiazol-5-yl)-3-methylbutylamine,
N-Methyl-N-4-(1H-2-methylimidazo[4,5-c]pyridinylmethyl)phenylsulphonyl- 1-(3-octadecyl-1,2,4-oxadiazol-5-yl)-3-methylbutylamine,
N-Methyl-N-4-(1H-2-methylimidazo[4,5-c]pyridinylmethyl)phenylsulphonyl-1(3-propyl-1,2,4-oxadiazol-5-yl)-3-methylbutylamine,
N-Methyl-N-4-(1H-2-methylimidazo[4,5-c]pyridinylmethyl)phenylsulphonyl-1(3-n-butyl-1,2,4-oxadiazol-5-yl)-3-methylbutylamine,
N-Methyl-N-4-(1H-2-methylimidazo[4,5-c]pyridinylmethyl)phenylsulphonyl-1(3-phenyl-1,2,4-oxadiazol-5-yl)-3-methylbutylamine, N-Methyl-N-4-(1H-2-methylimidazo[4,5-c]pyridinylmethyl)phenylsulphonyl-1(3-benzyl-1,2,4-oxadiazol-5-yl)-3-methylbutylamine, N-Methyl-N-4-(1H-2-methylimidazo[4,5-c]pyridinylmethyl)phenylsulphonyl-1(5-methyl-1,3,4-oxadiazol-2-yl)-3-methylbutylamine, N-Methyl-N-4-(1H-2-methylimidazo[4,5-c]pyridinylmethyl)phenylsulphonyl-1(5-ethyl-1,3,4-oxadiazol-2-yl)-3-methylbutylamine, N-Methyl-N-4-(1H-2-methylimidazo[4,5-c]pyridinylmethyl)phenylsulphonyl-1(5-propyl-1,3,4-oxadiazol-2-yl)-3-methylbutylamine, N-Methyl-N-4-(1H-2-methylimidazo[4,5-c]pyridinylmethyl)phenylsulphonyl-1(5-phenyl-1,3,4-oxadiazol-2-yl)-3-methylbutylamine, N-Methyl-N-4-(1H-2-methylimidazo[4,5-c]pyridinylmethyl)phenylsulphonyl-β-alanine ethyl ester, N-Methyl-N-4-(1H-2-methylimidazo[4,5-c]pyridinylmethyl)phenylsulphonyl-3-amino-5-methylhexanoic acid ethyl ester, N-Methyl-N-4-(1H-2-methylimidazo[4,5-c]pyridinylmethyl)phenylsulphonyl-3-amino-5-methylhexanoic acid isopropyl ester, N-Methyl-N-4-(1H-2-methylimidazo[4,5-c]pyridinylmethyl)phenylsulphonyl-3-amino-5-methylhexanoic acid n-butyl ester, N-Methyl-N-4-(1H-2-methylimidazo[4,5-c]pyridinylmethyl)phenylsulphonyl-3-amino-5-methylhexanoic acid benzyl ester, N-Methyl-N-4-(1H-2-methylimidazo[4,5-c]pyridinylmethyl)phenylsulphonyl-3amino4-phenylbutanote acid ethyl ester, N-Methyl-N-4-(1H-2-methylimidazo[4,5-c]pyridinylmethyl)phenylsulphonyl-3-amino-4-(4-methoxyphenyl)butanoic acid ethyl ester, and a salt of a compound thereof.

11. The compound of claim 1 wherein said compound is a pharmaceutically or veterinarily acceptable addition salt or hydrate thereof.

12. A pharmaceutical or veterinary composition comprising the compound of any one of claims 1 or 10 and a pharmaceutically or veterinarily acceptable carrier.

13. A method for the treatment or prophylaxis of diseases or physiological conditions of humans or mamalian animals mediated by platelet activating factor, comprising administering to a patient an amount of the compound of any one of claims 1 or 10 effective to antagonise the effects of platelet activating factor on target cells responsible for such diseases or physiological conditions.

14. A method for the treatment or prophylaxis of diseases or physiological conditions of humans or mammalian animals mediated by platelet activating factor, comprising administering to a human or mammalian animal an amount of the pharmaceutical or veterinary composition of claim 12 effective to antagonize the affects of platelet activating factor on target cells responsible for such diseases or physiological conditions.

* * * * *